United States Patent [19]

Adams et al.

[11] Patent Number: 5,859,051
[45] Date of Patent: Jan. 12, 1999

[54] ANTIDIABETIC AGENTS

[75] Inventors: Alan D. Adams, Cranford, N.J.; Gregory D. Berger, Stonington, Conn.; Jeffrey P. Bergman, Tenafly, N.J.; Joel P. Berger, Hoboken, N.J.; Wei Han, Edison, N.J.; Mark D. Leibowitz, Millburn, N.J.; David E. Moller, Bedminster, N.J.; Conrad Santini, Warren, N.J.; Soumya P. Sahoo, Old Bridge, N.J.; Richard L. Tolman, Warren, N.J.; Jonthan R. Young, Dayton, N.J.

[73] Assignee: Merck & Co., Inc., Rahway, N.J.

[21] Appl. No.: 791,213

[22] Filed: Jan. 31, 1997

Related U.S. Application Data

[60] Provisional application No. 60/011,094 Feb. 2, 1996 and provisional application No. 034,433 Dec. 23, 1996.

[51] Int. Cl.$^6$ .................. C07D 307/78; A61K 31/365; A61K 31/37
[52] U.S. Cl. .................. 514/469; 514/307; 514/415; 514/457; 546/146; 548/469; 549/283; 549/462
[58] Field of Search .................. 548/469; 514/469, 514/307, 415, 457; 546/146; 549/283, 462

[56] References Cited

U.S. PATENT DOCUMENTS

| | | | |
|---|---|---|---|
| 4,758,586 | 7/1988 | Chan et al. | 514/415 |
| 4,820,867 | 4/1989 | Belanger et al. | 562/478 |
| 5,002,953 | 3/1991 | Hindley | 514/275 |
| 5,232,925 | 8/1993 | Hindley | 514/272 |
| 5,324,743 | 6/1994 | Dillard et al. | 514/456 |
| 5,453,443 | 9/1995 | Perrier et al. | 562/429 |
| 5,480,645 | 1/1996 | Delle Valle et al. | 424/439 |
| 5,480,910 | 1/1996 | Holloway et al. | 514/567 |
| 5,534,536 | 7/1996 | Ohuchida et al. | 424/439 |

FOREIGN PATENT DOCUMENTS

| | | |
|---|---|---|
| 0 039 913 | 11/1981 | European Pat. Off. . |
| 0 061 800 | 10/1982 | European Pat. Off. . |
| 0 123 541 | 10/1984 | European Pat. Off. . |
| 447189 | 9/1991 | European Pat. Off. ............... 549/369 |
| 0 579 412 A1 | 1/1994 | European Pat. Off. . |
| 0 611 003 A1 | 8/1994 | European Pat. Off. . |
| 0 617 001 A1 | 9/1994 | European Pat. Off. . |
| 2 058 785 A | 5/1979 | United Kingdom . |
| WO 93/21166 | 10/1993 | WIPO . |
| WO 94/01420 | 1/1994 | WIPO . |
| WO 94/12461 | 6/1994 | WIPO . |
| WO 94/29285 | 12/1994 | WIPO . |
| WO 95/03288 | 2/1995 | WIPO . |
| WO 95/17183 | 6/1995 | WIPO . |

OTHER PUBLICATIONS

Merck Manual, 16th Ed.: pp. 1039–1040 (1992).
Gordon, et al., *Am. J. Med.*, 62: pp. 707–714 (1977).
Stampfer, et al., *New England J. Med.*: 325, pp. 373–381 (1991).
Kannel, et al., *Ann. Internal Med.*, 90: pp. 85–91 (1979).
Elbrecht, et al., *BBRC*, 224: pp. 431–437 (1996).
A. Schmidt et al., *Molecular Endocrinology*, 6: pp. 1634–1641 (1992).
National Cholesterol Educ. Prog., *JAMA*, 269: pp. 3015–3023 (1993).
T. Sher et al., *Biochem.*, 32: pp. 5598–5604 (1993).
R.J. Havel et al., *Metabolic Basis of Inherited Disease*, 6th Ed.: pp. 1129–1138, (1989).

*Primary Examiner*—Zinna Northington Davis
*Attorney, Agent, or Firm*—Richard C. Billups; Sylvia A. Ayler; David L. Rose

[57] ABSTRACT

The instant invention is concerned with acetylphenols which are useful as antiobesity and antidiabetic compounds. Compositions and methods for the use of the compounds in the treatment of diabetes and obesity and for lowering or modulating triglyceride levels and cholesterol levels or raising high density lipoprotein levels or for increasing gut motility or for treating atherosclerosis are also disclosed.

39 Claims, No Drawings

ANTIDIABETIC AGENTS

CROSS REFERENCE TO RELATED APPLICATIONS

This application is a non-provisional application related to provisional application nos. 60/011,094 filed on Feb. 2, 1996 and 60/034,433 filed on Dec. 23, 1996, priority of which is claimed hereunder.

BACKGROUND OF THE INVENTION

Diabetes refers to a disease process derived from multiple causative factors and characterized by elevated levels of plasma glucose or hyperglycemia. Uncontrolled hyperglycemia is associated with increased and premature mortality due to an increased risk for microvascular and macrovascular diseases, including nephropathy, neuropathy, retinopathy, hypertension, stroke, and heart disease. Therefore, control of glucose homeostasis is a critically important approach for the treatment of diabetes.

Type I diabetes (IDDM) is the result of an absolute deficiency of insulin, the hormone which regulates glucose utilization. Type II, noninsulin dependent diabetes mellitus (NIDDM) is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver.

The several treatments for NIDDM, which has not changed substantially in many years, are all with limitations. While physical exercise and reductions in dietary intake of calories will dramatically improve the diabetic condition, compliance with this treatment is very poor because of well-entrenched sedentary lifestyles and excess food consumption, especially high fat-containing food. Increasing the plasma level of insulin by administration of sulfonylureas (e.g. tolbutamide, glipizide) which stimulate the pancreatic β-cells to secrete more insulin or by injection of insulin after the response to sulfonylureas fails, will result in high enough insulin concentrations to stimulate the very insulin-resistant tissues. However, dangerously low levels of plasma glucose can result from these last two treatments and increasing insulin resistance due to the even higher plasma insulin levels could theoretically occur. The biguanides increase insulin sensitivity resulting in some correction of hyperglycemia. However, the two biguanides, phenformin and metformin, can induce lactic acidosis and nausea/diarrhea, respectively.

Thiazolidinediones (glitazones) are a recently disclosed class of compounds that are suggested to ameliorate many symptoms of NIDDM. These agents increase insulin sensitivity in muscle, liver and adipose tissue in several animal models of NIDDM resulting in complete correction of the elevated plasma levels of glucose, triglycerides and nonesterified free fatty acids without any occurrence of hypoglycemia. However, serious undesirable effects have occurred in animal and/or human studies including cardiac hypertrophy, hemadilution and liver toxicity resulting in few glitazones progressing to advanced human trials.

Hyperlipidemia is a condition which is characterized by an abnormal increase in serum lipids, such as cholesterol, triglycerides and phospholipids. These lipids do not circulate freely in solution in plasma, but are bound to proteins and transported as macromolecular complexes called lipoproteins. See the *Merck Manual*, 16th Ed. 1992 (see for example pp. 1039–1040) and "Structure and Metabolism of Plasma Lipoproteins" in *Metabolic Basis of Inherited Disease*, 6th Ed. 1989, pp. 1129–1138. One form of hyperlipidemia is hypercholesterolemia, characterized by the existence of elevated LDL cholesterol levels. The initial treatment for hypercholesterolemia is often to modify the diet to one low in fat and cholesterol, coupled with appropriate physical exercise, followed by drug therapy when LDL-lowering goals are not met by diet and exercise alone. LDL is commonly known as the "bad" cholesterol, while HDL is the "good" cholesterol. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., Am. J. Med., 62, 707–714 (1977); Stampfer, et al., N. England J. Med., 325, 373–381 (1991); and Kannel, et al., Ann. Internal Med., 90, 85–91 (1979). An example of an HDL raising agent is nicotinic acid, but the quantities needed to achieve HDL raising are associated with undesirable effects, such as flushing.

It is suggested that thiazolidinedione compounds exert their effects by binding to the peroxisome proliferator activated receptor (PPAR) family of receptors, controlling certain transcription elements having to do with the biological entities listed above. See Hulin et al., Current Pharm. Design (1996) 2, 85–102. Three sub-types of PPARs have been discovered and described; they are PPARα, PPARγ and PPARδ. PPARα is activated by a number of medium and long-chain fatty acids, and it is involved in stimulating β-oxidation of fatty acids. PPARα is also involved with the activity of fibrates in rodents and humans. Fibric acid derivatives such as clofibrate, fenofibrate, bezafibrate, ciprofibrate, beclofibrate and etofibrate, as well as gemfibrozil, produce a substantial reduction in plasma triglycerides along with moderate reduction in LDL cholesterol, and they are used particularly for the treatment of hypertriglyceridemia.

The PPARγ receptor subtypes are involved in activating the program of adipocyte differentiation and are not involved in stimulating peroxisome proliferation in the liver. The DNA sequences for the PPARγ receptors are described in Elbrecht, et al., BBRC 224;431–437 (1996). Although peroxisome proliferators, including the fibrates and fatty acids, activate the transcriptional activity of PPAR's, only prostaglandin $J_2$ derivatives have been identified as natural ligands of the PPARγ subtype, which also binds thiazolidinedione antidiabetic agents with high affinity. The glitazones have been shown to bind exclusively to the PPARγ subtype.

The human nuclear receptor gene PPARδ (hPPARδ) has been cloned from a human osteosarcoma cell cDNA library and is fully described in A. Schmidt et al., *Molecular Endocrinology*, 6:1634–1641 (1992), herein incorporated by reference. It should be noted that PPARδ is also referred to in the literature as PPARβ and as NUC1, and each of these names refers to the same receptor; in Schmidt et al, the receptor is referred to as NUC1.

SUMMARY OF THE INVENTION

This invention is concerned with the compounds of formula I below and its analogs, pharmaceutically acceptable salts thereof, and bioprecursors thereof, which differ from the thiazolidinediones in that they lack the thiazolidinedione moiety and they do not lead to the array of toxicity's associated with the thiazolidinediones. The instant compounds are effective in treating diabetes, atherosclerosis, hyperglycemia, hyperlipidemia and/or obesity because they lower one or more of the following biological entities in mammals; glucose, insulin, triglycerides, fatty acids, cholesterol and the like. Thus, it is an object of this invention to describe such compounds. It is a further object to describe the specific preferred stereoisomers of the substituted compounds. A still further object is to describe processes for the preparation of such compounds. Another object is to describe methods and compositions which use the compounds as the active ingredient thereof. Further objects will become apparent from reading the following description.

DESCRIPTION OF THE INVENTION

The present invention is directed to a compound represented by formula I:

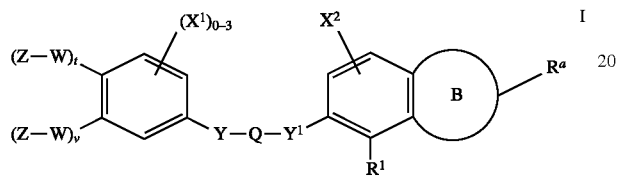

or a pharmaceutically acceptable salt thereof, wherein:

R is selected from the group consisting of H, $C_{1-6}$ alkyl, $C_{5-10}$ aryl, and $C_{5-10}$ heteroaryl, said alkyl, aryl and heteroaryl optionally substituted with 1 to 3 groups of $R^a$;

$R^1$ is selected from a group consisting of: H, $C_{1-15}$ alkyl, $C_{2-15}$ alkenyl, $C_{2-15}$ alkynyl and $C_{3-10}$ cycloalkyl, said alkyl, alkenyl, alkynyl, and cycloalkyl optionally substituted with 1 to 3 groups of $R^a$;

$R^3$ is selected from a group consisting of: H, $NHR^1$, NHacyl, $C_{1-15}$ alkyl, $C_{3-10}$ cycloalkyl, $C_{2-15}$ alkenyl, $C_{1-15}$ alkoxy, $CO_2$alkyl, OH, $C_{2-15}$ alkynyl, $C_{5-10}$ aryl, $C_{5-10}$ heteroaryl said alkyl, cycloalkyl, alkenyl, alkynyl, aryl and heteroaryl optionally substituted with 1 to 3 groups of $R^a$;

(Z—W—) is Z—$CR^6R^7$—, Z—CH=CH—, or

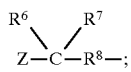

$R^8$ is selected from the group consisting of $CR^6R^7$, O, $NR^6$, and $S(O)_p$;

$R^6$ and $R^7$ are independently selected from the group consisting of H, $C_{1-6}$ alkyl;

B is selected from the group consisting of:
1) a 5 or 6 membered heterocycle containing 0 to 2 double bonds, and 1 heteroatom selected from the group consisting of O, S and N, heteroatom being substituted at any position on the five or six membered heterocycle, the heterocycle being optionally unsubstituted or substituted with 1 to 3 groups of $R^a$;
2) a 5 or 6 membered carbocycle containing 0 to 2 double bonds, the carbocycle optionally unsubstituted or substituted with 1 to 3 groups of $R^a$ at any position on the five or six membered carbocycle; and
3) a 5 or 6 membered heterocycle containing 0 to 2 double bonds, and 3 heteroatoms selected from the group consisting of O, N, and S, which are substituted at any position on the five or six membered heterocycle, the heterocycle being optionally unsubstituted or substituted with 1 to 3 groups of $R^a$;

$X^1$ and $X^2$ are independently selected from a group consisting of: H, OH, $C_{1-15}$ alkyl, $C_{2-15}$ alkenyl, $C_{2-15}$ alkynyl, halo, $OR^3$, $ORCF_3$, $C_{5-10}$ aryl, $C_{5-10}$ aralkyl, $C_{5-10}$ heteroaryl and $C_{1-10}$ acyl, said alkyl, alkenyl, alkynyl, aryl and heteroaryl optionally substituted with 1 to 3 groups of $R^a$;

$R^a$ represents a member selected from the group consisting of: halo, acyl, aryl, heteroaryl, $CF_3$, $OCF_3$, —O—, CN, $NO_2$, $R^3$, $OR^3$; $SR^3$, =N(OR), $S(O)R^3$, $SO_2R^3$, $NR^3R^3$, $NR^3COR^3$, $NR^3CO_2R^3$, $NR^3CON(R^3)_2$, $NR^3SO_2R^3$, $COR^3$, $CO_2R^3$, $CON(R^3)_2$, $SO_2N(R^3)_2$, $OCON(R^3)_2$ said aryl and heteroaryl optionally substituted with 1 to 3 groups of halo or C1–6 alkyl;

Y is selected from the group consisting of: $S(O)_p$, —$CH_2$—, —C(O)—, —C(O)NH—, —NR—, —O—, —$SO_2$NH, —$NHSO_2$;

$Y^1$ is selected from the group consisting of: O and C;

Z is selected from the group consisting of: $CO_2R^3$, $R^3CO_2R^3$, $CONHSO_2R$, $CONH_2$ and 5-(1H-tetrazole);

t and v are independently 0 or 1 such that t+v=1

Q is a saturated or unsaturated straight chain hydrocarbon containing 2–4 carbon atoms and p is 0–2.

Included in the invention is a pharmaceutical composition which is comprised of a compound of formula I in combination with a pharmaceutically acceptable carrier.

Also included in the invention is a pharmaceutical composition which is comprised of a compound of formula I in combination with one or more known sulfonylureas, biguanides, α-glucosidase inhibitors, other insulin secretogogues as well as insulin.

Also included in the invention is a method for raising high densisty lipoprotein (HDL) plasma levels in a mammal in need of such treatment comprising administering an effective amount of a compound of formula I.

Also included in the invention is a method for preventing, halting or slowing the progression of atherosclerotic cardiovascular diseases and related conditions and disease events in a mammal in need of such treatment comprising administering an effective amount of a compound of formula I.

Also included in the invention is a method for preventing, halting or slowing the progression of atherosclerotic cardiovascular diseases and related conditions and disease events in a mammal in need of such treatment comprising administering an effective amount of a compound of formula I in combination with one or more active agents such as antihyperlipidemic agents, HMG-CoA synthase inhibitors, squalene epoxidase inhibitors and the like.

Also included in the invention is a method of treating or controlling diabetes, which comprises administering to a diabetic patient an effective amount of a compound of formula I.

Also included in the invention is a method of treating or controlling diabetes, which comprises administering a compound of formula I in combination with one or more known sulfonylureas, biguanides, α-glucosidase inhibitors, other insulin secretogogues as well as insulin.

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

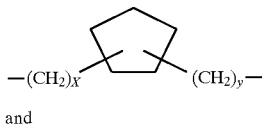
and
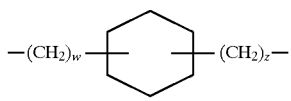

wherein: x and y=from 0–10; and w and z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

The term "alkoxy" refers to those groups of the designated carbon length in either a straight or branched configuration attached through an oxygen linkage and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term halo as used herein, represents fluoro, chloro, bromo or iodo.

Aryl refers to aromatic rings e.g., phenyl, substituted phenyl and like groups as well as rings which are fused, e.g., naphthyl and the like. Aryl thus contains at least one ring having at least 5 atoms, with up to two such rings being present, containing up to 10 atoms therein, with alternating (resonating) double bonds between adjacent carbon atoms. The preferred aryl groups are phenyl and naphthyl. Aryl groups may likewise be substituted with 0–3 groups selected from $R^a$. The preferred aryl groups are phenyl and naphthyl. Aryl groups may likewise be substituted as defined below. Preferred substituted aryls include phenyl and naphthyl substituted with zero or three groups of $R^a$.

Heteroaryl is a group containing from 5 to 10 atoms, 1–4 of which are heteroatoms, 0–4 of which heteroatoms are N and 0–1 of which are O or S, said heteroaryl group being unsubstituted or substituted with 0–3 $R^a$ groups; examples of heteroaryls are pyridyl, quinolyl, purinyl, imidazolyl, imidazopyridyl and pyrimidinyl.

One embodiment of the novel compounds of the instant invention is realized when:
Y is O and all other variables are described as above.
Another embodiment of the novel compounds of the instant invention is realized when:
Y is $S(O)_p$, p is 0–2 and all other variables are described as above.
Still another embodiment of the novel compounds of the instant invention is realized when:
Y is —CH$_2$— and all other variables are described as above.
Yet another embodiment of the novel compounds of the instant invention is realized when:
Y is CO and all other variables are described as above.
A further embodiment of the novel compounds of the instant invention is realized when:
Y is NR and all other variables are described as above.
Another embodiment of the novel compounds of the instant invention is realized when:
Y is NHSO$_2$ or SO$_2$NH and all other variables are described as above.
Another embodiment of the novel compounds of the instant invention is realized when:
Y is —C(O)NH— and all other variables are described as above.
Another embodiment of the novel compounds of the instant invention is realized when:
(Z—W—) is Z—CR$^6$R$^7$—, Z—CH=CH—, or

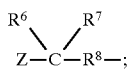

and all other variables are described as above and all other variables are described as above.
Still another embodiment of the novel compounds of the instant invention is realized when:
(Z—W—) is Z—CR$^6$R$^7$— or

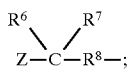

and all other variables are described as above and all other variables are described as above.
And another embodiment of the novel compounds of the instant invention is realized when:
B is a 5 or 6 membered heterocycle containing 0 to 2 double bonds, and 1 heteroatom selected from the group consisting of O, S and N, the heteroatom is substituted at any position on the five or six membered heterocycle, the heterocycle being optionally unsubstituted or substituted with 1 to 3 groups of $R^a$ and all other variables are described as above;
Still another embodiment of the novel compounds of the instant invention is realized when:
B is a 5 or 6 membered carbocycle containing 0 to 2 double bonds, the carbocycle optionally unsubstituted or substituted with 1 to 3 groups of $R^a$ at any position on the five or six membered carbocycle and all other variables are described as above;
Still another embodiment of the novel compounds of the instant invention is realized when:
B is a 5 or 6 membered heterocycle containing 0 to 2 double bonds, and 3 heteroatoms selected from the group consisting of O, S and N, which are substituted at any position on the five or six membered heterocycle, the heterocycle being optionally unsubstituted or substituted with 1 to 3 groups of $R^a$ and all other variables are described as above;.

Another embodiment of the novel compounds of the instant invention is realized when:Ra is selected from the group consisting of C1–6 alkyl, $CF_3$, aryl, halo, acyl, $OCF_3$, $-NO_2$, $OR^3$; $COR^3$, $CO_2R^3$, $CON(R^3)_2$, and $SO_2N(R^3)_2$; and X1 is selected from the group consisting of H, OH, $C_{1-6}$ alkyl, $C_{2-15}$ alkenyl, halo and $OR^3$ and all other variables are described as above.

A preferred embodiment of the novel compounds of the instant invention is realized when:

R is $C_{1-6}$ alkyl or $C_{5-10}$ aryl, said alkyl or aryl optionally substituted with 1 to 3 groups of $R^a$ $R^1$ is H or $C_{1-5}$ alkyl;

$X^1$ & $X^2$ are independently H, $C_{1-6}$ alkyl or halo;

Y is O, NH or S;

$Y^1$ is O;

(Z—W—) is Z—$CR^6R^7$— or

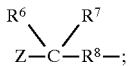

B is a 5 or 6 membered heterocycle containing 0 to 2 double bonds, and 1 heteroatom selected from the group consisting of O, S, and N, the heteroatom is substituted at any position on the five or six membered heterocycle, the heterocycle being optionally unsubstituted or substituted with 1 to 3 groups of $R^a$ and all other variables are described as above $R^a$ is a member selected from the group consisting of: halo, aryl, acyl, heteroaryl, $CF_3$, $OCF_3$, $-O-$, CN, $NO_2$, $R^3$, $OR^3$; $SR^3$, $S(O)R^3$, $SO_2R^3$, $NR^3COR^3$, $COR^3$, $CON(R^3)_2$, $SO_2N(R^3)_2$, said aryl and heteroaryl optionally substituted with 1 to 3 groups of halo or $C_{1-6}$ alkyl; and Z is $CO_2R^3$, $CONHSO_2R$, $CONH2$ or 5-(1H-tetrazole).

Examples of the compounds of the instant invention are:

Methyl 3-chloro-4-(3-(4-ethyl-8-propyl-7 coumarinoxy)propylthio)phenyl-acetate;

3-Chloro-4-(3-(4-ethyl-8-propyl-7-coumarinoxy)propylthio) phenylacetic acid;

Methyl 3-chloro-4-(3-(3-ethyl-8-propyl-7-coumarinoxy)propylthio) phenyl-acetate;

3-Chloro-4-(3-(3-ethyl-8-propyl-7-coumarinoxy)propylthio) phenylacetic acid;

3-chloro-4-(3-(4-propyl-N-(4-chlorophenyl)-5-indoleoxy) propylthio)phenylacetic acid;

1-(3-chloro-4-(3-(3-phenyl-7-propylbenzofuran-6-oxy)propyl)thiophenyl-1-cyclopropane carboxylic acid;

3-chloro-4-(3-(3-phenyl-7-propylbenzofuran-6-yloxy)propylthio)-phenylacetic acid;

Methyl 3-chloro-4-(3-(3-phenyl-7-propylbenzofuran-6-yloxy)propylthio)-phenylacetate;

3-(4-(3-phenyl-7-propylbenzofuran-6-yl)oxy)butoxy) phenylacetic acid;

4-(3-(3-Phenyl-7-propylbenzofuran-6-yloxy)propylthio)-phenyl(2,2-dimethyl)acetic acid;

3-(3-(3-Phenyl-7-propylbenzothiophen-6-yloxy)propylamino)-phenyl(2,2-dimethyl)acetic acid;

4-(3-(3-Phenyl-7-propylbenzothiophen-6-yloxy)propylamino)-phenyl(2,2-dimethyl)acetic acid;

4-(3-(3-Phenyl-7-propylbenzofuran-6-yloxy)propyloxy)-phenylpropan-3-oic acid;

4-(4-(3-Phenyl-7-propylindol-6-yloxy)butylamino)-phenylpropan-3-oic acid;

3-(3-(3-Phenyl-7-propylbenzofuran-6-yloxy)propylthio)-phenoxyacetic acid;

4-(3-(3-Phenyl-7-propylbenzofuran-6-yloxy)propylthio)-phenoxyacetic acid;

4-(4-(1-Phenyl-4-propylindol-5-yloxy)butyloxy)-phenoxyacetic acid;

N-[4-(3-(3-Phenyl-7-propylbenzofuran-6-yloxy)propylamino)-phenyl]glycine;

N-[3-(4-(4-Phenyl-8-propylquinolin-7-yloxy)butyloxy)-phenyl]glycine;

N-[4-(4-(4-Phenyl-8-propylquinolin-7-yloxy)butyloxy)-phenyl]glycine;

4-(3-(3-Phenyl-7-propylbenzofuran-6-yloxy)propylamino)-phenylacetic acid;

4-(3-(4-Phenyl-8-propylquinazolin-7-yloxy)propylthio)-phenylacetic acid;

3-(3-(3-Phenyl-7-propylindan-6-yloxy)propylamino)-3-chlorophenylacetic acid;

4-(3-(3-Phenyl-7-propylindan-6-yloxy)propylamino)-3-chlorophenylacetic acid;

4-(3-(2-Phenyl-5-propylbenzofuran-6-yloxy)propylamino)-phenylacetic acid;

3-(3-(2-Phenyl-5-propylbenzofuran-6-yloxy)propylamino)-3-chlorophenylacetic acid;

4-(3-(2-Phenyl-5-propylindol-6-yloxy)propylamino)-3-chlorophenylacetic acid;

3-(3-(2-Phenyl-5-propylbenzothiophen-6-yloxy)propylamino)-3-chlorophenylacetic acid;

4-(3-(3-Phenyl-7-propylbenzofuran-6-yloxy)propylamino)-3-chlorophenylacetic acid;

4-(4-(3-Phenyl-7-prop-2-enylbenzofuran-6-yloxy)butyloxy)-3-chlorophenylacetic acid;

4-(3-(3-Phenyl-7-propylbenzofuran-6-yloxy)propylamino)-phenoxyacetic acid;

3-(3-(3-Phenyl-7-butylbenzofuran-6-yloxy)propylthio)-phenylpropan-3-oic acid;

4-(3-(3-Phenyl-7-butylbenzofuran-6-yloxy)propylthio)-phenylpropan-3-oic acid;

4-(3-(3-Phenyl-7-propylbenzofuran-6-yloxy)propyloxy)-2-phenyl-2,2-dimethylacetic acid;

4-(4-(3-Phenyl-7-(cyclopropylmethyl)benzofuran-6-yloxy)butylamino)-phenoxy-2,2-dimethylacetic acid;

3-(3-(3-Neopentyl-7-propylbenzofuran-6-yloxy)propylthio)-3-methylphenylacetic acid;

4-(3-(3-(2-Phenyl-2,2-dimethyl)-7-propylbenzofuran-6-yloxy)propyloxy)-3-butylphenylacetic acid;

4-(3-(3-Chloro-7-propylbenzofuran-6-yloxy)propylamino)-2-propylphenylacetic acid;

3-(3-(3-Chloro-7-propylbenzofuran-6-yloxy)propylamino)-2-propylphenylacetic acid;

4-(4-(3-Butoxy-7-propylbenzofuran-6-yloxy)butylthio)-2-fluorophenylacetic acid;

4-(3-(3-Phenyl-7-propylbenzofuran-6-yloxy)propylamino)-phenoxyacetic acid;

3-(3-(3-(3-Butylphenyl)-7-butylbenzofuran-6-yloxy)propylthio)-phenylpropan-3-oic acid;

4-(3-(3-(2-Tolyl)-7-butylbenzofuran-6-yloxy)propylthio)-phenylpropan-3-oic acid;

4-(3-(3-(4-Fluorophenyl)-7-propylbenzofuran-6-yloxy)propyloxy)-2-phenyl-2,2-dimethylacetic acid;

4-(3-(3-Phenyl-7-propylbenzofuran-6-yloxy)propyloxy)-phenoxy-2-spiro-cyclopropylacetic acid;

3-(3-(3-Phenyl-7-propylbenzofuran-6-yloxy)propyloxy)-phenoxy-2-spiro-cyclopropylacetic acid;

5-(4-(3-(3-Phenyl-7-propylbenzothiophen-6-yloxy)propylamino)phenyl-2-(2,2-dimethyl)-ethyl)-tetrazole;

5-(4-(3-(3-Phenyl-7-propylbenzofuran-6-yloxy)propyloxy) phenyl-3-propyl)-tetrazole;
5-(4-(4-(3-Phenyl-7-propylindol-6-yloxy)butylamino) phenyl-3-propyl)-tetrazole;
5-(3-(3-(3-Phenyl-7-propylbenzofuran-6-yloxy)propylthio) phenoxy-2-ethyl)-tetrazole; and
5-(4-(3-(3-Phenyl-7-propylbenzofuran-6-yloxy)propylthio) phenoxy-2-ethyl)-tetrazole.

Preferred examples of the compounds of the instant invention are:
Methyl 3-chloro-4-(3-(4-ethyl-8-propyl-7 coumarinoxy) propylthio)phenyl-acetate;
3-Chloro-4-(3-(4-ethyl-8-propyl-7-coumarinoxy) propylthio) phenylacetic acid;
Methyl 3-chloro-4-(3-(3-ethyl-8-propyl-7-coumarinoxy) propylthio) phenyl-acetate;
3-Chloro-4-(3-(3-ethyl-8-propyl-7-coumarinoxy) propylthio) phenylacetic acid;
3-chloro-4-(3-(4-propyl-N-(4-chlorophenyl)-5-indoleoxy) propylthio)phenylacetic acid;
1-(3-chloro-4-(3-(3-phenyl-7-propylbenzofuran-6-oxy) propyl)thiophenyl-1-cyclopropane carboxylic acid;
3-chloro-4-(3-(3-phenyl-7-propylbenzofuran-6-yloxy) propylthio)-phenylacetic acid;
Methyl 3-chloro-4-(3-(3-phenyl-7-propylbenzofuran-6-yloxy)propylthio)-phenylacetate;
4-(3-(3-Phenyl-7-propylbenzofuran-6-yloxy)propyloxy)-phenylacetic acid;
4-(3-(3-Phenyl-7-propylbenzothiophen-6-yloxy)propyloxy)-phenylacetic acid;
3-(4-(3-Phenyl-7-propylbenzofuran-6-yloxy)butyloxy)-phenylacetic acid;
3-(4-(3-Phenyl-7-propylindol-6-yloxy)butyloxy)-phenylacetic acid;
4-(3-(3-Phenyl-7-propylbenzofuran-6-yloxy)propyloxy)-phenoxyacetic acid;
4-(3-(3-Phenyl-7-propylbenzothiophen-6-yloxy)propyloxy)-phenoxyacetic acid;
4-(3-(3-Phenyl-7-propylbenzofuran-6-yloxy)propylthio)-3-propylphenylacetic acid;
4-(4-(3-Phenyl-7-propylindol-6-yloxy)butylthio)-3-chlorophenylacetic acid;
4-(4-(1-Phenyl-4-propylindol-5-yloxy)butylthio)-3-chlorophenylacetic acid;
4-(3-(3-Phenyl-7-propylbenzofuran-6-yloxy)propylsulfono)-3-propylphenylacetic acid;
4-(3-(3-Phenyl-7-propylbenzothiophen-6-yloxy)propylsulfono)-3-chlorophenylacetic acid;
4-(4-(3-Phenyl-7-propylbenzofuran-6-yloxy)butylthio)-3-propylbenzyl-tetrazole;
4-(4-(3-Phenyl-7-propylindol-6-yloxy)butylthio)-3-chlorobenzyl-tetrazole;
4-(4-(1-Phenyl-4-propylindol-5-yloxy)butylthio)-3-chlorobenzyl-tetrazole;
4-(3-(3-Phenyl-7-propylbenzofuran-6-yloxy)propylamino)-phenylacetic acid;
4-(3-(3-Phenyl-7-propylbenzothiophen-6-yloxy) propylamino)-phenylacetic acid;
3-(4-(4-(3-Phenyl-7-propylbenzofuran-6-yloxy)butyloxy)-phenylacetic acid;
3-(4-(4-(3-Phenyl-7-propylindol-6-yloxy)butyloxy)-phenylacetic acid;
3-Chloro-4-((1- propyl-2-dibenzoxyfuran)-propylthio)-phenylacetic acid;
3-chloro-4-(4-(4-trifluoromethyl-8-propyl-coumarinolyl-7-oxy)butyloxy)phenylacetic acid;
3-Propyl-4-(3-(4-tert-butylmethyl-8-propyl-coumarinolyl-7-oxy)-propylthio)phenylacetic acid; and
2-methyl-2-(3-chloro-4-(3-(3phenyl-7-propylbenzofuran-6-oxy)propyl)thio)phenyl propionic acid.

The compounds of the present invention may have asymmetric centers and occur as racemates, racemic mixtures, and as individual diastereomers, with all possible isomers, including optical isomers, being included in the present invention.

Compounds of the general Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I may be obtained by stereospecific synthesis using optically pure starting materials of known configuration.

The instant compounds can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

As previously indicated, the compounds of the present invention have valuable pharmacological properties. They are useful in treating or preventing diabetes, treating obesity, lowering triglyceride levels and prevention of vascular restenosis. They are useful in treating other disorders where insulin resistance is a component including ovarian hyperandrogenism (polycyctic ovarian syndrome). They are also useful in raising high density lipoprotein levels, preventing, halting or slowing the progression of atherosclerotic cardiovascular diseases and related conditions and disease events.

The present invention also provides a compound of the general Formula I or a pharmaceutically acceptable salt thereof for use as an active therapeutic substance.

The present invention further provides a compound of the general Formula I, or a pharmaceutically acceptable ester thereof; or pharmaceutically acceptable salt thereof, for use in the treatment of hyperglycemia (diabetes) in human or non-human animals.

The present invention further provides a compound of the general Formula I, or a pharmaceutically acceptable ester thereof; or pharmaceutically acceptable salt thereof, in combination with known sulfonylureas, other insulin secretogogues as well as insulin for use in the treatment of diabetes treating obesity, lowering triglyceride levels, prevention of vascular restenosis, treating other disorders where insulin resistance is a component including ovarian hyperandrogenism (polycyctic ovarian syndrome), raising high density lipoprotein levels, and preventing, halting or slowing the progression of atherosclerotic cardiovascular diseases and related conditions and disease events and hypertension in human or non-human animals.

In one aspect, the present invention provides a compound of the general Formula I for use in the treatment of obesity in human or non-human animals. Said compound can be effectively used in combination with other known or proposed strategies for the treatment of obesity or obesity-related disorders; for example, fenfluramine, dexfenfluramine, phentiramine and $\beta_3$ adrenergic receptor agonist agents.

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies. The instant compounds can be effectively used in combination with known therapies for diabetes including insulin, sulfonylureas, biguanides (such as metformin), $\alpha$-glucosidase inhibitors (such as acarbose) and others.

Two major forms of diabetes mellitus are now recognized. Type I diabetes, or insulin-dependent diabetes, is the result of an absolute deficiency of insulin, the hormone which regulates glucose utilization. Type II diabetes, or non-insulin-independent diabetes, often occurs in the face of normal, or even elevated levels of insulin and appears to be the result of the inability of tissues to respond appropriately to insulin. Most of the Type II diabetics are also obese. Accordingly, in another aspect the present invention provides a method of lowering triglyceride levels which comprises administering, to an animal in need thereof, a therapeutically effective amount of a compound of the formula I or pharmaceutically acceptable salt or ester thereof.

In addition the compounds of the present invention lower or modulate triglyceride levels and/or cholesterol levels and raise HDL plasma levels and are therefore of use in combating medical conditions wherein such lowering (and raising) is thought to be beneficial. Thus they may be used in the treatment of hypertension, obesity, atherosclerotic disease events, diabetes and related conditions by administering to an animal in need thereof, a therapeutically effective amount of a compound of the formula (I) or pharmaceutically acceptable salt thereof. The compositions are formulated and administered in the same general manner as detailed below. They may also contain other active ingredients known for use in the treatment of atherosclerotic disease events, diabetes, hypertension, obesity and related conditions, for example fibrates such as clofibrate, bezafibrate and gemfibrozil; inhibitors of cholesterol biosynthesis such as HMG-CoA reductase inhibitors for example lovastatin, simvastatin and pravastatin; inhibitors of cholesterol absorption for example beta-sitosterol and (acyl CoA-:cholesterol acyltransferase) inhibitors for example melinamide; anion exchange resins for example cholestyramine, colestipol or a dialkylaminoalkyl derivatives of a cross-linked dextran; nicotinyl alcohol, nicotinic acid or a salt thereof; vitamin E; and thyromimetics.

In particular the invention provides methods for preventing or reducing the risk of developing atherosclerosis, comprising the administration of a prophylactically effective amount of a compound of formula I alone or in combination with one or more additional pharmaceutically active agents, to a mammal, particularly human, who is at risk of developing atherosclerosis.

Atherosclerosis encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease."

The instant invention further provides methods for preventing or reducing the risk of a first or subsequent (where the potential exists for recurrence) atherosclerotic disease event, comprising the administration of a prophylactically effective amount, or more particularly an HDL-raising amount, of a compound of formula I alone or in combination with one or more additional pharmaceutically active agents, to a mammal, particularly human, who is at risk for having an atherosclerotic disease event. The term "atherosclerotic disease event" as used herein is intended to encompass coronary heart disease events, cerebrovascular events, and intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. It is intended that persons who have previously experienced one or more non-fatal atherosclerotic disease event are those for whom the potential for recurrence of such an event exists.

Persons to be treated with the instant therapy include those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein cholesterol, high levels of low density lipoprotein cholesterol, and a family history of atherosclerotic cardiovascular disease. Published guidelines for determining those who are at risk of developing atherosclerotic disease can be found in: National Cholesterol Education Program, Second report of the Expert Panel on *Detection, Evaluation, and Treatment of High Blood Cholesterol in Adults (Adult Treatment Panel II)*, National Institute of Health, National Heart Lung and Blood Institute, NIH Publication No. 93-3095, September 1993; abbreviated version: Expert Panel on Detection, Evaluation, and Treatment of High Blood Cholesterol in Adults, *Summary of the second report of the national cholesterol education program (NCEP) Expert Panel on Detection, Evaluation, and Treatment of High Blood Cholesterol in Adults (Adult Treatment Panel II)*, JAMA, 1993, 269, pp. 3015–23. People identified as having one or more of the above-noted risk factors, as well as people who already have atherosclerosis, are intended to be included within the group of people considered to be at risk for having an atherosclerotic disease event.

The active compounds of the present invention may be orally administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The effective dosage of active ingredient employed may vary depending on the particular compound employed, the mode of administration, the condition being treated and the severity of the condition being treated.

When treating or preventing diabetes mellitus and/or hyperglycemia or hypertriglyceridemia, or obesity, or when treating, preventing or slowing the progression of atherosclerosis generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

The compositions are formulated and administered in the same general manner as detailed below. The compounds of the instant invention may be used effectively alone or in combination with one or more additional active agents depending on the desired target therapy. Combination therapy includes administration of a single pharmaceutical dosage formulation which contains a compound of formula I and one or more additional active agents, as well as administration of a compound of formula I and each active agent in its own separate pharmaceutical dosage formulation. For example, a compound of formula I and an HMG-CoA reductase inhibitor can be administered to the patient together in a single oral dosage composition such as a tablet or capsule, or each agent administered in separate oral dosage formulations. Where separate dosage formulations are used, a compound of formula I and one or more additional active agents can be administered at essentially the same time, i.e., concurrently, or at separately staggered times, i.e, sequentially; combination therapy is understood to include all these regimens.

An example of combination treatment or prevention of atherosclerosis may be wherein a compound of formula I is administered in combination with one or more of the following active agents: an antihyperlipidemic agent; a plasma HDL-raising agent; an antihypercholesterolemic agent such as a cholesterol biosynthesis inhibitor, for example an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A: cholesterol acyltransferase (ACAT) inhibitor such as melinamide; probucol; nicotinic acid and the salts thereof and niacinamide; a cholesterol absorption inhibitor such as beta-sitosterol; a bile acid sequestrant anion exchange resin such as cholestyramine, colestipol or dialkylaminoalkyl derivatives of a cross-linked dextran; an LDL (low density lipoprotein) receptor inducer; fibrates such as clofibrate, bezafibrate, fenofibrate, and gemfibrizol; vitamin $B_6$ (also known as pyridoxine) and the pharmaceutically acceptable salts thereof such as the HCl salt; vitamin $B_{12}$ (also known as cyanocobalamin); antioxidant vitamins such as vitamin C and E and beta carotene; a beta-blocker; an angiotensin II antagonist; an angiotensin converting enzyme inhibitor; and a platelet aggregation inhibitor such as fibrinogen receptor antagonists (i.e., glycoprotein IIb/IIIa fibrinogen receptor antagonists) and aspirin. As noted above, the compounds of formula I can be administered in combination with more than one additional active agent, for example, a combination of a compound of formula I with an HMG-CoA reductase inhibitor (e.g. lovastatin, simvastatin and pravastatin) and aspirin, or a compound of formula I with an HMG-CoA reductase inhibitor and a beta blocker.

Another example of combination therapy can be seen in treating obesity or obesity-related disorders, wherein the compounds of formula I may be effectively used in combination with for example, fenfluramine, dexfenfluramine, phentiramine and $\beta_3$ adrenergic receptor agonist agents.

Still another example of combination therapy can be seen in treating diabetes and related disorders wherein the compounds of formula I can be effectively used in combination with for example sulfonylureas, biguanides, α-glucosidase inhibitors, other insulin secretogogues, insulin as well as the active agents discussed above for treating atherosclerosis.

In accordance with this invention, a pharmaceutically effective amount of a compound of formula I can be used for the preparation of a medicament useful for treating diabetes, treating obesity, lowering triglyceride levels, raising the plasma level of high density lipoprotein, and for treating, preventing or reducing the risk of developing atherosclerosis, and for preventing or reducing the risk of having a first or subsequent atherosclerotic disease event in mammals, particularly in humans.

Additionally, an effective amount of a compound of formula I and a therapeutically effective amount of one or more active agents selected from the group consisting of: an antihyperlipidemic agent; a plasma HDL-raising agent; an antihypercholesterolemic agent such as a cholesterol biosynthesis inhibitor, for example an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A: cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate, and gemfibrozil; vitamin $B_6$ and the pharmaceutically acceptable salts thereof; vitamin $B_{12}$; an antioxidant vitamin; a beta-blocker; an angiotensin II antagonist; an angiotensin converting enzyme inhibitor; a platelet aggregation inhibitor; a fibrinogen receptor antagonist; aspirin; fenfluramines, dexfenfluramines, phentiramines, $\beta_3$ adrenergic receptor agonists; sulfonylureas, biguanides, α-glucosidase inhibitors, other insulin secretogogues, and insulin can be used together for the preparation of a medicament useful for the above-described treatments.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Specific examples of formula I may require the use of protecting groups to enable their successful elaboration into the desired structure. Protecting groups may be chosen with reference to Greene, T. W., et al., *Protective Groups in Organic Synthesis*, John Wiley & Sons, Inc., 1991. The blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: trimethylsilyl, triethylsilyl, o-nitrobenzyloxycarbonyl, p-nitrobenzyloxycarbonyl, t-butyldiphenylsilyl, t-butyldimethylsilyl, benzyloxycarbonyl, t-butyloxycarbonyl, 2,2,2-trichloroethyloxycarbonyl, and allyloxycarbonyl. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl.

The process for making the compounds of the instant invention is generally depicted in Scheme 1 below:

SCHEME 1

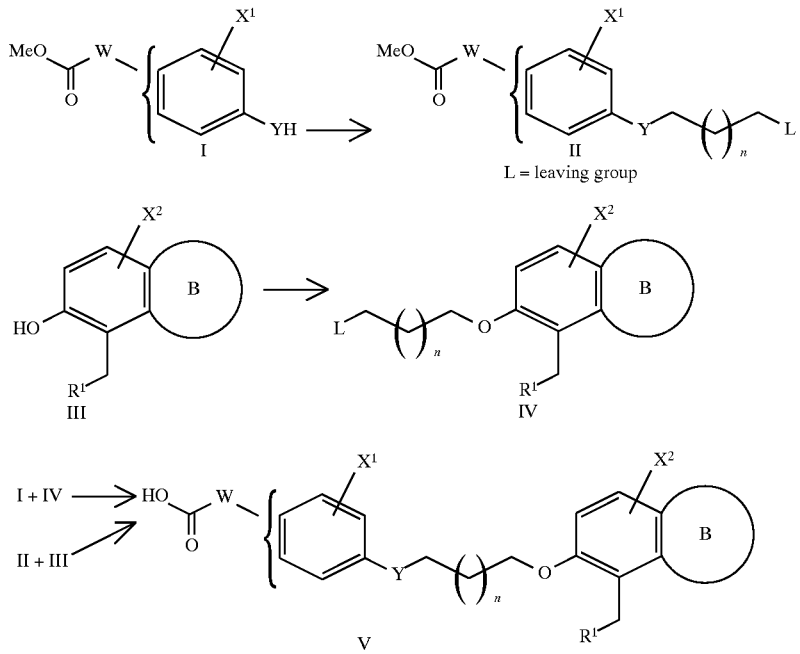

L is a leaving group such as halo, preferably bromide, or sulfonyloxy, preferably mesyloxy or tosyloxy.

The following examples are provided so that the invention might be more fully understood. They should not be construed as limiting the invention in any way.

EXAMPLE 1

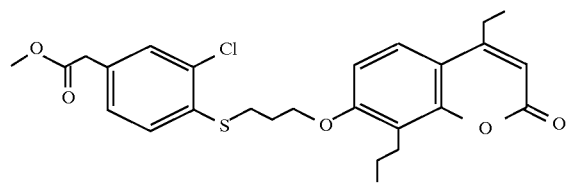

Methyl 3-chloro-4-(3-(4-ethyl-8-propyl-7-coumarinyloxy)propylthio) phenyl-acetate Step A: Preparation of 4-tert-butyldimethylsilyloxy-2-hydroxy-3-propylpropiophenone To a solution of 2,4-dihydroxy-3-propylpropiophenone (2.0 g, 9.6 mmol) and imidazole (1.31 g, 19.2 mmol) in 15 mL dimethylformamide (DMF) was added tert-butyldimethylsilyl chloride (1.74 g, 11.5 mmol) in portions. The mixture was stirred at ambient temperature for one hour wherein it was partioned between saturated (aqueous) ammonium chloride and ethyl acetate. After separation of the layers, lay aqueous phase was extracted with ethyl acetate. The organic layers were combined and dried over magnesium sulfate, filtered, concentrated in vacuo, and the crude residue was purified by flash chromatography on silica gel (gradient elution: 5% then 10% ethyl acetate/hexane) to provide the title compound.

$^1$H NMR (400 MHz, CDCl$_3$, ppm): δ0.242 (s, 3H), 0.244 (s, 3H), 0.93 (t, J=7.1 Hz, 3H), 0.99 (s, 9H), 1.20 (t, J=7.3 Hz, 3H), 1.45–1.55 (m, 2H), 2.56–2.60 (m, 2H), 2.93 (q, J=7.3 Hz, 2H), 6.32 (d, J=8.9 Hz, 1H), 7.49 (d, J=8.9 Hz, 1H).

Step B: Preparation of 7-tert-butyldimethylsilyloxy-4-ethyl-8-propylcoumarin 4-tert-butyldimethylsilyloxy-2-hydroxy-3-propylpropiophenone (Step A; 500 mg, 1.5503 mmol) was combined with methyl (triphenyl-phosphoranylidene) acetate (1551 mg, 4.6508 mmol) in benzene (5 mL) and heated to 95° C. in a sealed tube for 15 hours. The reaction was cooled and the product was purified by flash chromatography on silica gel (gradient elution: 5% then 10% then 15% ethyl acetate/hexane) to provide the title compound.

$^1$H NMR (400 MHz, CDCl$_3$, ppm): δ0.24 (s, 6H), 0.96 (t, J=7.3 Hz, 3 H), 1.01 (s, 9H), 1.29 (t, J=7.4 Hz, 3H), 1.55–1.65 (m, 2H), 2.70–2.82 (m, 4H), 6.13 (s, 1H), 6.74 (d, J=8.7 Hz, 1H), 7.33 (d, J=8.7 Hz, 1H).

Step C: Preparation of 4-ethyl-7-hydroxy-8-propylcoumarin

To a solution of 7-tert-butyldimethylsilyloxy-4-ethyl-8-propylcoumarin (Step B; 117 mg, 0.3382 mmol) in five mL of tetrahydrofuran (THF) was added a 1.0M solution of tetrabutylammonium fluoride (0.51 mL, 0.51 mmol). The mixture was stirred at ambient temperature for five minutes and subsequently quenched by the addition of saturated ammonium chloride. The mixture was extracted several times with ethyl acetate and the combined organic extracts were dried over magnesium sulfate, filtered, concentrated in vacuo, and the crude residue was purified by flash chromatography on silica gel (gradient elution: 10% then 20% then 30% ethyl acetate/hexane) which yielded the title compound.

$^1$H NMR (400 MHz, CDCl$_3$, ppm): δ0.98 (t, J=7.0 Hz, 3H), 1.30 (t, J=7.0 Hz, 3H), 1.55–1.70 (m, 2H), 2.70–2.85 (m, 4H), 6.15 (s, 1H), 6.74 (d, J=8.7 Hz, 1H), 7.33 (d, J=8.7 Hz, 1H).

Step D: Preparation 7-(3-bromopropoxy)-4-ethyl-8-propylcoumarin.

To a solution of 4-ethyl-7-hydroxy-8-propylcoumarin (Step C; 95 mg, 0.4086 mmol) and potassium carbonate (112.9 mg, 0.8171 mmol) in 2.0 mL of DMF was added 1,3-dibromopropane (0.21 mL, 2.043 mmol). The mixture was stirred at ambient temperature for three hours and quenched with saturated (aqueous) ammonium chloride and extracted with ethyl acetate. The combined organic extracts were washed with brine, filtered, concentrated in vacuo, and the crude residue was purified by flash chromatography on silica gel (gradient elution: 20% then 30% ethyl acetate/hexane). This provided the title compound.

$^1$H NMR (400 MHz, CDCl$_3$, ppm): δ0.94 (t, J=7.3 Hz, 3H), 1.30 (t, J=7.5 Hz, 3H), 1.50–1.65 (m, 2H), 2.30–2.40 (m, 2H), 2.72–2.85 (m, 4 H), 3.62 (t, J=6.0 Hz, 2H), 4.19 (t, J=6.0 Hz, 2H), 6.15 (s, 1H), 6.84 (d, J=8.9 Hz, 1H), 7.44 (d, J=8.9 Hz, 1H).

Step E: Preparation of methyl 3-chloro-4-(3-(4-ethyl-8-propyl-7-coumarinyloxy)propylthio)phenylacetate To a solution of 3-chloro-4-dimethylcarbamoylthiophenylacetic acid methyl ester (129 mg, 0.3991 mmol) in 0.75 mL methanol was added a 0.5M solution of sodium methoxide in methanol. This mixture was heated to 70° C. for 90 minutes. After cooling to ambient temperature, a solution of 7-(3-bromopropoxy)-4-ethyl-8-propylcoumarin (Step D) in 1.2 mL methanol was added dropwise. The mixture was heated to 70° C. for 16 hours. The reaction mixture was concentrated in vacuo and diluted with ethyl acetate. The organic mixture was washed with water, brine, dried over magnesium sulfate, filtered, and concentrated in vacuo. The crude residue was purified by flash chromatography on silica gel (20% ethyl acetate/hexane) to provide the title compound.

$^1$H NMR (400 MHz, CDCl$_3$, ppm): δ3.55 (s, 2H), 3.68 (s, 3H).

EXAMPLE 2

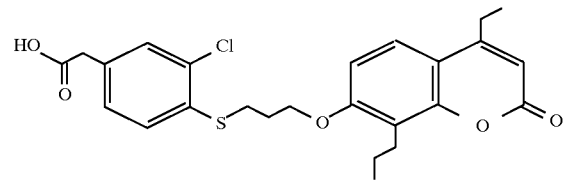

3-Chloro-4-(3-(4-ethyl-8-propyl-7-coumarinyloxy) propylthio) phenylacetic acid

To a solution of methyl 3-chloro-4-(3-(4-ethyl-8-propyl-7-coumarinoxy)propylthio)phenylacetate (Example 1; 82 mg, 0.1677 mmol) in 1.2 mL methanol:water (1:1) was added a 0.5M solution of potassium hydroxide in methanol. The mixture was heated to 40° C. for two hours at which time the mixture was acidified to pH=3 with 1M aqueous hydrochloric acid. The aqueous solution was extracted with ethyl acetate and the combined organics were dried over magnesium sulfate, filtered, and the crude residue was purified by flash chromatography on silica gel (30% ethyl acetate/hexane/1% acetic acid) which provided the title compound.

$^1$H NMR (400 MHz, CD$_3$OD, ppm): δ0.95 (t, J=7.4 Hz, 3H), 1.32 (t, J=7.4 Hz, 3H), 1.59 (q, J=7.5 Hz, 2H), 2.15–2.25 (m, 2H), 2.80–2.90 (m, 4H), 3.20 (t, J=7.1 Hz, 2H), 3.55 (s, 2H), 4.24 (t, J=5.8 Hz, 2H), 6.16 (s, 1H), 7.02 (d, J=8.9 Hz, 1H), 7.17 (dd, J=1.9, 8.1 Hz, 1H), 7.34 (d, J=1.9 Hz, 1H), 7.38 (d, J=8.1 Hz, 1H), 7.64 (d, J=8.9 Hz, 1H).

EXAMPLE 3

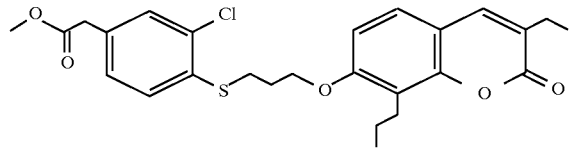

Methyl 3-chloro-4-(3-(3-ethyl-8-propyl-7-coumarinyloxy)propylthio) phenyl-acetate Step A: Preparation of 4-(3-propenyloxy)-2-hydroxybenzaldehyde To a solution of 2,4-dihydroxybenzaldehyde (2.0 g, 14.5 mmol) in 20 mL DMF was added allyl bromide (1.92 g, 15.9 mmol). The mixture was stirred at ambient temperature for several hours at which time it was partioned between water and ethyl acetate. After the layers were separated, the aqueous layer was extracted with ethyl acetate. The combined organic extracts were washed with brine, dried over magnesium sulfate, concentrated in vacuo, and the residue was purified by flash chromatography on silica gel (30% ethyl acetate/hexane). This provided the title compound.

¹H NMR (400 MHz, CDCl₃, ppm): δ4.55–4.60 (m, 2H), 5.29–5.45 (m, 2H), 5.95–6.20 (m, 1H), 6.40–6.60 (m, 2H), 7.38–7.45 (m, 1H), 9.70 (s, 1H).

Step B: Preparation of 7-butyroyloxy-3-ethyl-8-(2-propenyl)coumarin 4-(3-propenyloxy)-2-hydroxybenzaldehyde (Step A; 200 mg, 1.12 mmol) was combined with butyric anhydride (344 mg, 2.25 mmol) and sodium butyrate (246 mg, 2.25 mmol) and heated in a sealed tube at 190° C. for 14 hours. The reaction was cooled to ambient temperature and diluted with ethyl acetate. The organic mixture was washed with water, brine, dried over magnesium sulfate, and the crude residue was purified by flash chromatography on silica gel (gradient elution: 10% then 20% then 30% ethyl acetate/hexane). This provided the title compound.

¹H NMR (400 MHz, CDCl₃, ppm): δ0.96 (t, J=7.5 Hz, 3H), 1.24 (t, J=7.3 Hz, 3H), 1.60–1.75 (m, 2H), 2.23 (t, J=7.5 Hz, 2H), 2.55 (q, J=7.3 Hz, 2H), 3.60–3.70 (m, 2H), 5.10–5.20 (m, 2H), 5.90–6.05 (m, 1 H), 6.77 (d, J=8.4 Hz, 1H), 7.20 (d, J=8.4 Hz, 1H), 7.40 (s, 1H).

Step C: Preparation of 3-ethyl-7-hydroxy-8-propylcoumarin

7-Butyroyloxy-3-ethyl-8-(2-propenyl)coumarin (Step B; 95 mg) dissolved in methanol was reacted with 10% Pd/C under an atmosphere of hydrogen gas for several hours. The crude mixture was loaded directly onto a flash column containing silica gel and eluted with 20% ethyl acetate/hexane. This provided the title compound.

¹H NMR (400 MHz, CDCl₃, ppm): δ0.96 (t, J=7.5 Hz, 3H), 1.15–1.25 (m, 3H), 1.50–1.70 (m, 3H), 2.55 (q, J=7.3 Hz, 2H), 2.75–2.85 (m, 2H), 6.77 (d, J=8.4 Hz, 1H), 7.15 (d, J=8.4 Hz, 1H), 7.38 (s, 1H).

Step D: Preparation of 7-(3-bromopropyl)oxy-3-ethyl-8-propylcoumarin

To a solution of 3-ethyl-7-hydroxy-8-propylcoumarin (37 mg, 0.1593 mmol) and potassium carbonate (44 mg, 0.3186 mmol) in 0.7 mL DMF was added 1,3-dibromopropane (161 mg, 0.08 mL). The mixture was stirred at ambient temperature for 2 hours and diluted with ethyl acetate and saturated (aqueous) ammonium chloride. After the layers were separated, the aqueous phase was extracted with ethyl acetate. The combined organic extracts were washed with brine, dried over magnesium sulfate, filtered, concentrated in vacuo, and the crude residue was purified by flash chromatography on silica gel (gradient elution: 5% then 10% then 20% ethyl acetate/hexane). This provided the title compound.

Step E: Preparation of methyl 3-chloro-4-(3-(3-ethyl-8-propyl-7-coumarinyloxy)propylthio)phenylacetate To a solution of 3-chloro-4-dimethylcarbamoylthiophenylacetic acid methyl ester (54 mg, 0.1656 mmol) in 0.50 mL methanol was added a 0.5M solution of sodium methoxide (0.33 mL, 0.1656 mmol) in methanol. This mixture was heated to 70° C. for 90 minutes. After cooling to ambient temperature, a solution of 7-(3-bromopropoxy)-3-ethyl-8-propylcoumarin (Step D; 54 mg, 0.1656 mmol) in 1.2 mL methanol was added dropwise. The mixture was heated to 70° C. for several hours. The reaction mixture was concentrated in vacuo and diluted with ethyl acetate. The organic mixture was washed with water, brine, dried over magnesium sulfate, filtered, and concentrated in vacuo. The crude residue was purified by flash chromatography on silica gel (20% ethyl acetate/hexane) to provide the title compound.

¹H NMR (400 MHz, CDCl₃, ppm): δ0.93 (t, J=7.4 Hz, 3H), 1.22 (t, J=7.5 Hz, 3H), 1.50–1.62 (m, 2H), 2.15–2.30 (m, 2H), 2.55 (q, J=7.5 Hz, 2H), 2.82 (t, 7.6 Hz, 2H), 3.15 (t, J=7.1 Hz, 2H), 3.55 (s, 2H), 3.68 (s, 3H), 4.15 (t, J=5.7 Hz, 2H), 6.77 (d, J=8.7 Hz, 1H), 7.11 (dd, J=1.7, 8.1 Hz, 1H), 7.21 (d, J=8.7 Hz, 1H), 7.26 (d, J=8.1 Hz, 1H), 7.30 (d, J=1.7 Hz, 1H), 7.38 (s, 1H).

EXAMPLE 4

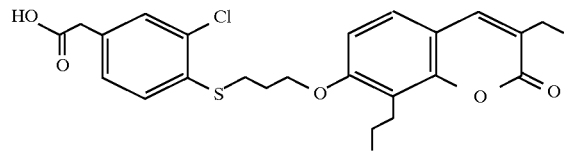

3-Chloro-4-(3-(3-ethyl-8-propyl-7-coumarinyloxy) propylthio) phenylacetic acid

To a solution of methyl 3-chloro-4-(3-ethyl-8-propyl-7-coumarinoxy)propylthio)phenylacetate (Example 3; 30 mg, 0.0613 mmol) 1.0 mL methanol:water (2:1) was added a 0.5M solution of potassium hydroxide in methanol (0.61 mL, 0.3061 mmol). The mixture was heated to 30° C. for two hours at which time the mixture was acidified to pH=3 with 1M hydrochloric acid. The aqueous solution was extracted with ethyl acetate and the combined organics were dried over magnesium sulfate, filtered, and the crude residue was purified by flash chromatography on silica gel (30% ethyl acetate/hexane/1% acetic acid) which provided the title compound ¹H NMR (400 MHz, CD₃OD, ppm): δ0.95 (t, J=7.4 Hz, 3H), 1.23 (t, J=7.5 Hz, 3H), 1.55–1.65 (m, 2H), 2.10–2.25 (m, 2H), 2.53 (q, J=7.5 Hz, 2H), 2.83 (t, J=7.5 Hz, 2H), 3.20 (t, J=7.1 Hz, 2H), 3.53 (s, 2H), 4.22 (t, J=5.8 Hz, 2H), 6.96 (d, J=8.7 Hz, 1H), 7.18 (dd, J=1.8, 8.0 Hz, 1H), 7.30–7.41 (m, 3H), 7.67 (s, 1H).

EXAMPLE 5

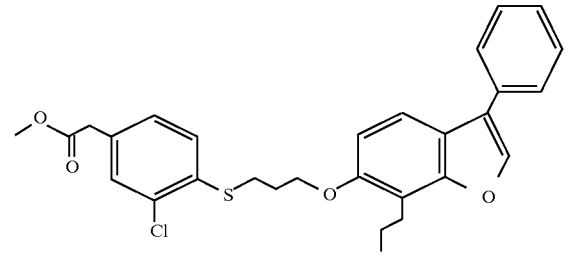

Methyl 3-chloro-4-(3-(3-phenyl-7-propylbenzofuran-6-yloxy)propylthio)-phenylacetate Step A: Preparation of 2-propyl-3-(2-phenyl-2-oxoethoxy)phenol To a solution of 2-propyl resorcinol (178.27 g; 1.171 mol) in dry DMF (1200 mL) was added cesium carbonate (104.95 g; 322.12 mmol). The mixture was stirred at room temperature and treated dropwise with a solution of 2-bromoacetophenone (58.29 G; 292.84 mmol) in dry DMF (500 mL) over 2 hours. The was stirred at ambient temperature for 64 hours. The reaction mixture was partitioned between isopropyl acetate and water. The aqueous was adjusted to pH 13 by addition of aq. 5N sodium hydroxide. The organic was dried over magnesium sulfate, filtered and evaporated to a residue. The residue was dissolved in methylene chloride (110 mL) and hexane (350 mL) and heated to reflux. The solution was cooled to −10° C. Stirring was continued for 1 hour. The title compound was recovered by filtration.

21

¹H NMR(400 MHz, CDCl₃): δ8.00 (dd, J=7.3, 1.3 Hz, 2H), 7.59 (t, J=7.2, 1.4 Hz, 1H), 7.49 (dt, J=7.6, 1.5 Hz, 2H), 6.98 (t, J=8.2 Hz, 1H), 6.47 (d, J=8.1 Hz, 1H), 6.38 (d, J=8.2 Hz, 1H), 4.75 (s, very broad, 1H), 2.66 (t, J=7.7 Hz, 2H), 1.57 (hex, J=7.5 Hz, 2H), 0.94 (t, J=7.4 Hz, 3H).

Step B: Preparation of 3-phenyl-6-hydroxy-7-propylbenzofuran

To a stirred suspension of 2-propyl-3-(2-phenyl-2-oxoethoxy)phenol (9.30 g) in o-phosphoric acid(85%) (93 mL) at room temperature was added over a 45 minutes period phosphorus pentoxide(46.50 g). During this period the reaction mixture was heated several times with a heat gun. After stirring the mixture for 30 minutes the reaction was checked by TLC(to take a little of sample with a capillary and dissolve sample in water and add several drops of ether; elution: 50% methylene chloride in hexane). The reaction mixture was heated again with heat gun if the reaction was not complete. The reaction mixture continued to be stirred for 20 minutes, then was poured into a beaker containing ice. The reaction flask was then rinsed with water and ether, and the washings were added to the beaker. The organic layer was separated, washed with water, dried over MgSO4, and concentrated. Column Chromatography (silica gel 60, 50% methylene chloride in hexane) gave the title compound.

¹H NMR (400 MHz, CDCl₃): δ7.71 (s, 1H), 7.64 (dd, J=7.0, 1.4 Hz, 2H), 7.51 (d, J=8.5 Hz, 1H), 7.46 (dt, J=7.3, 1.8 Hz, 2H), 7.35 (dt, J=7.2, 1.3 Hz, 1H), 6.82 (d, J=8.4 Hz, 1H), 4.74 (s, very broad, 1H), 2.90 (t, J=7.7 Hz, 2H), 1.75 (hex, J=7.5 Hz, 2H), 1.03 (t, J=7.4 Hz, 3H).

Step C: Preparation of 3-phenyl-6-(3-bromopropyloxy)-7-propylbenzofuran

To a solution of 3-phenyl-6-hydroxy-7-propylbenzofuran (3.54 g, 13.99 mmol) and potassium carbonate (2.08 g, 15.05 mmol) in dry methyl ethyl ketone (50 ml) was added 1,3-dibromopropane (2.84 ml, 27.98 mmol). The reaction mixture refluxed for 5 hours under nitrogen. The mixture was partitioned between isopropyl acetate and pH4 buffer. The organic was dried over sodium sulfate. The solvent was removed under reduced pressure, and the residue was purified by chromatography (silica gel, 50% methylene chloride in hexane) to afford the title compound.

¹H NMR(400 MHz, CDCl₃): δ7.70 (s, 1H), 7.62 (dd, J=7.0, 1.4 Hz, 1H), 7.56 (d, J=8.6 Hz, 1H), 7.44 (td, J=6.8, 1.6 Hz, 2H), 7.35 (dd, J=7.0, 1.4 Hz, 1H), 6.92 (d, J=8.6 Hz, 1H), 4.16 (t, J=5.8 Hz, 2H), 3.65 (t, J=6.4 Hz, 2H), 2.88 (t, J=6.2 Hz, 2H), 2.36 (quint, J=6.3 Hz, 2H), 1.70 (hex, J=6.1 Hz, 2H), 0.98 (t, J=7.4 Hz, 3H).

Step D: Preparation of Methyl 3-chloro-4-(3-(3-phenyl-7-propylbenzofuran-6-yloxy)propylthio)-phenylacetate To a solution of 3-chloro-4-dimethylcarbomoylthio-benzene-acetic acid, methyl ester (3.88 g, 13.50 mmol) and methanol (40 ml), added 4.37M sodium methoxide(3.35 ml, 14.63 mmol). The reaction mixture was refluxed for 2 hr, was then allowed to cool to 50° C. 3-phenyl-6-(3-bromopropyloxy)-7-propylbenzofuran (4.20 g, 11.25 mmol) was added, and the mixture was stirred at 50° C. for 1.5 hr. The mixture was partitioned between isopropyl acetate and pH4 buffer. The organic was dried over sodium sulfate. The solvent was removed under reduced pressure, and the residue was purified by chromatography (silica gel, 50% methylene chloride in hexane) to afford the title compound.

¹H NMR(400 MHz, CDCl₃): δ7.70 (s, 1H), 7.60 (dd, J=8.3, 1.2 Hz, 2H), 7.53 (d, J=8.3, Hz, 1H), 7.45 (t, J=7.5 Hz, 2H), 7.34 (dd, J=8.4, 1.3 Hz, 1H), 7.28 (m, 2H), 7.11 (dd, J=8.2, 1.7 Hz, 1H), 6.89 (d, J=8.3 Hz, 1H), 4.14 (t, J=5.8 Hz, 2H), 3.69 (s, 3H), 3.55 (s, 2H), 3.17 (t, J=7.0 Hz, 2H),

22

2.89 (t, J=7.4 Hz, 2H), 2.18 (quint, J=7.1 Hz, 2H), 1.71 (hex, J=7.3 Hz, 2H), 0.96 (t, J=7.3 Hz, 3H).

EXAMPLE 6

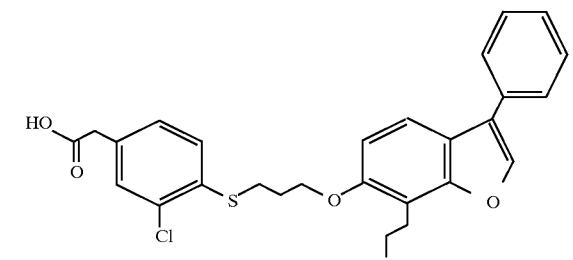

3-chloro-4-(3-(3-phenyl-7-propylbenzofuran-6-yloxy)propylthio)-phenylacetic acid To a solution of methyl 3-chloro-4-(3-(3-phenyl-7-propylbenzofuran-6-yloxy)propylthio)-phenylacetate (3.72 g, 7.31 mmol) prepared in last step and aqueous lithium hydroxide(1.0M; 14.62 ml; 14.62 mmol) in methanol (25 ml) was refluxed for 1 hr. The mixture was partitioned between isopropyl acetate and pH4 buffer. The organic was dried over sodium sulfate. The solvent was removed under reduced pressure, and the residue was purified by chromatography (silica gel, 50% methylene chloride in hexane) to afford the title compound. M.P: 143° C. ESI-MS: m/e-495 (M+1)

¹H NMR(400 MHz, CDCl₃): δ7.7o (s, 1H), 7.61 (dd, J=8.3, 1.2 Hz, 2H), 7.54 (d, J=8.4, Hz, 1H), 7.44 (t, J=7.5 Hz, 2H), 7.35 (dd, J=8.4, 1.3 Hz, 1H), 7.29 (m, 2H), 7.11 (dd, J=8.1, 1.8 Hz, 1H), 6.89 (d, J=8.3 Hz, 1H), 4.15 (t, J=5.8 Hz, 2H), 3.57 (s, 2H), 3.17 (t, J=7.0 Hz, 2H), 2.89 (t, J=7.4 Hz, 2H), 2.18 (quint, J=7.1 Hz, 2H), 1.71 (hex, J=7.3 Hz, 2H), 0.96 (t, J=7.3 Hz, 3H).

EXAMPLE 7

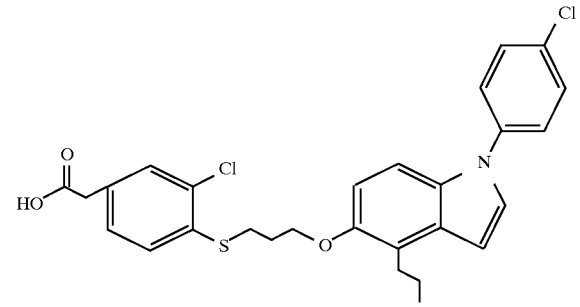

3-chloro-4-(3-(4-propyl-N-(4-chlorophenyl)-5-indoleoxy) propylthio)phenylacetic acid Step A: Preparation of 5-allyloxyindole 5-hydroxyindole (1.00 g, 7.29 mmol) and potassium carbonate (1.38 g, 9.94 mmol) were taken up in 20 mL of dimethylformamide (DMF) and stirred at 60° C. for 0.5 hours. Allyl bromide (0.57 mL, 6.62 mmol) was added and the reaction was stirred for an additional 18 hours then cooled and diluted with ethyl acetate. The organic layer was washed with water, brine, dried over magnesium sulfate, filtered, concentrated in vacuo, and the crude residue was purified by flash chromatography on silica gel (10% ethyl acetate/hexane) to provide the title compound.

¹H NMR (300 MHz, CDCl₃, ppm): δ4.59 (dd, 2H), 5.28 (d, 1H), 5.44 (d, 1H), 6.12 (m, 1H), 6.47 (d, 1H), 6.88 (dd, 1H), 7.16 (dd, 2H), 7.30 (s, 1H), 8.11 (broad s, 1H)

Step B: Preparation of 5-allyloxy-N-(4-chlorophenyl)indole

To a solution of sodium hydride (60%, 254 mg, 6.35 mmol) in 15 mL tetrahydrofuran (THF) was added 5-allyloxyindole (Step A; 1.0 g, 5.77 mmol) in 5 mL THF and the mixture was stirred for 1 hour at ambient temperature. 4-fluorochlorobenzene (0.69 mL, 6.35 mmol) was added and the reaction heated to reflux for 21 hours. After cooling, the reaction was quenched with saturated aqueous ammonium chloride and extracted with ethyl acetate. The organic layer was washed with water, brine, dried over magnesium sulfate, filtered, concentrated in vacuo, and the crude residue purified by flash chromatography on silica gel (15% ethyl acetate/hexane) to provide the title compound.

¹H NMR (300 MHz, CDCl₃, ppm): δ4.60 (dd, 2H), 5.30 (d, 1H), 5.45 (d, 1H), 6.12 (m, 1H), 6.60 (d, 1H), 6.81 (d, 1H), 6.92 (dd, 1H), 7.14–7.32 (m, 2H), 7.37–7.50 (m, 4H)

Step C: Preparation of 4-allyl-5-hydroxy-N-(4-chlorophenyl)indole 5-allyloxy-N-(4-chlorophenyl)indole (Step B; 1.4 g, 4.93 mmol) was refluxed in 20 mL 1,2-dichlorobenzene for 4 hours. The reaction mixture was cooled and immediately purified by flash chromatography on silica gel (gradient elution: hexane then 10% ethyl acetate/hexane) to provide the title compound.

¹H NMR (300 MHz, CDCl₃, ppm): δ3.69 (dd, 2H), 4.80 (broad s, 1H), 5.13–5.25 (m, 2H), 6.02–6.17 (m, 1H), 6.63 (d, 1H), 6.81 (d, 1H), 7.28 (dd, 2H), 7.45 (dd, 4H)

Step D: Preparation of 5-hydroxy-4-propyl-N-(4-chlorophenyl)indole 4-allyl-5-hydroxy-N-(4-chlorophenyl)indole (Step C; 1.0 g, 3.54 mmol) was taken up in 25 mL ethyl acetate and hydrogenated (1 atm) at ambient temperature using 5% palladium on charcoal (40 mg) for 2 hours. The reaction was filtered through celite and concentrated in vacuo to provide the title compound which was used without further purification.

Step E: Preparation of 5-(3-bromopropyl)oxy-4-propyl-N-(4-chlorophenyl)indole

To a solution of 5-hydroxy-4-propyl-N-(4-chlorophenyl) indole (Step D; 500 mg, 1.75 mmol) and potassium carbonate (484 mg, 3.50 mmol) in 7 mL of dimethylformamide (DMF) was added 1,3-dibromopropane (1.77 g, 8.75 mmol). The mixture was stirred at ambient temperature for 2 hours and diluted with ethyl acetate and saturated aqueous ammonium chloride. The aqueous phase was extracted with ethyl acetate and the combined organic extracts were washed brine, dried over magnesium sulfate, filtered, concentrated in vacuo, and the crude residue was used as is in the next step.

Step F: Preparation of Methyl 3-chloro-4-(3-(4-propyl-N-(4-chlorophenyl)-5-indoleoxy)propylthio)phenyl-acetate To a solution of 3-chloro-4-dimethylcarbamoyl-thiophenylacetic acid methyl ester(368 mg, 1.13 mmol) in 5 mL methanol was added a 0.5M solution of sodium methoxide (2.25 mL, 1.13 mmol) in methanol. This mixture was heated to 70° C. for 90 minutes. After cooling to ambient temperature, a solution of 5-(3-bromopropyl)oxy-4-propyl-N-(4-chlorophenyl) indole (Step E; 500 mg, 1.13 mmol) in 8.0 mL methanol was added dropwise. The mixture was stirred at 70° C. for 4 hours, cooled, concentrated in vacuo and diluted with ethyl acetate. The organic layer was washed with water, brine, dried over magnesium sulfate, filtered, and concentrated in vacuo. The crude residue was purified by flash chromatography on silica gel (20% ethyl acetate/hexane) to provide the title compound.

¹H NMR (300 MHz, CDCl₃, ppm): δ1.00 (t, 3H), 1.71 (m, 2H), 2.17 (m, 2H), 2.89 (t, 2H), 3.20 (t, 2H), 3.53 (s, 2H), 3.72 (s, 3H), 4.24 (t, 2H), 6.24 (d, 1H), 6.86 (d, 1H), 7.21–7.34 (m, 5H), 7.40–7.53 (m, 4H)

Step G: Preparation of 3-chloro-4-(3-(6-propyl-N-(4-chlorophenyl-5-indoleoxy)propylthio)phenylacetic acid Methyl 3-chloro-4-(3-(4-propyl-N-(4-chlorophenyl)-5-indoleoxy)propylthiophenyl-acetate (Step F; 100 mg, 0.18 mmol) was taken up in 3 mL methanol:water (2:1). To this was added a 0.5M solution of potassium hydroxide in methanol (1.80 mL, 0.90 mmol). The mixture was heated to 30° C. for 2 hours at which time the mixture was acidified to pH 3 with 1M hydrochloric acid. The aqueous solution was extracted with ethyl acetate and the organic layer was washed with water, brine, dried over magnesium sulfate, filtered, concentrated in vacuo, and the crude residue purified by flash chromatography on silica gel (30% ethyl acetate/hexane/1% acetic acid) to provide the title compound as a golden oil which solidifies upon pumping.

¹H NMR (300 MHz, CDCl₃, ppm): δ1.00 (t, 3H), 1.71 (m, 2H), 2.17 (m, 2H), 2.89 (t, 2H), 3.19 (t, 2H), 3.58 (s, 2H), 4.12 (t, 2H), 6.24 (d, 1H), 6.88 (d, 1H), 7.23 (dd, 1H), 7.23–7.32 (m, 4H), 7.39–7.50 (m, 4H). ESI: MS m/e=529 (M+1)

EXAMPLE 8

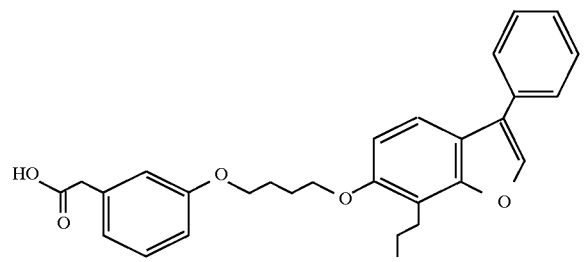

3-(4-(3-phenyl-7-propylbenzofuran-6-yl)oxy)butoxy)phenylacetic acid

STEP 1A

Preparation of 3-phenyl-6-hydroxy-7-propylbenzofuran

To a stirred suspension of 2-propyl-3-(2-phenyl-2-oxoethoxy)phenol (9.30 g) in o-phosphoric acid(85%) (93 mL) at room temperature was added over a 45 minutes period phosphorus pentoxide(46.50 g). During this period the reaction mixture was heated several times with a heat gun. After stirring the mixture for 30 minutes the reaction was checked by TLC (to take a little of sample with a capillary and dissolve sample in water and add several drops of ether; elution: 50% methylene chloride in hexane). The reaction mixture was heated again with heat gun if the reaction was not complete. The reaction mixture continued to be stirred for 20 minutes, then was poured into a beaker containing ice. The reaction flask was then rinsed with water and ether, and the washings were added to the beaker. The organic layer was separated, washed with water, dried over MgSO4, and concentrated. Column Chromatography (silica gel 60, 50% methylene chloride in hexane) gave the title compound.

¹H NMR(400 MHz, CDCl₃): δ7.71 (s, 1H), 7.64 (dd, J=7.0, 1.4 Hz, 2H), 7.51 (d, J=8.5 Hz, 1H), 7.46 (dt, J=7.3, 1.8 Hz, 2H), 7.35 (dt, J=7.2, 1.3 Hz, 1H), 6.82 (d, J=8.4 Hz, 1H), 4.74 (s, very broad, 1H), 2.90 (t, J=7.7 Hz, 2H), 1.75 (hex, J=7.5 Hz, 2H), 1.03 (t, J=7.4 Hz, 3H).

Step 1

The ester was obtained from the Fischer esterification of the commercially available acid in methanol. The 3-hydroxyphenylacetic acid (25 g) was dissolved in methanol (100 ml) with approximately 0.4 ml H₂SO₄ conc. The mixture was heated 16 Hrs under reflux. The mixture was cooled and reduced i. vac. The residue was taken up in ethyl acetate and washed with sat'd aq NaHCO₃, followed by sat'd aq NaCl. The EtOAc extracts were dried over MgSO₄ and reduced i. vac. The ester was used without further purification.

Characteristic NMR Resonances; ¹H NMR 400 MHz (CDCl₃); 7.15 (t, 1H, J=7.7 Hz), 6.80 (t, 1H, J=8.1 Hz), 6.75 (brd s, 1H), 6.72 (dd, 1H, J=2.6, 8.1 Hz), 3.68 (s, 3H), 3.56 (s, 2H).

Step 2

The ester (4.0 g, 1 Eq, 0.024 mol) was dissolved in DMF (30 ml) with 1,4-dibromobutane (14.4 ml, 5 Eq, 0.121 mol) and CsCO₃ (8.3 g, 1.05 Eq, 0.025 mol). The suspension was stirred 1.5 Hrs at RT. The mixture was poured into 0.2N HCl and EtOAc. The aqueous phase was extracted with EtOAc and the EtOAc extracts washed three times with water, followed by sat'd aq NaCl. The extracts were dried over MgSO₄ and reduced i. vac. The product was purified by elution from a silica gel column (150 g E. Merck 40–63μ) with 9:1 Hexanes: EtOAc. The bromide is obtained as an oil.

Characteristic NMR Resonances; ¹H NMR 400 MHz (CDCl₃); 7.21 (t, 1H, J=7.9 Hz), 6.86–6.76 (m, 3H), 3.97 (t, 2H, J=6.0 Hz), 3.67 (s, 3H), 3.58 (s, 2H), 3.47 (t, 2H, J=6.6 Hz), 2.02–2.09 (complex m, 2H), 1.89–1.96 (complex m, 2H).

Step 3

The hydroxybenzofuran (57 mg, 1.0 Eq, 0.228 mmol was dissolved in DMF (0.5 ml) with the bromide (72 mg, 1.05 Eq, 0.24 mmol) and CsCO₃ (82 mg, 1.1 Eq, 0.25 mmol). The suspension was stirred 16 Hrs at RT. The mixture was poured into 0.2N HCl and EtOAc. The aqueous phase was extracted with EtOAc and the EtOAc extracts washed with sat'd aq NaCl. The extracts were dried over Na₂SO₄ and reduced i. vac. The crude adduct was hydrolyzed as below and purified as the free acid.

Step 4

The ester (100 mg, 1 Eq, 0.21 mmol) was dissolved in approximately 4.5 ml 2:1 dioxane: H₂O. 0.1.5M Aqueous LiOH (282 ml, 2.0 Eq, 0.424 mmol) was added dropwise at RT and the mixture stirred 3Hrs. The reaction mixture was diluted into 0.2N HCl and EtOAc. The aqueous phase was extracted with EtOAc and the EtOAc extracts washed with sat'd aq NaCl. The extracts were dried over Na₂SO₄ and reduced i. vac.

The crude acid was purified by elution from an E. Merck 40–63 μRP-8 column with 73:27 CH₃CN:H₂O containing 0.1% v/v TFA. Material was lyophilized.

Characteristic NMR Resonances; ¹H NMR 400 MHz (CDCl₃); 7.69 (s, 1H), 7.55 (d, 1H, J=8.5 Hz), 6.90 (d, 1H, J=8.4 Hz), 4.09 (m, 2H), 4.04 (m, 2H), 3.60 (s, 2H), 2.89 (dd, 2H, J=6.2, 7.7 Hz), 2.01 (m, 4H), 1.69 (sext, 2H, J=7.5 Hz), 0.97 (t, 3H, J=7.4 Hz). MS ESI CH₃CN/NH₄CO₂ aq. M+1 459.3, M+NH₄ 476.4

EXAMPLE 9

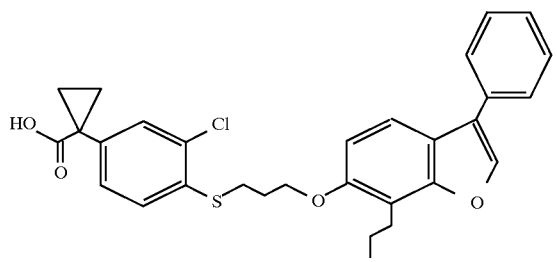

1-(3-chloro-4-(3-(3(3-phenyl-7-propylbenzofuranyl-6-oxy) propyl)thio)phenyl-1-cyclopropane carboxylic acid Step 1

A –78° C. solution of 3-chloro-4-dimethylcarbomoylthio phenyl acetic acid methyl ester (5.167 grams; 19.75 mmol) in dry THF (52 mL) was treated with a solution of lithium bis(trimethylsilyl)amide (1.0M; 20.74 mL; 20.74 mmol). The reaction was stirred for 1 hour at –78° C., then allowed to warm to –10° C. and stirred for 30 minutes. The solution was re-cooled to –78° C. and treated dropwise with methyl iodide (1.29 mL; 20.74 mmol). The reaction was stirred at –78° C. for 30 minutes, then warmed to –10° C. and stirred for an additional 30 minutes. The reaction mixture was partitioned between isopropyl acetate and pH 4 buffer. The layers were separated and the organic washed once with water. The organic was dried over magnesium sulfate, filtered and concentrated to an oil. Silica gel chromatography afforded 2-(3-chloro-4-dimethylcarbamoylthio) phenyl propionic acid methyl ester.

NMR (CDCl₃): 7.52 (d, 1H, J=8.0 Hz); 7.43 (d, 1H, J=1.8 Hz); 7.19 (dd, 1H, J=8.1, 1.9 Hz); 3.68 (quart, 1H, J=7.2 Hz); 3.64 (s, 3H); 3.11 (vbs, 3H); 3.01 (vbs, 3H); 1.47 (d, 3H, J=7.2 Hz).

Step 2

A –78° C. solution 2-(3-chloro-4-dimethylcarbamoylthio)phenyl propionic acid methyl ester (4.547 grams; 15.07 mmol) in dry THF (45 mL) was treated with a solution of lithium bis(trimethylsilyl)amide (1.0M; 18.08 mL; 18.08 mmol). The reaction was stirred for 1 hour at –78° C., then allowed to warm to –10° C. and stirred for 30 minutes. The solution was re-cooled to –78° C. and treated dropwise with a solution of phenyl selenyl bromide (1.0M; 18.08 mL; 18.08 mmol). The reaction was stirred at –78° C. for 15 minutes, then warmed to 20° C. The reaction mixture was partitioned between isopropyl acetate and pH 4 buffer. The layers were separated and the organic washed once with water. The organic was dried over magnesium sulfate, filtered and concentrated to an oil. Silica gel chromatography afforded 2-phenylseleno-2-(3-chloro-4-dimethylcarbamoylthio)phenyl propionic acid methyl ester.

NMR (CDCl₃): 7.48 (m, 2H); 7.33 (m, 4H); 7.24 (m, 2H); 3.69 (s, 3H); 3.11 (vbs, 3H); 3.02 (vbs, 3H); 1.85 (bs, 3H).

Step 3

A 20° C. solution 2-phenylseleno-2-(3-chloro-4-dimethylcarbamoylthio)phenyl propionic acid methyl ester (5.249 grams; 11.49 mmol) in THF (53 mL) was treated with a solution of hydrogen peroxide(10%; 10 mL). The reaction was stirred for 30 minutes. The reaction mixture was partitioned between isopropyl acetate and water. The layers were separated and the organic washed twice with water. The organic was dried over magnesium sulfate, filtered and concentrated to an oil. Silica gel chromatography afforded 2-(3-chloro-4-dimethylcarbamoylthio)phenyl acrylic acid methyl ester.

NMR (CDCl$_3$): 7.56 (d, 1H, J=8.0 Hz); 7.55 (d, 1H, J=2.0 Hz); 7.30 (dd, 1H, J=8.1, 1.9 Hz); 6.43 (bs, 1H); 5.93 (bs, 1H); 3.80 (s, 3H); 3.12 (vbs, 3H); 3.02 (vbs, 3H).

Step 4

A 20° C. solution of trimethyl sulfoxonium iodide (2.122 grams; 9.64 mmol) in dry DMSO (20 mL) was treated with a solution of dimsyl sodium (1.0M; 9.64 mL; 9.64 mmol). The reaction was stirred for 10 minutes. The reaction mixture was treated with a solution of 2-(3-chloro-4-dimethylcarbamoylthio)phenyl acrylic acid methyl ester (2.409 grams; 8.04 mmol) in dry DMSO (24 mL). The reaction was stirred for 1 hour, then partitioned between isopropyl acetate and pH 4 buffer. The layers were separated and the organic washed twice with water. The organic was dried over magnesium sulfate, filtered and concentrated to an oil. Silica gel chromatography afforded 1-(3-chloro-4-dimethylcarbamoylthio)phenyl-1-cyclopropane carboxylic acid methyl ester.

NMR (CDCl$_3$): 7.51 (d, 1H, J=8.2 Hz); 7.47 (d, 1H, J=1.8 Hz); 7.22 (dd, 1H, J=8.1, 1.8 Hz); 3.60 (s, 3H); 3.12 (vbs, 3H); 3.00 (vbs, 3H); 1.59 (apparent quart, 2H, J=3.3 Hz); 1.18 (apparent quart, 2H, J=3.2 Hz).

Step 5

A solution of 1-(3-chloro-4-dimethylcarbamoylthio) phenyl-1-cyclopropane carboxylic acid methyl ester (1.521 grams; 4.85 mmol) in dry MeOH (16 mL) was treated with a solution of sodium methoxide (4.37M; 1.55 mL; 6.79 mmol). The reaction was refluxed for 2 hours. The reaction mixture was cooled to 20° C. and transferred to a dropping funnel. The dropping funnel was placed atop a flask containing a solution of dibromopropane (2.57 mL; 25.32 mmol) in dry MeOH (5 mL). The contents of the dropping funnel were added to the flask dropwise, and the solution stirred for 2 hours. The reaction mixture was partitioned between isopropyl acetate and pH 4 buffer. The layers were separated and the organic washed once with water. The organic was dried over magnesium sulfate, filtered and concentrated. Silica gel chromatography afforded 1-(3-chloro-4-(3-bromopropyl)thio)phenyl-1-cyclopropane carboxylic acid methyl ester.

NMR (CDCl$_3$): 7.34 (d, 1H, J=1.8 Hz); 7.20 (d, 1H, J=8.1 Hz); 7.18 (dd, 1H, J=8.2, 1.9 Hz); 3.61 (s, 3H); 3.54 (t, 2H, J=6.3 Hz); 3.08 (t, 2H, J=7.0 Hz); 2.18 (pent, 2H, J=6.6 Hz); 1.59 (apparent quart, 2H, J=3.7 Hz); 1.14 (apparent quart, 2H, J=3.2 Hz).

Step6

A solution of 1-(3-chloro-4-(3-bromopropyl)thio)phenyl-1-cyclopropane carboxylic acid methyl ester (0.276 grams; 0.76 mmol) in dry DMF (3 mL) was treated with 3-phenyl-6-hydroxy-7-propylbenzofuran (0.210 grams; 0.83 mmol). Cesium carbonate (0.298 grams; 0.91 mmol) was added and the reaction was stirred for 9 hours. The reaction mixture was partitioned between isopropyl acetate and pH 4 buffer. The layers were separated and the organic washed twice with water. The organic was dried over magnesium sulfate, filtered and concentrated. Silica gel chromatography afforded 1-(3-chloro-4-(3-(3-phenyl-7-propylbenzofuran-6-oxy)propyl)thio)phenyl-1-cyclopropane carboxylic acid methyl ester.

NMR (CDCl$_3$): 7.71 (s, 1H); 7.62 (dd, 2H, J=8.5, 1.2 Hz); 7.55 (d, 1H, J=8.5 Hz); 7.44 (t, 2H, J=8.6 Hz); 7.34 (d overlapping bt, 2H, J$_d$=1.9 Hz); 7.24 (d, 1H, J=8.1 Hz); 7.15 (dd, 1H, J=8.4, 1.8 Hz); 6.89 (d, 1H, J=8.6 Hz); 4.16 (t, 2H, J=5.7 Hz); 3.61 (s, 3H); 3.18 (t, 2H, J=7.3 Hz); 2.90 (bt, 2H, J=7.7 Hz); 1.58 (apparent quart, 2H, J=3.0 Hz); 1.13 (apparent quart, 2H, J=3.0 Hz).

Step 7

A solution of 1-(3-chloro-4-(3-(3-phenyl-7-propylbenzofuran-6-oxy)propyl)thio) phenyl-1-cyclopropane carboxylic acid methyl ester (0.287 grams; 0.54 mmol) in isopropanol (5 mL) was refluxed. A solution of potassium hydroxide (1.109M; 1.78 mL; 1.97 mmol) was added dropwise and refluxing continued for 1 hour. The reaction mixture was partitioned between isopropyl acetate and 0.1N HCl. The layers were separated and the organic was dried over magnesium sulfate, filtered and concentrated. Trituration with cyclohexane/methylene chloride (3:1) afforded 1-(3-chloro-4-(3-(3-phenyl-7-propylbenzofuran-6-oxy) propyl)thio)phenyl-1-cyclopropane carboxylic acid (L-803,729).

NMR (CDCl$_3$): 7.71 (s, 1H); 7.62 (dd, 2H, J=8.5, 1.2 Hz); 7.55 (d, 1H, J=8.5 Hz); 7.44 (t, 2H, J=8.6 Hz); 7.34 (d overlapping bt, 2H, J$_d$=1.9 Hz); 7.24 (d, 1H, J=8.1 Hz); 7.15 (dd, 1H, J=8.4, 1.8 Hz); 6.89 (d, 1H, J=8.6 Hz); 4.17 (t, 2H, J=5.7 Hz); 3.18 (t, 2H, J=7.3 Hz); 2.92 (bt, 2H, J=7.7 Hz); 1.65 (apparent quart, 2H, J=3.0 Hz); 1.21 (apparent quart, 2H, J=3.0 Hz).

EXAMPLE 10

3-chloro-4-(3-(6-propyl-N-(4-fluorobenzyl)-5-indoleoxy)-propylthio)phenylacetic acid Step A: Preparation of 5-allyloxyindole 5-allyloxyindole was prepared as described in example 7, step A using the same starting materials.

Step B: Preparation of 4-allyl-5-hydroxy-N-(4-fluorobenzyl)indole

To a solution of sodium hydride (60%, 140 mg, 3.47 mmol) in 4 mL tetrahydrofuran (THF) was added 5-allyloxyindole (Step A; 0.5 g, 2.89 mmol) in 1 mL and the mixture was stirred for 1 hour at ambient temperature. 4-fluorobenzyl bromide (0.43 mL, 3.32 mmol) was added and the reaction stirred 18 hours. The reaction was then quenched with saturated aqueous ammonium chloride and extracted with ethyl acetate. The organic layer was washed with water, brine, dried over magnesium sulfate, filtered through a short pad of silica and used directly in the next step.

Step C: Preparation of 4-allyl-5-hydroxy-N-(4-fluorobenzyl)indole 4-allyl-5-hydroxy-N-(4-fluorobenzyl)indole (Step B; 0.45 g, 1.60 mmol) was refluxed in 5 mL 1,2-dichlorobenzene for 4 hours. The reaction mixture was cooled and immediately purified by flash chromatography on silica gel (gradient elution: hexane then 10% ethyl acetate/hexane) to provide the title compound.

$^1$H NMR (300 MHz, CDCl$_3$, ppm): δ3.67 (dd, 2H), 4.69 (s, 1H), 5.10–5.20 (m, 2H), 4.40 (s, 2H), 6.00–6.14 (m, 1H), 6.48 (d, 1H, J=2 Hz), 6.76 (d, 1H, J=8 Hz), 6.91–7.15 (m, 6H)

Step D: Preparation of 4-propyl-5-hydroxy-N-(4-fluorobenzyl)indole 4-allyl-5-hydroxy-N-(4-fluorobenzyl)indole (Step C; 0.40 g, 1.42 mmol) was taken up in 10 mL ethyl acetate and hydrogenated (1 atm) at ambient temperature using 5% palladium on charcoal (15 mg) for 2 hours. The reaction was filtered through celite and concentrated in vacuo to provide the title compound which was used without further purification.

Step D-1: Preparation of methyl 3-chloro-4-(3-bromopropylthio)-phenylacetate

To a solution of methyl 3-chloro-4-dimethylcarbamoylthiophenylacetate (85 g, 0.295 mol) in methanol (250 mL) was added 25% NaOMe in methanol (74 mL, 0.34 mol). The reaction was heated to reflux for 2 h. TLC analysis shows residual starting carbamate. Additional NaOMe/MeOH (10 mL) was added and the mixture stirred an additional 30 min at reflux. After cooling to ambient temperature, the thiolate solution was added dropwise to a solution of 1,3-dibromopropane (120 mL, 1.18 mol) in methanol (250 mL). The resulting solution was refluxed for 3 h then cooled to ambient temperature. After standing overnight, the reaction was quenched by pouring into ice water (2 L). After adjusting to pH 1 with conc. HCl (ca. 10 mL), the aqueous was extracted with EtOAc (2L then 2×1 L). The combined organics were washed with water (2×1 L), brine (1 L), dried over anhyd. MgSO$_4$, filtered, and concentrated. The residue was dissolved in EtOAc/hexane (1/9) and eluted through a plug of silica gel (70–230 mesh, ca. 2 L, packed in EtOAc/hexane, 1/9). The fractions containing product were combined and evaporated to give title compound (48 g, 48% yield) as an off-white solid.

NMR (CDCl$_3$) δ7.25–7.32 (m, 2H), 7.15 (dd, 1H, J=8.1, 1.8 Hz), 3.71 (s, 3H), 3.57 (s, 2H), 3.55 (t, 2H, J=7.7 Hz), 3.10 (t, 2H, J=7.7 Hz), 2.18 (m, 2H).

Step E: Preparation of Methyl-3-chloro-4-(3-(4-propyl-N-(4-fluorobenzyl)indolyl-5-oxy)propylthio)phenylacetate To a solution of potassium carbonate (29 mg, 0.207 mmol) in 0.5 mL of dimethylformamide (DMF) was added 4-propyl -5-hydroxy-N-(4-fluorobenzyl)indole(step D, 39 mg, 0.135 mmol) and the mixture stirred 30 min at 60° C. Methyl-3-chloro-4-(3-bromopropyl thio)phenylacetate (step D-1, 50 mg, 0.148 mmol) in 0.5 mL DMF was added and the reaction stirred 5 hours. After cooling to ambient temperature, the reaction was diluted with ethyl acetate. The organic layer was washed with water, brine, dried over magnesium sulfate, filtered, and concentrated in vacuo. The crude residue was purified by flash chromatography on silica gel (20% ethyl acetate/hexane) to provide the title compound.

$^1$H NMR (300 MHz, CDCl$_3$, ppm): δ1.02 (t, 3H), 1.72 (m, 2H), 2.19 (m, 2H), 2.84 (t, 2H), 3.20 (t, 2H), 3.55 (s, 2H), 3.72 (s, 3H), 4.12 (t, 2H), 4.40 (s, 2H), 6.50 (d, 1H), 6.72 (d, 1H), 6.90–7.21 (m, 9H)

ESI: MS m/e=541 (M+1)

Step F: Preparation of 3-chloro-4-(3-(6-propyl-N-(4-chlorophenyl)-indolyl-5-oxy)propylthio)phenylacetic acid Using the method of Example 7, step G, and substituting methyl-3-chloro-4-(3-(4-propyl-N-(4-fluorobenzyl)indolyl-5-oxy)propylthio)phenylacetate (Step E) as the starting material, the title compound was obtained.

$^1$H NMR (300 MHz, CDCl$_3$, ppm): δ1.02 (t, 3H), 1.72 (m, 2H), 2.19 (m, 2H), 2.84 (t, 2H), 3.20 (t, 2H), 3.55 (s, 2H), 4.12 (t, 2H), 4.40 (s, 2H), 6.50 (d, 1H), 6.72 (d, 1H), 6.90–7.21 (m, 9H)

ESI: MS m/e=527 (M+1)

EXAMPLE 11

3-Chloro-4-(1- propyl-dibenzofuranyl-2-oxy-propylthio)-phenylacetic acid.

Step A: Preparation of methyl 3-chloro-4-(3-bromopropylthio)-phenylacetate.

To a solution of 3-chloro-4-dimethylcarbamoyl-thiophenylacetate (85 g, 0.295 mol) in methanol (250 mL) was added 25% NaOMe in methanol (74 mL, 0.34 mol). The reaction was heated to reflux for 2 h. TLC analysis shows residual starting carbamate. Additional NaOMe/MeOH (10 mL) was added and the mixture stirred an additional 30 min at reflux. After cooling to ambient temperature, the thiolate solution was added dropwise to a solution of 1,3-dibromopropane (120 mL, 1.18 mol) in methanol (250 mL). The resulting solution was refluxed for 3 h then cooled to ambient temperature. After standing overnight, the reaction was quenched by pouring into ice water (2 L). After adjusting to pH 1 with conc. HCl (ca. 10 mL), the aqueous was extracted with EtOAc (2 L then 2×1 L). The combined organics were washed with water (2×1 L), brine (1 L), dried over anhyd. MgSO4, filtered, and concentrated. The residue was dissolved in EtOAc/ hexane (1/9) and eluted through a plug of silica gel (70–230 mesh, ca. 2 L, packed in EtOAc/hexane, 1/9). The fractions containing product were combined and evaporated to give title compound (48 g, 48% yield) as an off-white solid.

NMR (CDCl$_3$) δ7.25–7.32 (m, 2H), 7.15 (dd, 1H, J=8.1, 1.8 Hz), 3.71 (s, 3H), 3.57 (s, 2H), 3.55 (t, 2H, J=7.7 Hz), 3.10 (t, 2H, J=7.7 Hz), 2.18 (m, 2H).

Step B: Preparation of 2-propenyloxydibenzofuran

A solution of 2-hydroxydibenzofuran (2.0 grams) was treated with allyl bromide (1.2 mL) and potassium carbonate (1.5 grams). The mixture was stirred over night at 60°. The reaction was partitioned between methylene chloride and water. The organic was washed once with water and dried over sodium sulfate. The organic layer was filtered and concentrated to an oil which was chromatographed over silica gel to afford the title compound.

$^1$H NMR (400 MHz, CDCl$_3$, ppm ) δ7.10–7.90(m, 6H, ), 6.06–6.18 (m, 1H), 5.06 (m, 1H), 4.62 (dd, 2H, J=3.79, 1.47 Hz)

Step C: Preparation of 2-hydroxy-1-propyldibenzofuran

A solution of 2-propenyloxydibenzofuran (0.9 grams) in ortho-dichlorobenzene 8 mL) was refluxed for 22 hours. Mixture was cooled to room temperature and was chromatographed over silica gel to afford the intermediate which was hydrogenated over 10% Pd/C catalyst (90 mg) in ethyl acetate for 18 hours. The reaction was filtered through Celite and all volatiles were removed to afford the title compound.

$^1$H NMR (400 MHz, CDCl$_3$, ppm ) δ6.89–7.96 (m, 6H), 3.12 (t, 2H J=7.4 Hz), 1.77 (m, 2H), 1.09 (t, 3H, J=7.3 Hz).

Step D: Preparation of methyl 3-Chloro-4-(1- propyl-2-dibenzofuranyl-2-oxy-propylthio)-phenyl acetate A mixture of methyl 3-chloro-4-(3-bromopropylthio)-phenylacetate (196 mg, 0.58 mmoles), 2-hydroxy-1-

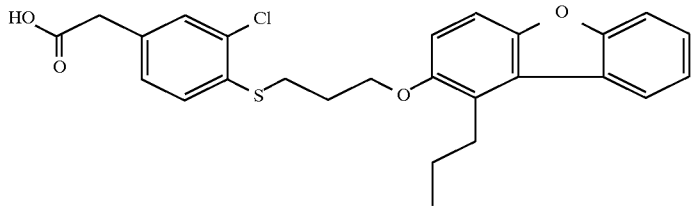

propyldibenzofuran (165 mg, 0.58 mmoles), cesium carbonate (189 mg, 0.58 mmoles), and DMF (2.3 ml) was heated at 800 in a nitrogen atmosphere for 5 hrs with magnetic stirring. The suspension was partitioned between ethyl acetate and dilute HCl solution. The aqueous phase was extracted twice with ethyl acetate. The combined organic phases were washed three times with water, once with saturated NaCl solution and dried (MgSO$_4$). Evaporation in vacuo gave the title compound as an orange oil. It was used in the next reaction without purification.

$^1$H NMR (400 MHz, CDCl$_3$, ppm) δ6.98–7.97(m, 9H), 4.10(t, 2H J=5.8 Hz), 3.68(s, 3H), 3.54(s, 2H), 3.17(t, 2H J=7.2 Hz ), 2.59(t, 2H), 2.14(m, 2H), 1.73(m, 2H), 1.05(t, 3H J=7.4 Hz).

Step E: 3-Chloro-4-(1- propyl-dibenzofuranyl-2-oxy-propylthio)-phenylacetic acid.

A solution of 3-Chloro-4-(1- propyl-2-dibenzoxyfuran) propylthio)-phenyl acetate (205 mg, 0.37 mmoles), LiOH solution (1.0M, 1.11 ml, 1.11 mmoles), and methanol (11 ml) was kept at room temperature for 16 hr. It was heated under reflux for 15 min, and most of the methanol was removed in vacuo. The residue was suspended in water and acidified with dilute HCl. The suspension was extracted three times with ethyl acetate. The combined extracts were washed with water and saturated brine and dried (MgSO$_4$). The solid residue after evaporation of the solvent in vacuo was triturated with CH$_2$Cl$_2$, filtered and dried to give the title compound as an off-white solid, mp 153°–154°.

$^1$H NMR (400 MHz, CDCl$_3$, ppm ) δ6.98–7.97(m, 9H), 4.10(t, 2H J=5.8 Hz), 3.57(s, 2H), 3.19(t, 2H J=7.2 Hz ), 2.02–2.08(m, 2H), 2.20(m, 2H), 1.73(m, 2H), 1.05(t, 3H J=7.4 Hz).

ESI-MS: m/e =468 (M+)

EXAMPLE 12 by thin layer chromatography (TLC) with the title compound. Total recovery of the title compound was 1.80 grams (57% yield).

$^1$H NMR (500 MHz, CDCl$_3$): δ7.36 (m, 5H), 7.17 (t, 1H), 6.72 (m, 3H), 6.66 (s, 1H), 5.11 (s, 2H), 3.47 (q, 2H), 2.78 (t, 2H).

Step B: Preparation of 1-propenyloxy-3-(2-carbobenzyloxyamino)ethyl benzene 1.80 grams (6.6 mmole, 1.0 eq.) of 1-hydroxy-3-(2-carbobenzyloxyamino)ethyl benzene from step A was dissolved in 30 ml of N,N-dimethylformamide. 2.29 grams (16.6 mmole, 2.5 eq.) of potassium carbonate was suspended in the solution, and 665 µl (7.3 mmole, 1.1 eq) of allyl iodide was added. The reaction was stirred at 60° C. for 300 minutes, after which TLC shows incomplete conversion. Another 550 µl (6.0 mmole, 0.9 eq) of allyl iodide was added portionwise until reaction was nearly complete. Quenched by adding water and extracted 3× with dichloromethane. The organic layer was dried over sodium sulfate, filtered and the filtrate was evaporated. The residue was pumped on high vacuum for 72 hours, then purified by silica gel chromatography to give 1.75 grams (85% yield) of the title compound.

$^1$H NMR (500 MHz, CDCl$_3$): δ7.36 (m, 5H), 7.22 (t, 1H), 6.79 (m, 3H), 6.07 (m, 1H), 5.38 (ddd, 2H), 5.12 (s,2H), 4.53 (d, 2H), 3.48 (q, 2H), 2.81 (t, 2H).

Step C: Preparation of 1-hydroxy-2-propenyl-5-(2-carbobenzyloxyamino)ethyl benzene 1.74 grams (5.6 mmole) of 1-propenyloxy-3-(2-carbobenzyloxyamino)ethyl benzene from step B was dissolved in 30 ml of 1,2-dichlorobenzene. The solution was heated to 180° C. for 90 hours. TLC indicated that two products hat been formed in a nearly 1:1 ratio. Multiple column chromatographies provided 930 mg (53% yield) of the title compound (the less polar product) and 766 mg (44% yield) of 1-hydroxy-2-propenyl-5-(2-carbobenzyloxyamino) ethyl benzene (the more polar product).

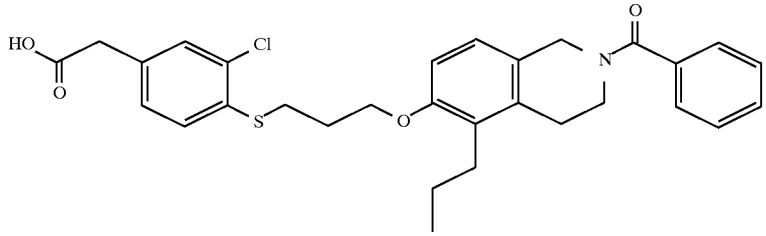

3-chloro-4-(3-(1-benzoyl-6-propyl-5-tetrahydroiso-[3,6]-quinolinoxy)propylthio) phenylacetic acid Step A: Preparation of 1-hydroxy-3-(2-carbobenzyloxyamino)ethyl benzene 2.00 grams of 1-hydroxy-3-(2-amino)ethyl benzene hydrochloride (11.5 mmoles, 1.0 eq.) was suspended in 60 ml dry dichloromethane, the reaction vessel was cooled to 0° C. and 4.6 ml pyridine (57.6 mmole, 5.0 eq.) was added. Finally, 3.5 ml of benzyl chloroformate (24.5 mmole, 2.1 eq.) was added and the reaction stirred for 40 hours. The reaction was quenched by the addition of water. After transferring the 2-phase solution to a separatory funnel, the organic layer was washed 3× with water and 3× with dilute aqueous HCl. The organic layer was dried over sodium sulfate, filtered and the filtrate evaporated. Silica gel chromatography provided pure samples of both the title compound and di-Cbz product. The di-Cbz product was dissolved in 25 ml dioxane and 25 ml of 1N sodium hydroxide and stirred for 15 minutes. The hydrolysis product co-elutes Title compound $^1$H NMR (500 MHz, CDCl$_3$): δ7.37 (m, 5H), 7.08 (t, 1H), 6.75 (dd, 2H), 6.01 (m, 1H), 5.12 (s, 2H), 5.06 (dd, 2H), 3.48 (d, 2H), 3.42 (q, 2H), 2.85 (t, 2H).

1-hydroxy-2-propenyl-5-(2-carbobenzyloxyamino)ethyl benzene:$^1$H NMR (500 MHz, CDCl$_3$): δ7.37 (m, 5H), 7.04 (d, 1H), 6.71 (d, 1H), 6.64 (s, 1H), 6.01 (m, 1H), 5.14 (dd, 2H), 5.11 (s, 2H), 3.46 (q, 2H), 3.40 (d, 2H), 2.76 (t, 2H).

Step D: Preparation of 1-hydroxy-2-propyl-3-(2-amino) ethyl benzene 600 mg (1.92 mmole, 1.0 eq.) of 1-hydroxy-2-propenyl-3-(2-carbobenzyloxyamino)ethyl benzene from step C was dissolved in 24 ml of methanol. The reaction vessel was evacuated and charged with nitrogen, then 264 mg (0.25 mmole, 0.13 eq.) of 10% palladium on carbon was suspended in the solution. The reaction vessel was then evacuated and charged with hydrogen and the reaction stirred for 150 minutes. TLC indicated that the reaction was complete, so the catalyst was filtered over celite and the filtrate evaporated to provide 333 mg (97% yield) of the title compound.

¹H NMR (500 MHz, CD₃OD): δ6.90 (t, 1H), 6.62 (ddd, 2H), 2.78 (m, 4H), 2.61 (t, 2H), 1.53 (m, 2H), 0.98 (t, 3H).

Step E: Preparation of 1-hydroxy-2-propyl-3-(2-tert-butoxycarbonyl amino)ethyl benzene 220 mg (1.23 mmole, 1.0 eq.) of 1-hydroxy-2-propyl-3-(2-amino)ethyl benzene from step D was dissolved in 10 ml of 1,4-dioxane, to which was added 4.30 ml of 1N NaOH (4.3 mmole, 3.5 eq.) and 295 mg (1.35 mmole, 1.1 eq.) of di-tert-butyl dicarbonate. After 3 hours at room temperature the reaction was worked up by diluting with ethyl acetate, water, and enough dilute HCl to acidify the aqueous layer. The mixture was transferred to a separatory funnel, shaken and the organic separated. Extracted the aqueous layer a second time with ethyl acetate, combined the organics, dried them over sodium sulfate, filtered and evaporated the filtrate. The residue was pumped on high vacuum to give 330 mg (97% yield) of the title compound, which was used without further purification.

¹H NMR (400 MHz, CDCl₃): δ6.99 (t, 1H), 6.72 (d, 1H), 6.62 (d, 1H), 3.35 (br m, 2H) 2.78 (t, 2H), 2.58 (t, 2H), 1.53 (m, 2H), 1.43 (s, 9H), 0.98 (t, 3H).

Step F: Preparation of methyl 3-chloro-4-(3-bromopropylthio) phenyl acetate

Same procedure and materials as described in Example 11, Step A.

Step G: Preparation of methyl 3-chloro-4-(3-(2-tert-butoxycarbonyl amino)ethyl 2-propyl-1-phenoxy) propylthio) phenyl acetate 330 mg (1.19 mmole, 1.0 eq.) of 1-hydroxy-2-propyl-3-(2-tert-butoxycarbonyl amino)ethyl benzene from step E was dissolved in 6 ml N,N-dimethylformamide, after which 1.05 gram (3.22 mmole, 2.7 eq.) of cesium carbonate was suspended and 402 mg of methyl 3-chloro-4-(3-bromopropylthio) phenyl acetate from step F was added. The reaction stirred at 50° C. for 16 hours. Diluted the reaction mixture with water and extracted twice with ethyl acetate. The organic layer was dried over sodium sulfate, filtered and evaporated. Silica gel chromatography provided 272 mg (43% yield) of the title compound.

¹H NMR (500 MHz, CDCl₃): δ7.33 (d, 1H), 7.28 (m, 1H), 7.15 (dd, 1H), 7.11 (t, 1H), 6.79 (d, 1H), 6.73 (d, 1H), 4.09 (t, 2H), 3.72 (s, 3H), 3.59 (s, 2H), 3.36 (br m, 2H), 3.18 (t, 2H), 2.83 (t, 2H), 2.65 (t, 2H), 2.18 (m, 2H), 1.52 (m, 2H), 1.46 (s, 9H), 0.99 (t, 3H).

Step H: Preparation of methyl 3-chloro-4-(3-(3-(2-amino) ethyl 2-propyl-1-phenoxy) propylthio) phenyl acetate 251 mg (0.47 mmole, 1.0 eq.) of methyl 3-chloro-4-(3-(3-(2-tert-butoxycarbonylamino)ethyl 2-propyl-1-phenoxy) propylthio) phenyl acetate from step G was dissolved in 2 ml of 4N HCl in dioxane (8 mmole, 17.1 eq.). After 1 hour the dioxane was removed by rotary evaporation and the crude residue triturated with diethyl ether. Most of ether was decanted, with the rest being removed by rotary evaporation followed by high vacuum pumping for 16 hours to give 218 mg (99% yield) of the title compound.

¹H NMR (500 MHz, CD₃OD): δ7.36 (d, 1H), 7.33 (d, 1H), 7.17 (dd, 1H), 7.12 (t, 1H), 6.84 (d, 1H), 6.80 (d, 1H), 4.10 (t, 2H), 3.65 (s, 3H), 3.61 (s, 2H), 3.19 (t, 2H), 3.08 (m, 2H), 2.97 (m, 2H), 2.65 (m, 2H), 2.14 (t, 2H), 1.54 (m, 2H), 0.98 (t, 3H).

Step I: Preparation of methyl 3-chloro-4-(3-(6-propyl-5-tetrahydroiso-[3,61]-quinolinoxy)propylthio) phenylacetate 218 mg (0.46 mmole, 1.0 eq.) of methyl 3-chloro-4-(3-(3-(2-amino)ethyl 2-propyl-1-phenoxy) propylthio) phenyl acetate from step H was dissolved in 2.3 ml of dichloromethane. 92 μl of trifluoroacetic acid (4% v/v) and 186 μl (2.3 mmole, 5.0 eq.) of 37% formaldehyde were then added. After 90 minutes the solvent was evaporated by rotary evaporation and the residue pumped on high vacuum for 16 hours. Silica gel chromatography with a dichloro-methane/methanol/ammonium hydroxide eluent provided 179 mg (87% yield) of the title compound.

¹H NMR (500 MHz, CDCl₃, 50° C.): δ7.34 (d, 1H), 7.31 (d, 1H), 7.14 (dd, 1H), 6.85 (d, 1H), 6.69 (d, 1H), 4.08 (t, 2H), 3.72 (s, 3H), 3.71 (s, 2H), 3.58 (s, 2H), 3.16 (t, 2H), 2.87 (m, 4H), 2.61 (dt, 2H), 2.16 (m, 2H), 1.53 (m, 2H), 0.99 (t, 3H).

Step J: Preparation of methyl 3-chloro-4-(3-(1-benzoyl-6-propyl-5-tetrahydroiso-[3,6]-quinolinoxy)propylthio) phenyl acetate 20 mg (45 μmole, 1.0 eq.) of methyl methyl 3-chloro-4-(3-(6-propyl-5-tetrahydroiso-[3,6]-quinolinoxy)propylthio) phenylacetate from step I was dissolved in 200 μl of dichloromethane. 18 μl (223 μmole, 5.0 eq.) of pyridine and 10.4 μl (89 μmole, 2.0 eq.) of benzoyl chloride were added and the reaction was stirred for 16 hours under nitrogen atmosphere. The reaction mixture was further diluted with dichloromethane and washed twice with dilute aqueous HCl. The organic layer was dried over sodium sulfate, filtered and the filtrate evaporated to give 23 mg (93% yield) of the title compound without further purification.

¹H NMR (500 MHz, CDCl₃, 55° C.): δ8.11 (dd, 1H), 7.45 (m, 6H), 7.34 (d, 1H), 7.31 (d, 1H), 7.14 (dd, 1H), 6.74 (br, 2H), 4.85–4.45 (br, 2H), 4.09 (t, 2H), 3.72 (s, 3H), 3.58 (s, 2H), 3.16 (t, 2H), 2.90 (br, 2H), 2.64 (dt, 2H), 2.17 (m, 2H), 1.53 (m, 2H), 0.98 (t, 3H).

Step K: Preparation of 3-chloro-4-(3-(1-benzoyl-6-propyl-5-tetrahydroiso-[3,6]-quinolinoxy)propylthio) phenylacetic acid 21.5 mg (39 μmole, 1.0 eq.) of methyl 3-chloro-4-(3-(1-benzoyl-6-propyl-5-tetrahydroiso-[3,6]-quinolinoxy) propyl-thio) phenyl acetate from step J was dissolved in 0.4 ml of tetrahydrofuran. Added 0.25 ml (62.5 μmole, 1.6 eq.) of 0.25N lithium hydroxide and allowed to stir for 2 hours. Water was added, as was dichloromethane followed by dilute aqueous HCl (enough to acidify aqueous layer). Organic layer was separated and dried over sodium sulfate, filtered and the filtrate was evaporated. Preparative TLC was used to purify the final product. The title compound gives a broad NMR in CDCl₃.

¹H NMR (500 MHz, CDCl₃): δ8.11 (br, 1H), 7.45 (br s, 6H), 7.30–6.90 (br, 3H), 6.73 (br, 2H), 4.84 (br, 1H), 4.53 (br, 1H), 4.10 (br, 2H), 3.58 (br, 2H), 3.16 (br, 2H), 2.92 (br, 2H), 2.60 (br, 2H), 2.15 (br, 2H), 1.48 (m, 2H), 0.96 (br, 3H).

MS (ESI; TFA/HCOONH₄): 538.2 m/e [M+1].

EXAMPLE 13

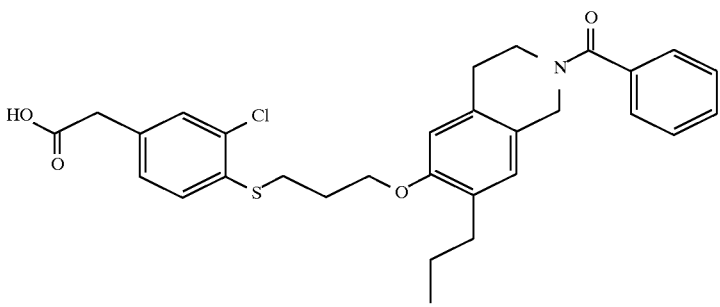

3-chloro-4-(3-(1-benzoyl-4-propyl-5-tetrahydroiso-[3,6]-quinolinoxy)propylthio) phenylacetic acid Step A: Preparation of 1-hydroxy-2-propyl-5-(2-amino) ethyl benzene 566 mg (1.81 mmole, 1.0 eq.) of 1-hydroxy-2-propenyl-5-(2-carbobenzyloxy-amino)ethyl benzene from Example 12, Step C was dissolved in 9 ml of methanol. The reaction vessel was evacuated and charged with nitrogen, then 385 mg (0.36 mmole, 0.2 eq.) of 10% palladium on carbon was suspended in the solution. The reaction vessel was then evacuated and charged with hydrogen and the reaction stirred for 150 minutes. TLC indicated that the reaction was complete, so the catalyst was filtered over celite and the filtrate evaporated to provide 313 mg (96% yield) of the title compound.

$^1$H NMR (500 MHz, CD$_3$OD): δ6.96 (d, 1H), 6.60 (s, 1H), 6.59 (dd, 1H), 2.87 (t, 2H), 2.66 (t, 2H), 2.52 (t, 2H), 1.58 (m, 2H), 0.92 (t, 3H

Step B: Preparation of 1-hydroxy-2-propyl-5-(2-tert-butoxycarbonyl amino)ethyl benzene 194 mg (1.08 mmole, 1.0 eq.) of 1-hydroxy-2-propyl-5-(2-amino)ethyl benzene from step A was dissolved in 10 ml of 1,4-dioxane, to which was added 3.8 ml of 1N NaOH (3.8 mmole, 3.5 eq.) and 389 mg (1.78 mmole, 1.65 eq.) of di-tert-butyl dicarbonate. After 2 hours at room temperature the reaction was worked up by diluting with ethyl acetate, water, and enough dilute HCl to acidify the aqueous layer. The mixture was transferred to a separatory funnel, shaken and the organic separated. Extracted the aqueous layer a second time with ethyl acetate, combined the organics, dried them over sodium sulfate, filtered and evaporated the filtrate. The residue was pumped on high vacuum to give 301 mg (100% yield) of the title compound.

$^1$H NMR (400 MHz, CDCl$_3$): δ7.02 (d, 1H), 6.64 (d, 1H), 6.59 (s, 1H), 4.55 (br s, 1H), 3.35 (br m, 2H) 2.67 (t, 2H), 2.55 (t, 2H), 1.61 (m, 2H), 1.42 (s,9H), 0.96 (t, 3H).

Step C: Preparation of methyl 3-chloro-4-(3-(5-(2-tert-butoxycarbonyl amino)ethyl 2-propyl-1-phenoxy) propylthio) phenyl acetate 301 mg (1.08 mmole, 1.0 eq.) of 1-hydroxy-2-propyl-5-(2-tert-butoxycarbonyl amino)ethyl was dissolved in 10 ml N,N-dimethylformamide, after which 370 mg (1.13 mmole, 1.05 eq.) of cesium carbonate was suspended and 346 mg (1.03 mmole, 0.95 eq.) of methyl 3-chloro-4-(3-bromopropylthio) phenyl acetate from example 12, step F, was added. The reaction stirred at 60° C. for 2 hours. Diluted the reaction mixture with water, acidified with 0.5N HCl and extracted twice with ethyl acetate. The organic layer was dried over sodium sulfate, filtered and evaporated. Silica gel chromatography provided 288 mg (52% yield) of the title compound.

$^1$H NMR (500 MHz, CD$_3$OD): δ7.35 (d, 1H), 7.32 (d, 1H), 7.14 (dd, 1H), 6.99 (d, 1H), 6.74 (s, 1H), 6.69 (d, 1H), 4.10 (t, 2H), 3.68 (s, 3H), 3.61 (s, 2H), 3.23 (m, 2H), 3.18 (t, 2H), 2.69 (t, 2H), 2.55 (t, 2H), 2.12 (m, 2H), 1.56 (m, 2H), 1.41 (s, 9H), 0.90 (t, 3H).

Step D: Preparation of methyl 3-chloro-4-(3-(5-(2-amino) ethyl 2-propyl-1-phenoxy) propylthio) phenyl acetate 236 mg (0.44 mmole, 1.0 eq.) of methyl 3-chloro-4-(3-(5-(2-tert-butoxycarbonylamino)ethyl 2-propyl-1-phenoxy) propylthio) phenyl acetate from Example 13, step C was dissolved in 2 ml of 4N HCl in dioxane (8 mmole, 18.1 eq.). After 1 hour the dioxane was removed by rotary evaporation and the crude residue triturated with diethyl ether. Most of ether was decanted, with the rest being removed by rotary evaporation followed by high vacuum pumping for 16 hours to give 205 mg (98% yield) of the title compound.

$^1$H NMR (500 MHz, CDCl$_3$): δ7.31 (d, 1H), 7.27 (d, 1H), 7.14 (d, 1H), 7.04 (d, 1H), 6.74 (d, 1H), 6.69 (s, 1H), 4.05 (t, 2H), 3.71 (s, 3H), 3.5 (s, 2H), 3.24 (br, 2H), 3.12 (t, 2H), 3.07 (br, 2H), 2.55 (t, 2H), 2.13 (t, 2H), 1.58 (m, 2H), 0.93 (t, 3H).

Step E: Preparation of methyl 3-chloro-4-(3-(4-propyl-5-tetrahydroiso-[3,6]-quinolinoxy)propylthio) phenylacetate 205 mg (0.43 mmole, 1.0 eq.) of methyl 3-chloro-4-(3-(5-(2-amino)ethyl 2-propyl-1-phenoxy) propylthio) phenyl acetate from Example 13, step D was dissolved in 2.3 ml of dichloromethane. 92 l of trifluoroacetic acid (4% v/v) and 175 μl (2.2 mmole, 5.0 eq.) of 37% formaldehyde were then added. After 90 minutes the solvent was evaporated by rotary evaporation and the residue pumped on high vacuum for 16 hours. Silica gel chromatography with a dichloromethane/methanol/ammonium hydroxide eluent provided 154 mg (79% yield) of the title compound.

$^1$H NMR (500 MHz, CDCl$_3$): δ7.33 (d, 1H), 7.29 (d, 1H), 7.15 (dd, 1H), 6.81 (s, 1H), 6.57 (s, 1H), 4.07 (t, 2H), 3.72 (s, 3H), 3.68 (br, 2H), 3.59 (s, 2H), 3.16 (t, 2H), 2.86 (br, 4H), 2.55 (t, 2H), 2.16 (m, 2H), 1.59 (m, 2H), 0.94 (t, 3H).

Step F: Preparation of methyl 3-chloro-4-(3-(1-benzoyl-4-propyl-5-tetrahydroiso-[3,6]-quinolinoxy)propylthio) phenyl acetate 20 mg (45 μmole, 1.0 eq.) of methyl 3-chloro-4-(3-(4-propyl-5-tetrahydroiso-[3,6]-quinolinoxy)propylthio) phenylacetate from Example 13, step E was dissolved in 500 μl of dichloromethane. 18 μl (223 μmole, 5.0 eq.) of pyridine and 10.4 μl (89 μmole, 2.0 eq.) of benzoyl chloride were added and the reaction was stirred for 16 hours under nitrogen atmosphere. The reaction mixture was further diluted with dichloromethane and washed twice with dilute aqueous HCl. The organic layer was dried over sodium sulfate, filtered and the filtrate evaporated to give 18 mg (93% yield) of the title compound without further purification.

¹H NMR (500 MHz, CDCl₃, 55° C.): δ7.45 (m, 6H), 7.34 (d, 1H), 7.31 (d, 1H), 7.14 (dd, 1H), 6.61 (s, 1H), 4.85–4.50 (br, 2H), 4.09 (t, 2H), 3.72 (s, 3H), 3.58 (s, 2H), 3.16 (t, 2H), 2.87 (br, 2H), 2.57 (br t, 2H), 2.17 (m, 2H), 1.60 (m, 2H), 0.95 (t, 3H).

Step G: Preparation of 3-chloro-4-(3-(1-benzoyl-4-propyl-5-tetrahydroiso-[3,6]-quinolinoxy)propylthio) phenylacetic acid 17.5 mg (32 μmole, 1.0 eq.) of methyl 3-chloro-4-(3-(1-benzoyl-4-propyl-5-tetrahydroiso-[3,6]-quinolinoxy) propyl-thio) phenyl acetate from Example 13, step F was dissolved in 0.30 ml of 1:1 methanol:tetrahydrofuran. Added 0.16 ml (40 μmole, 1.6 eq.) of 0.25N sodium hydroxide and allowed to stir for 45 minutes. Water was added, as was ethyl acetate followed by dilute aqueous HCl (enough to acidify aqueous layer). The organic layer was separated and dried over sodium sulfate, filtered and the filtrate was evaporated to give 16.6 mg (97% yield) of the title compound. The title compound gives a broad NMR in CDCl₃.

1H NMR (500 MHz, CDCl₃): δ7.45 (br, 6H), 7.30–6.90 (br, 3H), 6.54 (s, 1H), 4.84 (br, 1H), 4.53 (br, 1H), 4.12 (br, 2H), 3.96 (br, 1H), 3.62 (br, 1H), 3.58 (s, 2H), 3.16 (br m, 2H), 2.79 (t, 2H), 2.59 (br, 2H), 2.16 (br, 2H), 1.60 (m, 2H), 0.96 (br, 3H).

MS (ESI; TFA/HCOONH₄): 538.4 m/e [M+1].

EXAMPLE 14

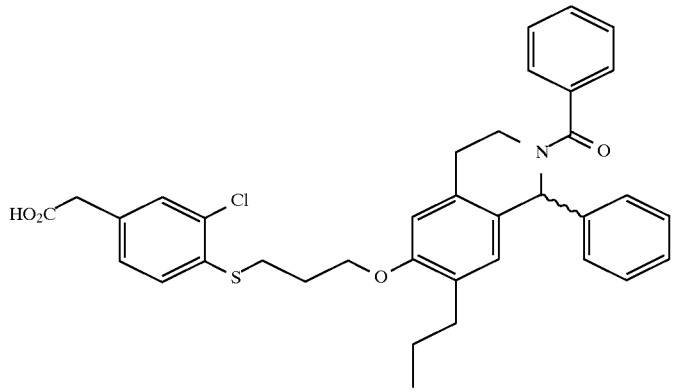

3-chloro-4-(3-(1-benzoyl-2-(R,S)-phenyl-4-propyl-5-tetrahydroiso-[3,6]-quinolinoxy)propylthio) phenylacetic acid Step A: Preparation of 2-(R,S)-phenyl-4-propyl-5-hydroxy tetrahydroiso-[3,6]-quinoline 105 mg (0.59 mmole, 1.0 eq.) of 1-hydroxy-2-propyl-5-(2-amino)ethyl benzene from example 13, step A was stirred with 3.1 ml dichloromethane, 155 μl (5% v/v) trifluoroacetic acid and 119 μl (1.17 mmole, 2.0 eq.) of benzaldehyde for 16 hours. The solvent was evaporated by rotary evaporation and the crude purified by silica gel chromatography to give 111 mg (71% yield) of the title compound.

1H NMR (500 MHz, CD₃OD): δ7.34–7.20 (m, 5H), 6.53 (s, 1H), 6.36 (s, 1H), 4.97 (s, 1H), 3.15 (dt, 1H), 3.00–2.86 (m, 2H), 2.73 (dt, 1H), 2.37 (t, 2H), 1.43 (m, 2H), 0.80 (t, 3H).

Step B: Preparation of 1-tert-butoxycarbonyl-2-(R,S)-phenyl-4-propyl-5-hydroxy tetrahydroiso-[3,6]-quinoline 105 mg (0.39 mmole, 1.0 eq) of 2-(R,S)-phenyl-4-propyl-5-hydroxy tetrahydroiso-[3,6]-quinoline from step A was stirred with 4 ml 1,4-dioxane, 1.38 ml (1.38 mmole, 3.5 eq.) of 1.0N sodium hydroxide and 154 mg (0.71 mmole, 1.8 eq.) of di-tert-butyl dicarbonate for 16 hours. The dioxane was removed by rotary evaporation, the aqueous was then acidified with dilute HCl and extracted twice with ethyl acetate. The organic layer was dried over sodium sulfate, filtered and evaporated. The crude residue was purified by silica gel chromatography to give 101 mg (70% yield) of the title compound.

1H NMR (500 MHz, CDCl₃): δ7.27 (m, 5H), 6.78 (br s, 1H), 6.61 (s, 1H), 4.90 (br s, 1H), 4.00 (br, 1H), 3.14 (m, 1H), 2.88 (br, 1H), 2.63 (br d, 1H), 2.51 (m, 2H), 1.58 (m, 2H), 1.51 (s, 9H), 0.92 (t, 3H).

Step C: Preparation of methyl 3-chloro-4-(3-(t- tert-butoxycarbonyl-2-(R,S)-phenyl-4-propyl-5-tetrahydroiso-[3,6]-quinolinoxy)propylthio) phenyl acetate 100 mg (0.27 mmole, 1.0 eq) of 1-tert-butoxycarbonyl-2-(R,S)-phenyl-4-propyl-5-hydroxy tetrahydroiso-[3,6]-quinoline from Example 14, step B was stirred with 3 ml N,N-dimethylformamide, 93 mg (0.29, 1.05 eq.) cesium carbonate and 92 mg (0.27 mmole, 1.0 eq.) of methyl 3-chloro-4-(3-bromopropylthio) phenyl acetate from example 12, step F at 60° C. for one hour. The reaction mixture was then cooled to room temperature, diluted with ethyl acetate, washed twice with dilute HCl, dried over sodium sulfate, filtered and the filtrate evaporated. The crude residue was purified by silica gel chromatography to give 126 mg (74% yield) of the title compound.

1H NMR (500 MHz, CDCl₃): δ7.34 (d, 1H), 7.31–7.21 (m, 6H), 7.15 (dd, 1H), 6.80 (br s, 1H), 6.63 (s, 1H), 4.11 (m, 3H), 3.72 (s, 3H), 3.59 (s, 2H), 3.18 (t, 2H), 3.12 (m, 1H), 2.94 (br, 1H), 2.69 (br, 1H), 2.52 (m, 2H), 2.19 (m, 2H), 1.59 (m, 2H), 1.51 (s, 9H), 0.90 (t, 3H).

Step D: Preparation of methyl 3-chloro-4-(3-(2-(R,S)-phenyl-4-propyl-5-tetrahydroiso-[3,6]-quinolinoxy) propylthio) phenyl acetate 125 mg (0.20 mmole, 1.0 eq) of methyl 3-chloro-4-(3-(1-tert-butoxycarbonyl-2-(R,S)-phenyl-4-propyl-5-tetrahydroiso-[3,6]-quinolinoxy)propylthio) phenyl acetate from Example 14, step C was dissolved in 1 ml of 4N HCl in dioxane. After 75 minutes a white solid was noted in the flask, so diethyl ether was added and the solid filtered. The solid was collected in a flask and pumped on high vacuum to give 100 mg (89% yield) of the title compound.

1H NMR (500 MHz, CDCl₃): δ7.40 (m, 5H), 7.34 (d, 1H), 7.30 (d, 1H), 7.15 (dd, 1H), 6.60 (s, 1H), 6.51 (s, 1H), 5.37 (br, 1H), 4.10 (t, 2H), 3.72 (s, 3H), 3.59 (s, 2H), 3.28 (br, 1H), 3.18 (t, 2H), 3.00 (br, 1H), 2.45 (t, 2H), 2.18 (m, 2H), 1.67 (br, 2H), 1.46 (m, 2H), 0.90 (t, 3H).

Step E: Preparation of methyl 3-chloro-4-(3-(1-benzoyl-2-(R,S)-phenyl-4-propyl-5-tetrahydroiso-[3,6]-quinolinoxy) propylthio) phenyl acetate 19 mg (34 μmole, 1.0 eq.) of methyl 3-chloro-4-(3-(2-(R, S)-phenyl-4-propyl-5-tetrahydroiso-[3,6]-quinolinoxy) propylthio) phenyl acetate from Example 14, step D was dissolved in 400 μl of dichloromethane. 13.5 μl (170 μmole, 5.0 eq.) of pyridine and 8 μl (68 μmole, 2.0 eq.) of benzoyl chloride were added and the reaction was stirred for 16 hours under nitrogen atmosphere. The reaction mixture was directly chromatographed on silica gel to give 15.9 mg (75% yield) of the title compound.

$^1$H NMR (500 MHz, CDCl$_3$): δ7.42 (m, 5H), 7.32 (m, 6H), 7.16 (dd, 1H), 7.03 (br s, 1H), 6.88 (br s, 1H), 6.64 (br s, 1H), 4.12 (br, 2H), 3.72 (s, 3H), 3.59 (s, 2H), 3.30 (br, 1H), 3.19 (t, 2H), 2.98 (br, 2H), 2.70–2.50 (br, 4H), 2.20 (m, 2H), 1.58 (m, 2H), 0.91 (t, 3H).

Step F: Preparation of 3-chloro-4-(3-(1-benzoyl-2-(R,S)-phenyl-4-propyl-5-tetrahydroiso-[3,6]-quinolinoxy) propylthio) phenylacetic acid 14.9 mg (24 μmole, 1.0 eq.) of methyl 3-chloro-4-(3-(1-benzoyl-2-(R,S)-phenyl-4-propyl-5-tetrahydroiso-[3,6]-quinolinoxy)propylthio) phenyl acetate from Example 14, step E was dissolved in 0.30 ml of 1:1 methanol:tetrahydrofuran. Added 0.15 ml (37.5 μmole, 1.6 eq.) of 0.25N sodium hydroxide and allowed to stir for 45 minutes. Water was added, as was ethyl acetate followed by dilute aqueous HCl (enough to acidify aqueous layer). The organic layer was separated and dried over sodium sulfate, filtered and the filtrate was evaporated to give 14.6 mg (99% yield) of the title compound. The title compound gives a broad NMR in CDCl$_3$.

$^1$H NMR (500 MHz, CDCl$_3$): δ7.45–7.20 (m, 11H), 7.04 (br, 2H), 6.87 (s, 1H), 6.58 (s, 1H), 4.11 (br, 2H), 3.64 (br, 1H), 3.58 (s, 2H), 3.26 (br m, 2H), 3.16 (br m, 1H), 2.98 (br m, 1H), 2.66 (br, 1H), 2.56 (br, 2H), 2.20 (m, 2H), 1.58 (m, 2H), 0.91 (br, 3H).

MS (ESI; TFA/HCOONH$_4$): 614.4 m/e [M+1].

EXAMPLE 15 sphere (1 Atm) for 2 hours. The mixture was then filtered through a celite pad and the solvent removed in vacuo to give tan solid. This was chromatographed on silica gel using 20% ethyl acetate in hexane to give the titled compound.

NMR (CDCl3) δ7.46 (d,1H, J=6.88 Hz); 6.80 (d, 1H, J=8.83 Hz); 6.60 (s, 1H); 5.70(bs, 1H); 2.81 (t, 2H, J=7.61 Hz); 1.62 (m, 2H); 0.98(t, 3H, J=7.36 Hz).

STEP B: Preparation of Methyl 3-chloro-4-(4-bromobutyloxy)-phenylacetate

To a solution of methyl 3-chloro-4-hydroxyphenylacetate and 1,4-dibromobutane (0.021 g, 0.044 mmol) in 0.5 mL of methanol was added 5N NaOH soln (0.04 mL, 5 eq) at rt. The reaction mixture was heated initially with a heat gun to reflux in order to dissolve the starting material. After heating, the reaction mixture stirred at ambient temperature for 1 h. The reaction mixture was diluted with EtOAc and 0.1N HCl (5 mL). The organic layer was separated from the aqueous portion, and washed with 0.1N HCl (5 mL) followed by 10 mL brine. The organic layer was dried (MgSO$_4$), filtered, and evaporated in vacuo to afford the title compound. This compound was taken forward without further purification.

NMR (CDCl$_3$) δ7.28 (m, 1H); 7.12 (m, 1H); 6.84(d, 1H); 4.06 (t, 2H, J=5.82 Hz); 3.68 (s, 3H);3.47 (m, 4H); 2.14 (m 2H); 2.03 (m, 2H).

STEP C: Methyl 3-chloro-4-(4-(4-trifluoromethyl-8-propyl-coumarinyl-7-oxy)butyloxy)phenylacetate A solution of methyl 3-propyl-4-hydroxyphenylacetate (0.10 grams), methyl 3-chloro-4-(4-bromobutyloxy) phenylacetate and 4-trifluoromethyl-8-propyl-7-hydroxycoumarin and potassium carbonate (0.07 grams) in 2-butanone (4 mL). The mixture was refluxed overnight. The reaction mixture was cooled to room temperature and partitioned between isopropyl acetate and pH 4 buffer. The organic layer was separated, washed with water, dried over MgSO4, and concentrated. Column Chromatography (silica gel 60, 50% methylene chloride in hexane) gave the title

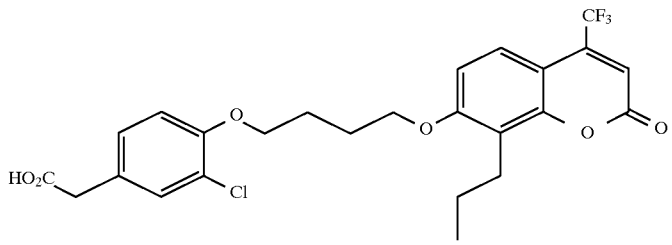

3-chloro-4-(4-(4-trifluoromethyl-8-propyl-coumarinyl-7-oxy)butyloxy)phenylacetic acid STEP A: Preparation of 4-trifluoromethyl-8-propyl-7-hydroxycoumarin To a solution of 4-trifluoromethyl-7-hydroxycoumarin (5.0 grams, 22.0 mmol) and potassium carbonate(3.6 grams, 26.0 mmol) in DMF (20.0 mL) at 40° C., was added 3-bromoprop-1-ene (2.0 mL, 23.0 mmol). This mixture was stirred 18 hours and then diluted with ethyl acetate. The organic phase was washed with 1M hydrochloric acid solution and brine. The organic was then dried over sodium sulfate and the solvent removed to give a tan solid. This was filtered through a pad of silica gel using 20% ethylacetate in hexane. This material was then dissolved in 1,2-dichlorobenzene (150 mL) and refluxed for 18 hours. The solvent was removed in vacuo to give a tan solid. This material was dissolved in methanol (150 mL) with 10% palladium on carbon (300.0 mg) under a hydrogen atmocompound. This compound was filtered through a pad of silica gel using ethyl acetate and hexane (1:2) as the mobile phase, and taken forward without further purification.

STEP D: Preparation of 3-chloro-4-(4-(4-trifluoromethyl-8-propyl-coumarinyl-7-oxy)butyloxy)phenylacetic acid Using the method of saponification described in example 2, substituting methyl 3-chloro-4-(4-(4-trifluoromethyl-8-propyl-coumarinyl-7-oxy)butyloxy)phenylacetate as the starting material, the titled compound was obtained.

NMR (CDCl$_{13}$) δ7.52 (d,1H, J=7.07 Hz); 7.28 (m, 2H); 7.10 (m, 2H); 6.87(t, 2H, J=9.77 Hz); 6.58 (s, 1H); 4.17 (t, 2H, J=5.82 Hz); 4.09 (t, 2H, J=5.74 Hz); 3.55 (s, 2H); 2.79 (t, 2H, J =7.48 Hz); 2.06 (m, 4H); 1.56 (m, 2H); 0.93 (t, 3H, J =7.44 Hz).

ESI: Mass spec: m/e=513 (M+1).

EXAMPLE 16

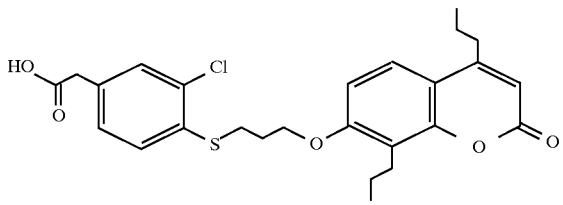

3-Chloro-4-(3-(4, 8-dipropyl-coumarinyl-7-oxy) propylthio) phenylacetic acid

Step A: Preparation of 7-hydroxy-4,8-dipropylcoumarin

The titled compound was prepared according to the method described in Example 15, Step A, substituting 7-hydroxy-4-propylcoumarin for 4-trifluoromethyl-7-hydroxycoumarin.

$^1$H NMR (400 MHz, CDCl$_3$, ppm): δ0.98 (t, J=7.0 Hz, 3H), 1.30 (t, J=7.0 Hz, 3H), 1.60–1.78 (m, 4H), 2.70–2.85 (m, 4H), 6.15 (s, 1H), 6.74 (d, J=8.7 Hz, 1H), 7.33 (d, J=8.7 Hz, 1H)

Step B: Preparation of methyl 3-chloro-4-(3-bromopropylthio)-phenylacetate

Same procedure and starting material as described in Example 11, Step A.

Step C: Preparation of methyl 3-chloro-4-(3-(4.8-dipropyl-coumarinolyl-7-oxy)propylthio)phenylacetate Same procedure as described in Example 11, Step D using 7-hydroxy-4,8-di propylcoumarine.

$^1$H NMR (400 MHz, CDCl$_3$, ppm): δ7.34 (m, 3H), ), 7.18 (dd, J=1.9, 8.1 Hz, 1H), 6.80 (d, J=8.9 Hz, 1H), 6.12 (s, 1H), 4.24 (t, J=5.8 Hz, 2H), 3.68 (s, 3H), 3.54 (s, 2H), 1.02(t, J=7.3 Hz, 3H), 0.93(t, J=7.3 Hz, 3H), Step D: Preparation of 3-Chloro-4-(3-(4, 8-dipropyl-coumarinolyl-7-oxy)propylthio) phenylacetic acid.

Same procedure as described in Example 11, Step E, using methyl 3-chloro-4-(3-(4,8-dipropyl-coumarinolyl-7-oxy)propylthio)-phenylacetate. $^1$H NMR (400 MHz, CDCl$_3$, ppm): δ7.34 (m, 3H),), 7.18 (dd, J=1.9, 8.1 Hz, 1H), 6.80 (d, J=8.9 Hz, 1H), 6.12 (s, 1H), 4.24 (t, J=5.8 Hz, 2H), 3.68 (s, 3H), 3.54 (s, 2H), 1.02(t, J=7.4 Hz, 3H), 0.92(t, J=7.4 Hz, 3H), ESI: MS: m/e=489 (M+)

EXAMPLE 17

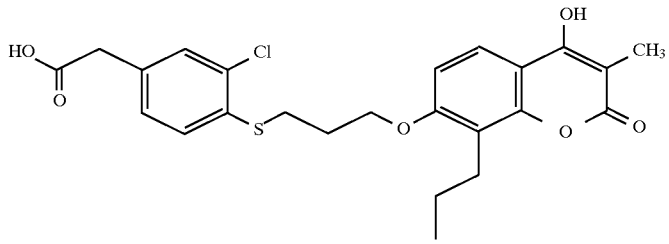

3-chloro-4-(3-(3-methyl-4-hydroxy-7-propyl-6-coumarinyloxy)-propylthio) phenyl acetic acid 1. Ethyl 2,2-difluoropropionate Neat ethyl pyruvate (5.026 grams; 43.283 mmol) was placed in a flask and cooled to 0° C. The ester was treated dropwise with DAST (11.72 mL; 88.730 mmol). The reaction was stirred for 15 min, then allowed to warm to 20° C. and stirred for 2 hr. The reaction was transferred to a dropping funnel and added dropwise to a mixture of methylene chloride and water. The two phases were separated and the organic dried over magnesium sulfate. The solvent was removed in vacuo and the title compound was used without further purification.

NMR (CDCl$_3$): 4.30 (quart, 2H, J=7.1 Hz); 1.78 (t, 3H, J=18.8 Hz);
1.33 (t, 3H, J=7.2 Hz).

2. 2,2-difluoropropionic acid

A solution of ethyl 2,2-difluoropropionate (5.169 grams; 33.983 mmol) in THF (35 mL) was treated with a solution of sodium hydroxide in water (2.5N; 36 mL; 90.00 mmol). The mixture was refluxed for 1 hour. The reaction mixture was cooled to 20° C. and partitioned between MTBE and water. The organic was discarded and the pH of the aqueous was adjusted to 0.5 with con. HCl. The aqueous was extracted with methylene chloride, which was dried, filtered and evaporated in vacuo to afford a residue. The residue was distilled at atmospheric pressure. The fraction boiling at 140°–144° C. was collected (2.322 grams), affording the title compound.

NMR (CDCl$_3$): 1.83 (t, J=18.8 Hz).

3. 2,2-difluoropropionyl chloride

A solution of 2,2-difluoropropionic acid (2.322 grams; 21.098 mmol) in dry 1,1,2-trichloroethane (15 mL) was cooled to 0° and treated with a solution of oxalyl chloride (2.02 mL; 23.207 mmol) in 1,1,2-trichloroethane (5 mL). The reaction was allowed to stir and warm slowly for 16 hours. The reaction mixture was fractionally distilled.

The fraction boiling at 44°–48° C. was collected (1.902 grams), affording the title compound.

NMR (CDCl$_3$): 1.89 (t, J=18.3 Hz).

4. 2,4-dihydroxy-3-propyl-α,α-difluoropropiophenone 2-propylresorcinol (2.478 grams; 16.280 mmol) was suspended in 0° C. 1,2-dichloroethane (20 mL). Aluminum chloride (1.973 grams; 14.800 mmol) was added and the suspension was stirred for 10 minutes. A solution of 2,2-difluoropropionyl chloride (1.902 grams; 14.800 mmol) in 1,2-dichloroethane (6 mL) was added dropwise to the suspension. The now homogenous reaction was stirred at 0° C. for 30 minutes, then allowed to warm to 20° C. and stirred 3 hours. The reaction was added dropwise to a vigorously stirred mixture of methylene chloride and 0.1N HCl. The organic was recovered and washed once with 0.1N HCl and once with water. The organic was dried over magnesium sulfate, filtered and concentrated to a residue which was chromatographed over silica gel to afford the title compound.

NMR (CDCl$_3$): 7.83 (dt, 1H, J=9.0, 2.1 Hz); 6.37 (d, 1H, J=9.1 Hz); 5.36 (bs, 1H); 2.61 (bt, 2H, J=7.7 Hz); 1.87 (t, 3H, J=19.4 Hz).

5. 3-Methyl-4-acetoxy-6-hydroxy-7-propyl-coumarin

A solution of 2,4-dihydroxy-3-propyl-α,α-difluoropropiophenone (0.280 grams; 1.146 mmol) in dry methanol (4 mL) was treated with anhydrous sodium acetate (0.470 grams; 5.732 mmol) and hydroxylamine hydrochloride (0.398 grams; 5.732 mmol). The mixture was refluxed for 36 hours. The reaction was partitioned between isopropyl acetate and pH 7 buffer. The organic was washed once with water and dried over magnesium sulfate. Filtration and evaporation afforded a residue (0.345 grams) which was dissolved in acetic anhydride (5 mL). The solution was stirred for 2 hours. The solvent was removed in vacuo and the reaction flushed once with toluene. The residue was dissolved in dry pyridine (5 mL) and refluxed for 3 hours. The reaction was cooled to 20° C. and the pyridine removed under high vacuum. The residue was partitioned between isopropyl acetate and 0.1N HCl. The organic was dried over magnesium sulfate, filtered and concentrated to an oil. Silica gel chromatography afforded the title compound.

NMR (CDCl$_3$): 7.35 (d, 1H, J=8.6 Hz); 6.86 (d, 1H, J=8.5 Hz); 5.32 (vbs, 1H); 2.89 (bt, 2H, J=7.7 Hz); 2.54 (s, 3H); 2.03 (s, 3H);

6. Methyl 3-chloro-4-(3-(3-methyl-4-acetoxy-7-propyl-6-coumarin) oxy) propylthio phenyl acetate A solution of 3-methyl-4-acetoxy-6-hydroxy-7-propyl coumarin (0.069 grams; 0.250 mmol) in dry DMF (2 mL) was treated with methyl 3-chloro-4-(3-bromopropyl)thiophenyl acetate (0.093 grams; 0.275 mmol). Cesium carbonate (0.090 grams; 0.275 mmol) was added and the mixture stirred for 16 hours. The reaction was partitioned between isopropyl acetate and pH 4 buffer. The organic was washed once with water, dried over magnesium sulfate, filtered and evaporated to an oil. Silica gel chromatography afforded the title compound.

NMR (CDCl$_3$): 7.43 (d, 1H, J=8.8 Hz); 7.31 (d, 1H, J=1.9 Hz); 7.27 (d, 1H, J=8.1 Hz); 7.12 (dd, 1H, J=8.1, 1.9 Hz); 6.97 (d, 1H, J=8.9 Hz); 4.21 (t, 2H, J=5.8 Hz); 3.68 (s, 3H); 3.16 (t, 2H, J=7.1 Hz); 2.90 (bt, 2H, J=7.6 Hz); 2.54 (s, 3H); 2.04 (s, 3H).

7. Methyl 3-chloro-4-(3-(3-methyl-4-hydroxy-7-propyl-6-coumarinyl oxy) propylthio phenyl acetate A solution of methyl 3-chloro-4-(3-(3-methyl-4-acetoxy-7-propyl-6-coumarin)oxy) propylthio phenyl acetate (0.015 grams; 0.028 mmol) in dry methanol (0.500 mL) was treated with a solution of sodium methoxide in methanol (0.50M; 0.056 mL; 0.028 mmol). The solution was stirred for 16 hours. The reaction was partitioned between isopropyl acetate and 0.1N HCl. The organic was dried over magnesium sulfate, filtered and concentrated to afford the title compound.

NMR (CDCl$_3$): 8.96 (s, 1H); 7.42 (d, 1H, J=8.8 Hz); 7.30 (d, 1H, J=1.9 Hz): 7.27 (d, 1H, J=8.1 Hz); 7.12 (dd, 1H, J=8.1, 1.8 Hz); 6.54 (d, 1H, J=8.8 Hz); 4.13 (t, 2H, J=5.8 Hz); 3.68 (s, 3H); 3.15 (t, 2H, J=7.1 Hz); 2.72 (bt, 2H, J=7.7 Hz); 2.66 (s, 3H);

8. 3-chloro-4-(3-(3-methyl-4-hydroxy-7-propyl-6-coumarinyloxy) propylthio phenyl acetic acid A solution of methyl 3-chloro-4-(3-(3-methyl-4-hydroxy-7-propyl-6-coumarin)oxy)propylthio phenyl acetate (0.010 grams; 0.019 mmol) in dry methanol (0.500 mL) was treated with a solution of LiOH in water (1.090M; 0.035 mL; 0.036 mmol). The solution was refluxed for 2 hours. The reaction was partitioned between isopropyl acetate and 0.1N HCl. The organic was dried over magnesium sulfate, filtered and concentrated to afford the title compound as an oil which crystallized on standing.

NMR (CDCl$_3$): 8.96 (vbs, 1H); 7.41 (d, 1H, J=8.8 Hz); 7.31 (d, 1H, J=1.9 Hz); 7.27 (d, 1H, J=8.1 Hz); 7.12 (dd, 1H, J=8.1, 1.9 Hz); 6.53 (d, 1H, J=8.8 Hz); 4.13 (t, 2H, J=5.7 Hz); 3.58 (s, 2H); 3.15 (t, 2H, J=7.1 Hz); 2.72 (bt, 2H, J=7.6 Hz); 2.65 (s, 3H).

EXAMPLE 18

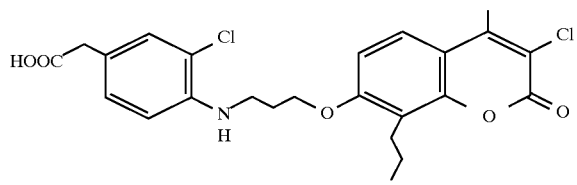

3-chloro-4-(3-(3-chloro-4-methyl-8-propyl-coumarinyl-7-oxy)propylamino)phenylacetic acid STEP A: Preparation of 3-chloro-4-methyl-8-propyl-7-hydroxycoumarin Using the method in example 15 step A, substituting 3-chloro-4-methyl-7-hydroxycoumarin as the starting materials, the titled compound was obtained.

NMR (CDCl$_3$) δ7.38 (d,1H, J=6.88 Hz); 6.85 (d, 1H, J=8.83 Hz); 5.63 (bs, 1H); 2.81 (t, 2H, J=7.61 Hz); 2.55 (s, 3H); 1.62 (m, 2H); 0.98(t, 3H, J=7.36 Hz).

STEP B: Preparation of Methyl 3-chloro-4-(3-bromopropylamino)-phenylacetate

Step 1: Preparation of 3-chloro-4-acetamidophenylacetic acid

Acetic anhydride (152 mL, 1.6 moles) was added dropwise to a rapidly stirring mixture of 4-aminophenylacetic acid (195 grams, 1.3 moles) in acetic acid (600 mL) and water (250 mL) at room temperature. After a slight exotherm, the dark brown solution was stirred for one hour at room temperature. The solution was diluted with ethanol (500 mL) and water (250 mL), and a suspension of Calcium hypochlorite (340 grams, 2.3 moles) in water (1L plus 500 mL rinse) was added portionwise. The temperature rose to 50° C. and the mixture was stirred for 16 hours at room temperature. The mixture was poured into ice-water (8 L) and extracted with ethyl acetate (3×2 L). The combined extracts were washed with saturated brine, dried over magnesium sulfate and concentrated in vacuo to a small volume. Hexane was added and the resulting precipitate filtered, washed with hexane and dried to give the title compound (180 grams) as a brown solid NMR (CDCl$_3$+10% CD$_3$OD): δ2.12 (s, 3H); 3.45 (s, 2H); 7.10 (dd, 2H)); 8.02 (dd, 1H).

Step 2: Preparation of methyl 3-chloro-4-aminophenylacetate.HCl

A solution of 3-chloro-4-acetamidophenylacetic acid (180 grams, 0.79 moles) in methanol (2 L), was treated with concentrated HCl (200 mL) and the resulting solution refluxed for 6 hours and then stirred at room temperature for 16 hours. The mixture was concentrated in vacuo to about one-half its volume and ether (4 L) was added. The resulting precipitate was filtered, washed with ether and dried to give the title compound (173 grams) as a tan solid NMR, (CD$_3$OD): δ3.70 (s, 2H); 3.73 (s, 3H); 7.35 (d, 1H); 7.43 (d, 1H); 7.56 (s, 1H).

Step 3: Preparation of methyl 3-chloro-4-(3 bromopropylamino)-phenylacetate

Magnesium oxide (10 grams, 250 mmoles), was added to a solution of 1,3-dibromopropane (139 grams, 70 mL, 700 mmoles) in dimethylacetamide (150 mL). A solution of methyl 3-chloro-4-aminophenylacetate.HCl (23.6 grams, 100 mmoles) in dimethylacetamide (200 mL) was added dropwise over 30 minutes and the mixture stirred at 80° C. for 6 hours. The cooled mixture was partitioned with methylene chloride and water. The aqueous phase was extracted with methylene choride and the combined organic phases washed with brine, dried over magnesium sulfate and concentrated in vacuo to an oil. The crude product was chromatographed on a silica gel column eluting with hexane-:ethyl acetate (9:1). The product was further purified by a second silica gel chromatography in methylene chloride-:hexane (2:3) to give the title compound as an oil. NMR, (CDCl$_3$): δ2.15 (qnt, 2H); 3.35 (q, 2H); 3.47 (s,2H); 3.49 (t, 2H); 3.67 (s, 3H); 6.63 (d, 1H); 7.03 (dd, 1H); 7.17 (d, 1H).
STEP C: Methyl 3-chloro-4-(3-(3-chloro-4-methyl-8-propyl-coumarinolyl-7-oxy)propylamino)phenylacetate Using the method in example 15 step C substituting Methyl 3-chloro-4-(3-bromopropylamino)phenylacetate and 3-chloro-4-methyl-8-propyl-7-hydroxycoumarin as the starting materials, the titled compound was obtained.

NMR (CDCl$_3$) δ7.41 (d,1H, J=8.91 Hz); 7.17 (s, 1H); 7.02 (d, 1H, J=8.32 Hz); 6.85 (d, 1H, J=8.95 Hz); 6.63 (d, 1H, J=8.34 Hz); 4.39 (bs, 1H); 4.15 (t, 2H, J=5.86 Hz); 3.66 (s, 3H); 3.47 (s, 2H); 3.42 (t, 2H, J=6.88 Hz); 2.85 (t, 2H, J=7.61 Hz); 2.52 (s, 3H); 2.16 (m, 2H); 1.57 (m, 2H); 0.94 (t, 3H, J=7.36 Hz).
STEP D: 3-chloro-4-(3-(3-chloro-4-methyl-8-propyl-coumarinyl-7-oxy)propylamino)phenylacetic acid A solution of Methyl 3-chloro-4-(3-(3-chloro-4-methyl-8-propyl-coumarinolyl-7-oxy)propylamino)phenylacetate (0.113 grams) in methanol (1.5 mL) was treated with a solution of lithium hydroxide in water (1.01M; 0.362 mL). The reaction was refluxed 1 hour. The reaction mixture was partitioned between isopropyl acetate and 0.1N HCl. The organic was dried over magnesium sulfate, filtered and concentrated to a solid. The solid was suspended in methylene chloride/cyclohexane (1:1; 2 mL). The mixture was refluxed briefly and cooled to 0° C. The title compound was isolated by filtration.

NMR (CDCl$_3$) δ7.41 (d,1H, J=8.91 Hz); 7.18 (s, 1H); 7.03 (d, 1H, J=8.32 Hz); 6.85 (d, 1H, J=8.95 Hz); 6.63 (d, 1H, J=8.34 Hz); 4.39 (bs, 1H); 4.15 (t, 2H, J=5.86 Hz); 3.66 (s, 3H); 3.50 (s, 2H); 3.42 (t, 2H, J=6.88 Hz); 2.85 (t, 2H, J=7.61 Hz); 2.52 (s, 3H); 2.16 (m, 2H); 1.57 (m, 2H); 0.94 (t, 3H, J=7.36 Hz).
ESI: Mass spec: m/e=477 (M$^+$).

EXAMPLE 19 concentrated in vacuo. Column Chromatography (silica gel 60, 50% methylene chloride in hexane) gave the title compound.
$^1$H NMR(400 MHz, CDCl$_3$): δ7.58 (d, 1H, J=9.0 Hz), 7.38 (m, 5H), 6.45 (d, 2H, J=9.1 Hz), 5.13 (s, 2H), 2.75 (s, 2H), 2.67 (t, 2H, J=7.6 Hz), 1.57 (hex, 2H, J=7.6 Hz), 1.04 (s, 9H), 0.93 (t, 3H, J=7.4 Hz).
Step B: Preparation of 7-benzyloxy-4-tert-butylmethyl-8-propylcoumarin 4-benzyloxy-2-hydroxy-3-propyl-3,3-dimethylbutyrophenone (2.12 G) was combined with methyl (tyiphenyl-phosphoranylidene)acetate (6.25 G) in tolune (15 mL) and refluxed for two days. The reaction was cooled and the product was purified by flash chromatography on silica gel (gradient elution: 5% then 10% then 15% ethyl acetate/hexane) to provide the title compound.
$^1$H NMR(400 MHz, CDCl$_3$): δ7.47 (d, 1H, J=9.0 Hz), 7.40 (m, 5H), 6.85 (d, 2H, J=9.0 Hz), 6.06 (s, 1H), 5.15 (s, 2H), 2.88 (t, 2H, J=7.7 Hz), 2.63 (s, 2H), 1.62 (hex, 2H, J=7.6 Hz), 0.98 (s, 9H), 0.96 (t, 3H, J=7.7 Hz).
Step C: Preparation of 4-tert-butylmethyl-7-hydroxy-8-propylcoumarin A solution of 7-benzyloxy-4-tert-butyl-8-propylcoumarin (718 mg) in ethyl acetate (25 mL) was treated with 10% palladium (107 mg) on carbon. The mixture was shaken under a hydrogen atmosphere (40 psi) for six hours. The mixture was filtered through Celite and concentrated to get the title compound.
$^1$H NMR(400 MHz, CDCl$_3$): δ7.49 (d, 1H, J=9.1 Hz), 6.88 (d, 2H, J=9.0 Hz), 6.05 (s, 1H), 5.15 (s, 1H), 2.83 (t, 2H, J=7.6 Hz), 2.64 (s, 2H), 1.62 (hex, 2H, J=7.6 Hz), 0.98 (s, 9H), 0.96 (t, 3H, J=7.7 Hz).
Step D: Preparation of 7-(3-bromopropoxy)-4-tert-butylmethyl-7-hydroxy-8-propylcoumarin A solution of 4-tert-butyl-7-hydroxy-8-propylcoumarin (380 mg), 1,3-dibromopropane (0.45 ml) and potassium carbonate (240 mg) in 2-butanone (15 ml) was refluxed for five hours. The mixture was partioned between 0.2N HCl and ethyl acetate, dried over magnesium sulfate and concentrated. Column Chromatography (silica gel 60, 50% methylene chloride in hexane) gave the title compound.
$^1$H NMR(400 MHz, CDCl$_3$): δ7.51 (d, 1H, J=9.0 Hz), 6.86 (d, 2H, J=9.0 Hz), 6.07 (s, 1H), 4.19 (t, 2H, J=5.7 Hz),

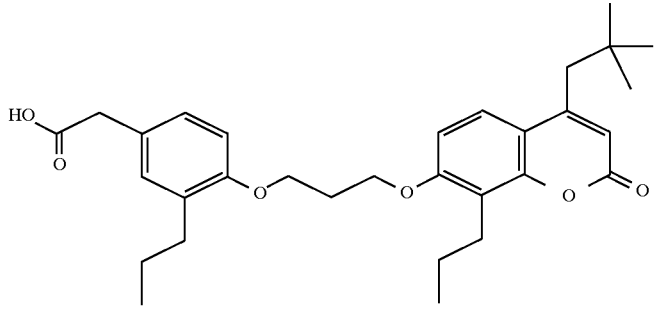

3-Propyl-4-(3-(4-tert-butylmethyl-8-propyl-coumarinyl-7-oxy)-propylthio)phenylacetic acid
Step A: Preparation of 4-benzyloxy-2-hydroxy-3-propyl-3,3-dimethylbutyrophenone To a solution of 2,4-dihydroxy-3-propyl-3,3-dimethylbutyrophenone (1.5 g) and benzyl bromide (0.86 mL) in 15 mL of 2-butanone was added potassium carbonate (1.08 g). The mixture was refluxed for five hours wherein it was partioned between 0.2N Hcl and ethyl acetate. The organic layer was dried over magnesium sulfate, filtered, 3.63 (t, 2H, J=6.3 Hz), 2.83 (t, 2H, J=7.6 Hz), 2.64 (s, 2H), 2.36 (quint, 2H, J=5.8 Hz), 1.61 (hex, 2H, J=7.6 Hz), 0.99 (s, 9H), 0.98 (t, 3H, J=7.5 Hz).
Step E: Preparation of methyl 3-propyl-4-(3-(4-tert-butylmethyl-8-propyl-coumarinolyl-7-oxy)propylthio) phenyl-acetate A solution of 7-(3-bromopropoxy)-4-tert-butylmethyl-7-hydroxy-8-propylcoumarin (100 mg), 3-propyl-4-hydroxyphenylacetate (47 mg) and potassium carbonate (30 mg) in 2-butanone (10 ml) was refluxed for ten hours. The mixture was partioned between 0.2N HCl and ethyl acetate, dried over magnesium sulfate and concentrated. Column Chromatography (silica gel 60, 50% methylene chloride in hexane) gave the title compound.

$^1$H NMR(400 MHz, CDCl$_3$): δ7.48 (d, 1H, J=8.9 Hz), 7.04 (m, 2H), 6.81 (m, 2H), 6.05 (s, 1H), 4.24 (t, 2H, J=6.1 Hz), 4.14 (t, 2H, J=6.0 Hz), 3.65 (s, 3H), 3.52 (s, 2H), 2.80 (t, 2H, J=7.6 Hz), 2.63 (s, 2H), 2.53 (t, 2H, J=7.4 Hz), 2.30 (quint, 2H, J=5.9 Hz), 1.55 (m, 4H), 0.97 (s, 9H), 0.94–0.85 (m, 6H).

Step F: Preparation of 3-propyl-4-(3-(4-tert-butylmethyl-8-propyl-coumarinolyl-7-oxy)propylthio)phenylacetic acid A solution of methyl 3-propyl-4-(3-(4-tert-butyl-8-propyl-coumarinolyl-7-oxy)propylthio)phenyl-acetate (19 mg) in methanol (3 mL) was treated with a solution of LiOH in water (1.0M, 0.32 mL). The solution was refluxed for 1 hour. The solution was partitioned between isopropyl acetate and 0.2N HCl. The organic layer was separated, washed with water, dried over MgSO4, and concentrated to afford the title compound.

1H NMR(400 MHz, CDCl$_3$): δ7.47 (d, 1H, J=8.9 Hz), 7.04 (m, 2H), 6.81 (m, 2H), 6.05 (s, 1H), 4.24 (t, 2H, J=6.1 Hz), 4.14 (t, 2H, J=6.0 Hz), 3.52 (s, 2H), 2.80 (t, 2H, J=7.6 Hz), 2.63 (s, 2H), 2.53 (t, 2H, J=7.4 Hz), 2.30 (quint, 2H, J=5.9 Hz), 1.55 (m, 4H), 0.97 (s, 9H), 0.94–0.85 (m, 6H).

ESI: MS m/e=509 (M+1)

EXAMPLE 20

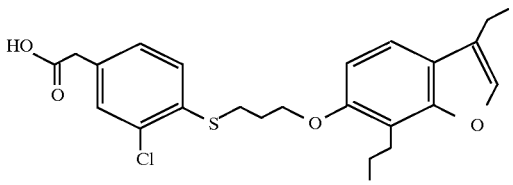

3-Chloro-4-(3-(3-ethyl-7-propylbenzofuran-6-yloxy) propylthio)-phenylacetic acid Step A: Preparation of 3-allyloxy-(2-ethyl-2-oxoethoxy) benzene A solution of 3-allyloxyphenol (1.19 g), 2-bromoacetophenone (1.0 g) and potassium carbonate (1.10 g) in 2-butanone (15 ml) was refluxed for four hours. The mixture was partioned between 0.2N HCl and ethyl acetate. The organic layer was dried over magnesium sulfate, filtered, concentrated in vacuo. Column Chromatography (silica gel 60, 50% methylene chloride in hexane) gave the title compound.

$^1$H NMR(400 MHz, CDCl$_3$): δ7.14 (t, 1H, J=8.5 Hz), 6.52 (m, 1H), 6.45 (m, 2H), 6.01 (m, 1H), 5.39–5.23 (m, 2H), 4.49 (s, 2H), 4.47 (m, 2H), 2.58 (quart, 2H, J=7.4 Hz), 2.13 (s, 2H), 1.06 (t, 3H, J=7.3 Hz).

Step B: Preparation of 2-allyl-3-(2-ethyl-2-oxoethoxy) phenol

A solution of 3-allyloxy-(2-ethyl-2-oxoethoxy) in ortho-dichlorobenzene (15 mL) was refluxed for 24 hours. The reaction was cooled and the product was purified by flash chromatography on silica gel (methylene chloride) to provide the title compound.

$^1$H NMR(400 MHz, CD3COCD3): δ8.29 (s, 1H), 6.95 (t, 1H, J=8.2 Hz), 6.52 (d, 1H, J=7.8 Hz), 6.34 (d, 1H, J=8.3 Hz), 5.90 (m, 1H), 5.04–4.85 (m, 2H), 4.62 (s, 2H), 4.47 (dd, 2H, J=5.0, 1.6 Hz), 2.65 (quart, 2H, J=7.2 Hz), 1.06 (t, 3H, J=7.3 Hz).

Step C: Preparation of 2-propyl-3-(2-ethyl-2-oxoethoxy) phenol

A solution of 2-allyl-3-(2-ethyl-2-oxoethoxy)phenol (480 mg) in ethyl acetate (25 mL) was treated with 10% palladium (75 mg) on carbon catalyst. The mixture was shaken under a hydrogen atmosphere (40 psi) for two hours. The mixture was filtered through Celite and concentrated to get the title compound.

1H NMR(400 MHz, CDCl$_3$): δ6.99 (t, 1H, J=8.2 Hz), 6.49 (d, 1H, J=8.0 Hz), 6.30 (d, 1H, J=8.2 Hz), 4.86 (s, 1H), 4.51 (s, 2H), 2.78 (m, 4H), 1.61 (hex, 2H, J=7.2 Hz), 1.12 (t, 3H, J=7.1 Hz), 0.98 (t, 3H, J=7.3 Hz).

Step D: Preparation of 3-ethyl-6-hydroxy-7-propylbenzofuran

Using the method of Example 5, Step B, using 2-propyl-3-(2-ethyl-2-oxoethoxy)phenol as the starting material, the title compound was obtained.

1H NMR(400 MHz, CDCl$_3$): δ7.29 (s, 1H), 7.19 (d, 1H, J=8.2 Hz), 6.72 (d, 1H, J=8.2 Hz), 4.62 (s, 1H), 2.82 (t, 2H, J=7.6 Hz), 2.64 (quart, 2H, J=7.5 Hz), 1.69 (hex, 2H, J=7.5 Hz), 1.28 (t, 3H, J=7.6 Hz), 0.98 (t, 3H, J=7.4 Hz).

Step E: Preparation of 3-ethyl-6-(3-bromopropyloxy)-7-propylbenzofuran

Using the method of Example 5, Step C, using 3-ethyl-6-hydroxy-7-propylbenzofuran as the starting material, the title compound was obtained.

$^1$H NMR(400 MHz, CDCl$_3$): δ7.31 (s, 1H), 7.26 (d, 1H, J=8.2 Hz), 6.84 (d, 1H, J=8.2 Hz), 4.12 (t, 2H, J=5.9 Hz), 3.64 (t, 2H, J=6.0 Hz), 2.82 (t, 2H, J=7.6 Hz), 2.33 (quint, 2H, J=5.9 Hz), 2.64 (quart, 2H, J=7.5 Hz), 1.69 (hex, 2H, J=7.5 Hz), 1.28 (t, 3H, J=7.6 Hz), 0.93 (t, 3H, J=7.4 Hz).

Step F: Preparation of methyl 3-chloro-4-(3-(3-ethyl-7-propylbenzofuran-6-yloxy)propylthio)-phenylacetate Using the method of Example 5, Step D, using 3-ethyl-6-(3-bromopropyloxy)-7-propylbenzofuran as the starting material, the title compound was obtained.

1H NMR(400 MHz, CDCl$_3$): δ7.30–7.23 (m, 4H), 7.11 (dd, 1H, J=8.4, 1.8 Hz), 6.82 (d, 1H, J=8.5 Hz), 4.12 (t, 2H, J=5.7 Hz), 3.68 (s, 3H), 3.54 (s, 2H), 3.16 (t, 2H, J=7.2 Hz), 2.82 (t, 2H, J=7.5 Hz), 2.64 (quart, 2H, J=7.5 Hz), 2.15 (quint, 2H, J=5.9 Hz), 1.66 (hex, 2H, J=7.5 Hz), 1.28 (t, 3H, J=7.6 Hz), 0.93 (t, 3H, J=7.4 Hz).

Step G: Preparation of 3-chloro-4-(3-(3-ethyl-7-propylbenzofuran-6-yloxy)propylthio)-phenylacetic acid Using the method of Example 6, using methyl 3-chloro-4-(3-(3-ethyl-7-propylbenzofuran-6-yloxy)propylthio)-phenylacetate as the starting material, the title compound was obtained.

$^1$H NMR(400 MHz, CDCl$_3$): δ7.32 (s, 1H), 7.30–7.23 (m, 3H), 7.11 (dd, 1H, J=8.4, 1.8 Hz), 6.82 (d, 1H, J=8.5 Hz), 4.12 (t, 2H, J=5.7 Hz), 3.54 (s, 2H), 3.16 (t, 2H, J=7.2 Hz), 2.82 (t, 2H, J=7.5 Hz), 2.64 (quart, 2H, J=7.5 Hz), 2.15 (quint, 2H, J=5.9 Hz), 1.66 (hex, 2H, J=7.5 Hz), 1.28 (t, 3H, J=7.6 Hz), 0.93 (t, 3H, J=7.4 Hz).

ESI: MS m/e=447 (M+1)

EXAMPLE 21

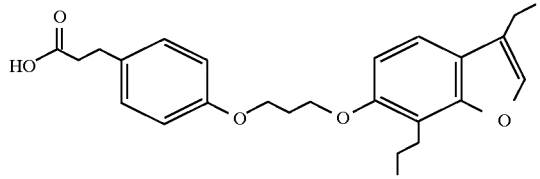

3-(4-(3-(3-ethyl-7-propylbenzofuran-6-yl)oxy) propyloxy)phenyl) propionic acid

To a solution of 3-(3-ethyl-7-propylbenzofuran-6-yl)oxy) propyl bromide (Example 20, step E; 361 mg; 1.11 mmol)

was added methyl 3-(4'-hydroxyphenyl)propanoate (200 mg, 1.11 mmol) and the mixture reacted as described in example 8. step #3. The resulting ester was hydrolyzed and purified using the procedure found in example 8, step #4, providing the title compound.

Characteristic NMR signals (CDCl$_3$, $^1$H NMR, 400 Mhz): δ7.28 (d, 2H, J=12.2 Hz); 7.11 (d, 2H, J=8.5 Hz); 6.84 (apparent t, 3H, J=8.3 Hz); 4.17 (q, 4H, J=5.9 Hz); 2.83 (dt, 4H, J=8.8, 8.0 Hz); 2.63 (m, 4H); 2.26 (m, 2H); 1.62 (m, 2H); 1.28 (t, 3H, J=7.7 Hz); 0.91 (t, 3H, J=7.3 Hz).

MS (ESI) m/e=411 (M+1)

EXAMPLE 22

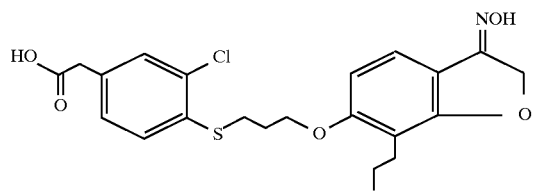

3-Chloro-4-(3-(7-propyl-3-hydroxyimino-2H-benzofuran-6-yloxy)-propylthio)-phenylacetic acid.

Step A: Preparation of methyl 3-chloro-4-(3-bromopropylthio)-phenylacetate

Same procedure and starting material as described in Example 11, Step A.

Step B: Preparation of 6-propenyloxy-(2H-benzofuran-3-one)

This compound was prepared according to the method described in Example 11, Step B using 6-hydroxy-2H-benzofuran-3-one)

$^1$H NMR (400 MHz, CDCl$_3$, ppm) δ7.54(d, 1H, J=8.58), 6.64 (dd, 1H J=8.5, 2.0), 6.52 (d, 1H J=2.1), 6.05–5.97(m, 1H), 5.44–5.31(m, 1H), 4.58 (m, 4H,).

Step C: Preparation of 6-hydroxy-7-propyl-(2H-benzofuran-3-one)

This compound was prepared according to the method described in Example 11, Step C, using 6-propenyloxy-(2H-benzofuran-3-one).

$^1$H NMR (400 MHz, CDCl$_3$, ppm) δ7.40(d, 1H, J=8.40), 6.52 (d, 1H J=4.0), 4.61 (s, 2H), 2.62(t, 2H J=7.4), 1.64–55 (m, 2H), 0.96(t, 3H, J=7.3).

Step D: Preparation of methyl 3-Chloro-4-(3-(7- propyl-2-H-3-oxo-benzofuran-2-yloxy)-propylthio)-phenyl acetate The titled compound was prepared according to the method described in Example 11, Step D, using 6-hydroxy-7-propyl-(2H-benzofuran-3-one)

$^1$H NMR (400 MHz, CDCl$_3$, ppm ) δ7.49–6.08(m, 5H), 4.60(s, 2H), 4.17(t, 2H, J=0.8), 3.68(s, 3H), 3.54(s, 2H), 3.13(t, 2H J=7.0 Hz ), 2.62(t, 2H, J=6.4), 2.16(m, 2H), 1.57(m, 2H), 0.91(t, 3H J=7.3 Hz).

Step E: Preparation of methyl-3-Chloro-4-(3-(7- propyl-3-hydroxyimino-2H-6-benzofuran-6-yloxy)-propylthio)-phenylacetate.

A mixture of methyl 3-Chloro-4-(3-(7- propyl-2H-6-benzoxyfuran-3-one)-propylthio)-phenyl acetate (1.0 mMol), hydroxylamine hydrochloride (5.0 mMol) and sodium acetate (5.0 mMol) in methanol was refluxed for 5 hrs. Reaction was quenched with pH 7 buffer. Stripped off methanol. Extracted with ethyl acetate. The organic layer was washed with water, brine, dried over sodium sulfate, filtered, concentrated in vacuo, and the crude residue was purified by flash chromatography on silica gel (10% ethyl acetate/hexane) to provide the title compound.

$^1$H NMR (400 MHz, CDCl$_3$, ppm ) δ7.99–6.49(m, 5H), 5.16(s, 2H), 4.17(m 2H), 3.68(s, 3H), 3.54(s, 2H), 3.12(t, 2H J=7.0 Hz ), 2.58(t, 2J=6.4), 2.14(m, 2H), 1.54(m, 2H), 0.90(t, 3H J=7.3 Hz).

Step F: Preparation of 3-Chloro-4-(3-(7- propyl-3-hydroxyimino-2H-benzofuran-6-yloxy)- propylthio)-phenylacetic acid The titled compound was prepared according to the method described in Example 11, Step E using methyl-3-Chloro-4-(3-(7-propyl-2H-6-benzoxyfuran-3-oxime)-propylthio)-phenyl acetate.

$^1$H NMR (400 MHz, CDCl$_3$ ppm ) δ6.98–7.97(m, 9H), 4.10(t, 2H J=5.8 Hz), 3.57(s, 2H), 3.19(t, 2H J=7.2 Hz ), 2.02–2.08(m, 2H), 2.20(m, 2H), 1.73(m, 2H), 1.05(t, 3H J=7.4 Hz).

ESI: MS: m/e=450 (M+1)

EXAMPLE 23

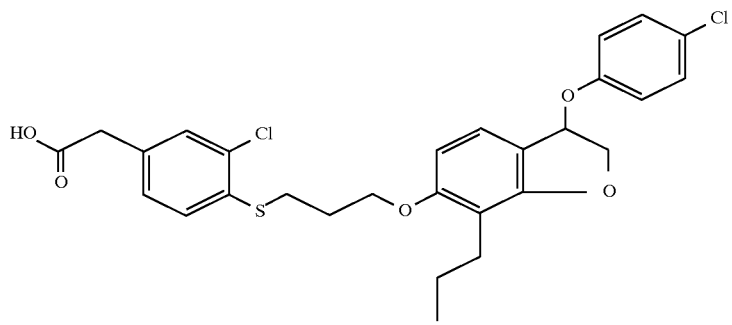

3-Chloro-4-(3-(3-hydroxy-7-propyl-2H-benzofuran-6-yloxy-propylthio)-phenylacetic acid.

Step A: Preparation of methyl-3-Chloro-4-(3-(3-hydroxy-7-propyl-2H-benzofuran-6-yloxy-propylthio)-phenyl acetate.

A solution of methyl 3-Chloro-4-(3-(7- propyl-2H-6-benzoxyfuran-3-one)-propylthio)-phenyl acetate (Step D Example 22) in methanol/THF (2/1) was treated with equivalent amount of NaBH$_4$ at 0° for 1.5 hr. Reaction was quenched with pH 7 buffer. Stripped off methanol/THF. Extracted with ethyl acetate. The organic layer was washed with water, brine, dried over sodium sulfate, filtered, concentrated in vacuo, and the crude residue was purified by thin layer chromatography on silica gel (40% ethyl acetate/hexane) to provide the title compound $^1$H NMR (400 MHz, CD3Cl3, ppm ) δ7.84–6.41(m, 5H), 4.59–4.45(m 2H), 4.11–4.05(m 4H), 3.68(s, 3H), 3.54(s, 2H), 3.18–3.11(m, 4H), 2.86(t, 2H, J=7.6), 2.87–2.50(m, 2H), 2.18–2.12(m, 4H), 1.68–1.42(m, 2H), 0.94(t, 3H J=7.4 Hz).
Step B: Preparation of methyl-3-chloro-4-(3-(3-(4-chlorophenoxy)-7-propyl-2H-benzofuran-6-yloxy-propylthio)-phenyl acetate To a solution of methyl 3-chloro-4-(3-(3-hydroxy-7-propyl-2H-6-benzoxyfuran)-propylthio)-phenyl acetate. (0.313 mmol) in 3 mL DMF was added potassium hydride 35% (0.626 mmol) and allowed to stir at room temperature for ½ hr. Then added 1-Chloro- 4-fluorobenzene (0.939 mmol). This mixture was stirred at room temperature overnight. Reaction was quenched with water. Extracted with ethyl acetate. The organic layer was washed with water, brine, dried over sodium sulfate, filtered, concentrated in vacuo, and the crude residue was purified by thin layer chromatography on silica gel 10% ethyl acetate/hexane) to provide the title compound.

$^1$H NMR (400 MHz, CDCl$_3$, ppm ) δ7.94–6.71(m, 9H), 5.05(s, 2H), 4.16(t 2H, J=6.6), 3.68(s, 3H), 3.54(s, 2H), 3.27(t, 2H J=7.0 Hz ), 2.89(t, 2H J=7.0 Hz ), 2.20–2.17(m, 2H), 1.68–1,66(m, 2H), 1.28–1,26(m, 2H), 0.93(t, 3H J=7.3 Hz).

Step C: 3-Chloro-4-(3-(3-(4-chlorophenoxy)-7-propyl-2H-benzofuran-6-yloxy-propylthio)-phenyl acetic acid The titled compound was prepared according to the method described in Example 11, Step E, using methyl-3-Chloro-4-(3-(3-(4-chlorophenoxy)-7-propyl-2H-6-benzoxyfuran)-propylthio)-phenyl acetate $^1$H NMR (400 MHz, CDCl$_3$, ppm ) δ7.94–6.71(m, 9H), 4.88(s, 2H), 4.16(t 2H, J=6.6), 3.30(s, 2H), 3.27(t, 2H J=7.0 Hz ), 2.89(t, 2H J=7.0 Hz), 2.20–2.17(m, 2H), 1.68–1,66(m, 2H), 1.28–1,26(m, 2H), 0.93(t, 3H J=7.3 Hz).

ESI: MS: m/e=464 (M+NH$_3$)

EXAMPLE 24

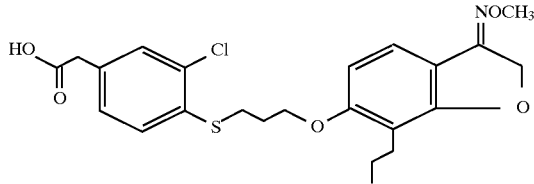

3-Chloro-4-(3-(7- propyl-3-methoxyimino-2H-benzofuran-6-yloxy)-propylthio)-phenylacetic acid Step A: Preparation of methyl 3-Chloro-4-(3-(7- propyl-3-methoxyimino-2H-benzofuran-6-yloxy)-propylthio)-phenyl acetate The titled compound was prepared according to the method described in Example 22, Step E, using methoxylamine hydrochloride $^1$H NMR (400 MHz, CDCl$_3$, ppm) δ7.84–6.42(m, 5H), 5.05(s, 2H), 4.17(m 2H), 3.94(s, 3H), 3.68(s, 3H), 3.54(s, 2H), 3.12(t, 2H J=7.2H 2.56(t, 2H, J=6.4), 2.13(m, 2H), 1.54(m, 2H), 0.90(t, 3H J=7.3 Hz).

Step B: Preparation of 3-Chloro-4-(3-(7-propyl-3-methoxyimino-2H-benzofuran-6-yloxy-)-propylthio)-phenylacetic acid.

The titled compound was prepared according to the method described in Example 11, Step E, using methyl 3-Chloro-4-(3-(7-propyl-2H-6-benzoxyfuran-3-methyloxime)-propylthio)-phenyl acetate $^1$H NMR (400 MHz, CDCl$_3$ ppm ) δ7.84–6.42(m, 5H), 5.05(s, 2H), 4.13(m 2H), 3.94(s, 3H), 3.54(s, 2H), 3.12(t, 2H J=7.2 Hz ), 2.56(t, 2H, J=6.4), 2.13(m, 2H), 1.52(m, 2H), 0.89(t, 3H J=7.3 Hz).

ESI: MS: m/e=464 (M+1)

EXAMPLE 25

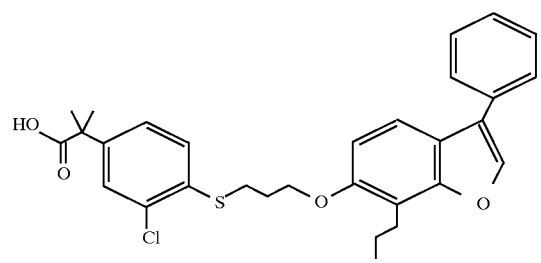

2-methyl-2-(3-chloro-4-(3-(3-phenyl-7-propylbenzofuranyl-6-oxy)propyl)thio)phenyl propionic acid 1. 2-methyl-2-(3-chloro-4-dimethylcarbamoylthio)phenyl propionic acid methyl ester A −78° C. solution of 2-(3-chloro-4-dimethylcarbamoylthio)phenyl propionic acid methyl ester (0.378 grams; 1.25 mmol) in dry THF (4.0 mL) was treated with lithium bis(trimethylsilyl)amide (1.0M; 4.50 mL; 4.50 mmol) dropwise and stirred for 1 hour. The reaction was allowed to warm to −10° C. and stirred for 1 hour, then recooled to −78° C. Methyl iodide (0.093 mL; 1.50 mmol) was added dropwise and stirred for 1 hour. The reaction was warmed to −10° C. and stirred for an additional hour, then partitioned between isopropyl acetate and pH 4.0 buffer. The organic layer was dried over magnesium sulfate, filtered, and concentrated in vacuo to a yellow oil. Silica gel chromatography afforded the title compound as a white crystalline solid.

NMR (CDCl$_3$): 7.53 (d, 1H, J=8.2 Hz); 7.47 (d, 1H, J=2.1 Hz); 7.24 (dd, 1H, J=2.1 Hz); 3.65 (s, 3H); 3.12 (vbs, 3H); 3.03 (vbs, 3H); 1.56 (s, 6H).

2. 2-methyl-2-(3-chloro-4-(3-bromopropyl) thio)phenyl propionic acid methyl ester Sodium methoxide (4.37M; 0.874 mL; 3.82 mmol) in methanol was added to a refluxing solution of 2-methyl-2-(3-chloro-4-dimethylcarbamoylthio) phenyl propionic acid methyl ester (0.403 g; 1.27 mmol) in dry methanol (5.37 mL) and stirred for 2 hours. The reaction was allowed to cool to room temperature and added dropwise to dibromopropane (0.674 mL; 5.08 mmol). The reaction was stirred for 1 hour, then partitioned between isopropyl acetate and pH 4.0 buffer. The organic layer was dried over magnesium sulfate, filtered and concentrated. Silica gel chromatography afforded the title compound.

NMR (CDCl$_3$): 7.35 (d, 1H, J=2.1 Hz); 7.27 (d, 1H, J=8.3 Hz); 7.19 (dd, 1H, J=8.3, 2.1 Hz); 3.66 (s, 3H); 3.55 (t, 2H, J=6.3 Hz); 3.09 (t, 2H, J=7.0 Hz); 2.19 (quint, 2H, J=6.6 Hz); 1.55 (s, 6H).

3. 2-methyl-2-(3-chloro-4-(3-(3-phenyl-7-propylbenzofuran-6-oxy) propyl)thio)phenyl propionic acid methyl ester A solution of 2-methyl-2-(3-chloro-4-(3-bromopropyl) thio)phenyl propionic acid methyl ester (0.051 g; 0.140 mmol) in DMF (1.0 mL) was treated with 3-phenyl-6-hydroxy-7-propylbenzofuran (0.042 g; 0.167 mol). Cesium carbonate (0.060 g; 0.184 mmol) was added. The green solution was stirred for 8 hours, then partitioned between isopropyl acetate and pH 4.0 buffer. The organic layer was washed twice with water, dried over magnesium sulfate, filtered and concentrated in vacuo. Silica gel chromatography afforded the title compound.

NMR (CDCl₃): 7.70 (s, 1H); 7.62 (d, 2H, J=8.4 Hz); 7.55 (d, 2H, J=8.5 Hz); 7.44 (t, 2H, J=7.8 Hz); 7.34 (d, 1H, J=2.1 Hz); 7.26 (d, 1H, J=8.3); 7.19 (dd, 1H, J=8.3, 2.1 Hz); 6.9 (d, 1H, J=8.6 Hz); 4.16 (t; 2H; J=5.7); 3.63 (s, 3H); 3.17 (t, 2H, 7.3 Hz); 2.9 (t, 2H, J=7.3 Hz); 1.53 (s, 6H).

4. 2-methyl-2-(3-chloro-4-(3-(3-phenyl-7-propylbenzofuran-6-oxy) propyl)thio)phenyl propionic acid A solution of 2-methyl-2-(3-chloro-4-(3-(3-phenyl-7-propyl-6-benzofuranoxy)propyl)thio)phenyl propionic acid methyl ester (0.038 g; 0.070 mmol) in isopropanol (1.0 mL) was refluxed and treated with a solution of potassium hydroxide in water (1.0M; 0.212 mL; 0.212 mmol). After 3 hours the reaction mixture was partitioned between isopropyl acetate and 0.1N HCl. The organic layer was dried over magnesium sulfate, filtered and concentrated in vacuo affording the title compound.

NMR (CDCl₃): 7.70 (s, 1H); 7.61 (d, 2H, J=7.1 Hz); 7.54 (d, 1H, J=8.5 Hz); 7.44 (t, 2H, J=7.8 Hz), 7.40 (d, 1H, J=2.1); 6.89 (d, 1H, J=8.5 Hz); 4.15 (t, 2H, J=5.8 Hz); 3.17 (t, 2H, J=7.2 Hz); 2.89 (t, 2H, J=8.0 Hz); 1.22 (s, 6H).

EXAMPLE 26

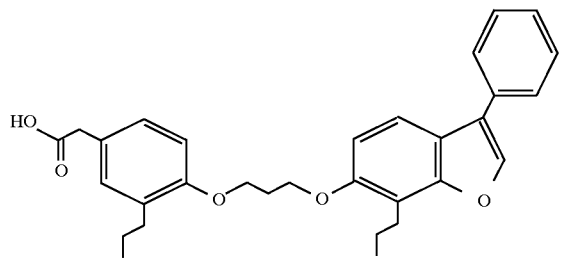

3-Propyl-4-(3-(3-phenyl-7-propylbenzofuran-6-yloxy) propyloxy)-phenylacetic acid Step A: Preparation of methyl 3-propyl-4-(3-(3-phenyl-7-propylbenzofuran-6-yloxy)propyloxy)-phenylacetate Using the method of Example 19, step E, using 3-phenyl-6-(3-bromopropyloxy)-7-propylbenzofuran as the starting material, the title compound was obtained.

1H NMR(400 MHz, CDCl₃): δ7.69 (s, 1H), 7.60 (d, 2H, J=8.4 Hz), 7.60 (d, 1H, J=8.5 Hz), 7.24 (t, 2H, J=8.0 Hz), 7.32 (m, 1H), 7.06 (m, 2H), 6.92 (d, 1H, J=8.5 Hz), 6.80 (d, 1H, J=8.2 Hz), 4.22 (t, 2H, J=6.1 Hz), 4.17 (t, 2H, J=6.0 Hz), 3.67 (s, 3H), 3.54 (s, 2H), 2.87 (t, 2H, J=6.2 Hz), 2.54 (t, 2H, J=6.0 Hz), 2.29 (quint, 2H, J=5.9 Hz), 1.68 (hex, 2H, J=7.3 Hz), 1.55 (hex, 2H, J=7.2 Hz), 0.93 (t, 3H, J=7.4 Hz), 0.89 (t, 3H, J=7.3 Hz)

Step B: Preparation of 3-propyl-4-(3-(3-phenyl-7-propylbenzofuran-6-yloxy)propyloxy)-phenylacetic acid Using the method of Example 19, step F, methyl 3-propyl-4-(3-(3-phenyl-7-propylbenzofuran-6-yloxy)propyloxy)-phenylacetate as the starting material, the title compound was obtained.

1H NMR(400 MHz, CDCl₃): δ7.69 (s, 1H), 7.60 (d, 2H, J=8.4 Hz), 7.60 (d, 1H, J=8.5 Hz), 7.24 (t, 2H, J=8.0 Hz), 7.32 (m, 1H), 7.06 (m, 2H), 6.92 (d, 1H, J=8.5 Hz), 6.80 (d, 1H, J=8.2 Hz), 4.22 (t, 2H, J=6.1 Hz), 4.17 (t, 2H, J=6.0 Hz), 3.54 (s, 2H), 2.87 (t, 2H, J=6.2 Hz), 2.54 (t, 2H, J=6.0 Hz), 2.29 (quint, 2H, J=5.9 Hz), 1.68 (hex, 2H, J=7.3 Hz), 1.55 (hex, 2H, J=7.2 Hz), 0.93 (t, 3H, J=7.4 Hz), 0.89 (t, 3H, J=7.3 Hz).

ESI: MS m/e=487 (M+1)

EXAMPLE 27

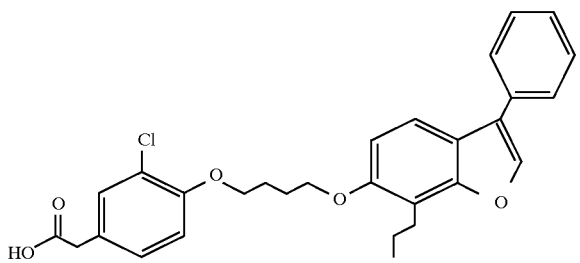

3-Chloro-4-(3-(3-phenyl-7-propylbenzofuran-6-yloxy)butyloxy)-phenylacetic acid

Step A: Preparation of methyl 3-chloro-4-(3-(3-phenyl-7-propylbenzofuran-6-yloxy)butyloxy)-phenylacetate Using the method of Example 19, step E, using methyl 3-chloro-4-(4-bromobutyloxy)-phenylacetate (Example 8, Step 2) and 3-phenyl-6-hydroxy-7-propylbenzofuran (Example 5, Step B) as the starting material, the title compound was obtained.

¹H NMR(400 MHz, CDCl₃): δ7.69 (s, 1H), 7.62 (dd, 2H, J=8.4, 1.4 Hz), 7.06 (d, 1H, J=8.5 Hz), 7.24 (t, 2H, J=7.5 Hz), 7.32 (m, 1H), 7.06 (m, 1H), 7.10 (dd, 1H, J=8.5, 2.2 Hz), 6.92 (d, 1H, J=8.6 Hz), 6.85 (d, 1H, J=8.4 Hz), 4.12 (m, 4H), 3.67 (s, 3H), 3.54 (s, 2H), 2.88 (t, 2H, J=7.5 Hz), 2.05 (m, 4H), 1.68 (hex, 2H, J=7.3 Hz), 0.96 (t, 3H, J=7.3 Hz)

Step B: Preparation of 3-chloro-4-(3-(3-phenyl-7-propylbenzofuran-6-yloxy)butyloxy)-phenylacetic acid Using the method of Example 19, step F, methyl 3-chloro-4-(3-(3-phenyl-7-propylbenzofuran-6-yloxy)butyloxy)-phenylacetate as the starting material, the title compound was obtained.

¹H NMR(400 MHz, CDCl₁): δ7.69 (s, 1H), 7.62 (dd, 2H, J=8.4, 1.4 Hz), 7.06 (d, 1H, J=8.5 Hz), 7.24 (t, 2H, J=7.5 Hz), 7.32 (m, 1H), 7.06 (m, 1H), 7.10 (dd, 1H, J=8.5, 2.2 Hz), 6.92 (d, 1H, J=8.6 Hz), 6.85 (d, 1H, J=8.4 Hz), 4.12 (m, 4H), 3.54 (s, 2H), 2.88 (t, 2H, J=7.5 Hz), 2.05 (m, 4H), 1.68 (hex, 2H, J=7.3 Hz), 0.96 (t, 3H, J=7.3 Hz)

ESI: MS m/e=493 (M+1)

EXAMPLE 28

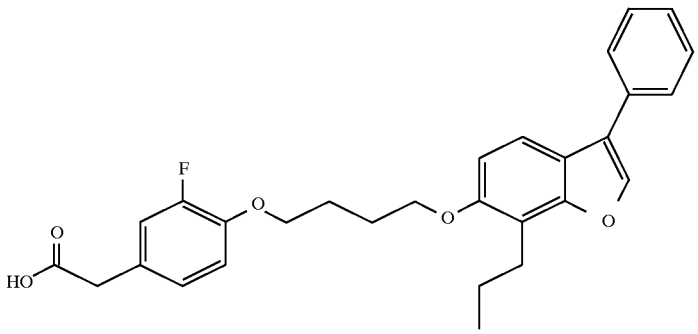

3-Floro-4-(3-(3-phenyl-7-propylbenzofuran-6-yloxy)butyloxy)-phenylacetic acid

Step A: Preparation of methyl 3-fluoro-4-(3-(3-phenyl-7-propylbenzofuran-6-yloxy)butyloxy)-phenylacetate Using the method of Example 27, step A, using methyl 3-floro-4-(4-bromobutyloxy)-phenylacetate and 3-phenyl-6-hydroxy-7-propylbenzofuran (Example 5, Step B) as the starting material, the title compound was obtained.

$^1$H NMR(400 MHz, CDCl$_1$): δ7.69 (s, 1H), 7.62 (dd, 2H, J=8.4, 1.4 Hz), 7.06 (d, 1H, J=8.5 Hz), 7.24 (t, 2H, J=7.5 Hz), 7.32 (m, 1H), 7.10 (dd, 1H, J=8.5, 2.2 Hz), 6.92 (m, 3H), 4.12 (m, 4H), 3.67 (s, 3H), 3.54 (s, 2H), 2.88 (t, 2H, J=7.5 Hz), 2.05 (m, 4H), 1.68 (hex, 2H, J=7.3 Hz), 0.96 (t, 3H, J=7.3 Hz)

Step B: Preparation of 3-fluoro-4-(3-(3-phenyl-7-propylbenzofuran-6-yloxy)butyloxy)-phenylacetic acid Using the method of Example 27, step B, using methyl 3-floro-4-(3-(3-phenyl-7-propylbenzofuran-6-yloxy)butyloxy)-phenylacetate as the starting material, the title compound was obtained.

$^1$H NMR(400 MHz, CDCl$_3$): δ7.69 (s, 1H), 7.62 (dd, 2H, J=8.4, 1.4 Hz), 7.06 (d, 1H, J=8.5 Hz), 7.24 (t, 2H, J=7.5 Hz), 7.32 (m, 1H), 7.10 (dd, 1H, J=8.5, 2.2 Hz), 6.92 (m, 3H), 4.12 (m, 4H), 3.54 (s, 2H), 2.88 (t, 2H, J=7.5 Hz), 2.05 (m, 4H), 1.68 (hex, 2H, J=7.3 Hz), 0.96 (t, 3H, J=7.3 Hz).

ESI: MS m/e=477 (M+1).

EXAMPLE 29

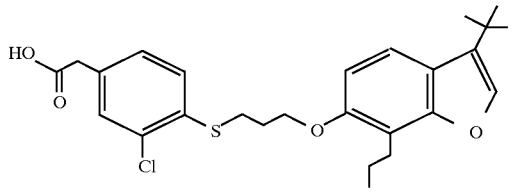

3-Chloro-4-(3-(3-tert-butyl-7-propylbenzofuran-6-yloxy)propylthio)-phenylacetic acid Step A: Preparation of 2-propyl-3-(2-tert-butyl-2-oxoethoxy)phenol Using the method of Example 5, Step A, using 1-bromopinacolone as the starting material, the title compound was obtained.

$^1$H NMR(300 MHz, CDCl$_3$): δ6.95 (t, 1H, J=8.2 Hz), 6.46 (dd, 1H, J=8.1, 1.0 Hz), 6.25 (d, 1H, J=8.2 Hz), 5.25–5.10 (s, 1H), 4.85 (s, 2H), 2.68 (t, 2H, J=7.7 Hz), 1.59 (hex, 2H, J=7.5 Hz), 1.25 (s, 9H), 0.96 (t, 3H, J=7.3 Hz).

Step B: Preparation of 3-tert-butyl-6-hydroxy-7-propylbenzofuran

Using the method of Example 5, Step B, using 2-propyl-3-(2-tert-butyl-2-oxoethoxy)phenol as the starting material, the title compound was obtained.

$^1$H NMR(400 MHz, CDCl$_3$): δ7.37 (d, 1H, J=8.4 Hz), 7.24 (s, 1H), 6.72 (d, 1H, J=8.3 Hz), 2.84 (t, 2H, J=7.6 Hz), 1.72 (hex, 2H, J=7.5 Hz), 1.39 (s, 9H), 1.00 (t, 3H, J=7.3 Hz).

Step C: Preparation of methyl 3-chloro-4-(3-(3-tert-butyl-7-propylbenzofuran-6-yloxy)propylthio)-phenylacetate Using the method of Example 27, step A, 3-tert-butyl-6-hydroxy-7-propylbenzofuran as the starting material, the title compound was obtained.

$^1$H NMR(400 MHz, CDCl$_3$): δ7.42 (d, 1H, J=8.6 Hz), 7.25 (m, 3H), 7.11 (dd, 1H, J=8.0, 1.9 Hz), 6.82 (d, 1H, J=8.7 Hz), 4.12 (t, 2H, J=5.7 Hz), 3.68 (s, 3H), 3.54 (s, 2H), 3.16 (t, 2H, J=7.2 Hz), 2.82 (t, 2H, J=7.5 Hz), 2.15 (quint, 2H, J=7.2 Hz), 1.66 (hex, 2H, J=7.3 Hz), 1.38 (s, (H), 0.93 (t, 3H, J=7.4 Hz).

Step D: Preparation of 3-chloro-4-(3-(3-tert-butyl-7-propylbenzofuran-6-yloxy)propylthio)-phenylacetic acid Using the method of Example 27, step A, methyl 3-chloro-4-(3-(3-tert-butyl-7-propylbenzofuran-6-yloxy)propylthio)-phenylacetate as the starting material, the title compound was obtained.

$^1$H NMR(400 MHz, CDCl$_3$): δ7.42 (d, 1H, J=8.6 Hz), 7.25 (m, 3H), 7.11 (dd, 1H, J=8.0, 1.9 Hz), 6.82 (d, 1H, J=8.7 Hz), 4.12 (t, 2H, J=5.7 Hz), 3.54 (s, 2H), 3.16 (t, 2H, J=7.2 Hz), 2.82 (t, 2H, J=7.5 Hz), 2.15 (quint, 2H, J=7.2 Hz), 1.66 (hex, 2H, J=7.3 Hz), 1.38 (s, (H), 0.93 (t, 3H, J=7.4 Hz).

CI: MS m/e=475 (M+1)

EXAMPLE 30

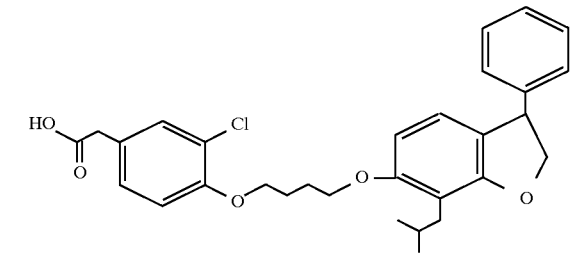

3-Chloro-4(3-(3-phenyl-7-isobutyl-(2H)benzofuran-6-yloxy)butyloxy)-phenyl acetic acid Scheme A: Preparation of methyl 3-chloro-4-(3-bromobutyloxy)-phenylacetate The titled compound was prepared as in Example 15, Step B.

Scheme B: Preparation of 6-isobutylenoxy-(2H)-benzofuran-3-one

The titled compound was prepared according to the method described in Example 11, Step B, using 6-hydroxy-(2H)-benzofuran-3-one and 3-bromo-2-methyl propene.

$^1$H NMR (400 MHz, CDCl$_3$, ppm): δ7.56(d,1H, J=8.6), 6.67(d, 1H, J=8.6), 6.55(s, 1H), 5.07(d, 2H, J=7.9), 4.62(s, 2H), 4.50(s, 2H), 1.83(s, 3H).

Scheme C: Preparation of 6-isobutylenoxy-3-phenyl-benzofuran

To a solution of 6-isobutylenoxy-(2H)-benzofuran-3-one (4.9 mmol) in tetrahydrofuran (25 ml), at 0° was added gradually phenyl magnesium bromide (1 molar solution in tetrahydrofuran) (24.48 mmol). Reaction was stirred at 24° overnight. Reaction was quenched with saturated NH$_4$Cl solution. Mixture was extracted with EtOAc. The organic layer was washed with water, brine, dried over sodium sulfate, filtered, concentrated in vacuo, and the crude residue was purified by flash chromatography on silica gel (10% ethyl acetate/hexane) to provide the title compound.

$^1$H NMR (400 MHz, CDCl$_3$, ppm): δ7.69–6.94(m, 8H,), 7.24(s, 1H), 5.12(s, 1H), 5.00(s, 1H), 4.49(s, 2H), 1.85(s, 3H).

Scheme D: Preparation of 6-hydroxy-7-isobutyl-(2H)3-phenyl-benzofuran

The titled compound was prepared according to the method described in Example 11, Step C, using 6-isobutylenoxy-2H,3-phenyl-benzofuran as starting material.

$^1$H NMR (400 MHz, CDCl$_3$, ppm): δ7.33–6.29(m, 5H), 6.68(d, 1H, J=8.0), 6.30(d, 1H, J=8.0), 4.85(t, 1H, J=7.7 Hz), 4.58(t, 1H, J=7.7 Hz 4.41–4.35 (m, 1H), 2.51 (dd, 3H, J=7.3–2.4 Hz), 2.05–1.93(m, 1H), 0.98 (d, 3H, J=3.4 Hz), 0.96 (d, 3H, J=3.4 Hz).

Step E: Methyl-3-Chloro-4(3-(3-phenyl-7-isobutyl(2H-benzofuran-6-yloxy)butyloxy)-phenyl acetate The titled compound was prepared according to the method described in Example 11, Step D, using methyl 3-chloro-4-(3-bromobutyloxy)-phenylacetate(Step A) and 6-hydroxy-7-isobutyl-(2H)-3-phenyl-benzofuran as starting material.

$^1$H NMR (400 MHz, CDCl$_3$, ppm): δ7.29–6.83(m, 8H), 6.74(d, 1H, J=8.20), 6.34 (d, 1H, J=8.20 Hz), 4.85(t, 1H, J=8.9 Hz), 4.58(t, 1H, J=7.7 Hz), 4.38–4.34 (m, 1H), 4.38–4.09 (m, 6H ), 3.67(s, 3H), 3.52(s, 2H), 2.51 (dd, 3H, J=7.3–2.4 Hz), 2.02–1.95(m, 3H), 0.91 (d, 3H, J=5.1 Hz), 0.89 (d, 3H, J=5.1 Hz).

Step F: 3-Chloro-4-(3-(3-phenyl-7-isobutyl-2H-benzofuran-6-yloxy)butyloxy)-phenyl acetic acid A mixture of Methyl-3-Chloro-4(3-(3-phenyl-7-isobutyl-(2H-benzofuran-6-yloxy)butyloxy)-phenyl acetate (328 mg, 0.58 mmoles), hydroxylamine hydrochloride (202 mg, 2.9 mmoles), anhydrous sodium acetate (238 mg, 2.9 mmoles) and ethanol (4 ml) was heated under reflux in a nitrogen atmosphere with magnetic stirring for 2 hr. The mixture was partitioned between ethyl acetate and water. The aqueous phase was extracted twice with ethyl acetate. The combined ethyl acetate phases were washed with water, 10% NaHCO$_3$ solution, and saturated NaCl solution, and dried (MgSO$_4$). Evaporation in vacuo and purification by chromatography (silica gel, 4:1 hexane-ethyl acetate) gave the title compound as a colorless solid.

$^1$H NMR (400 MHz, CDCl$_3$, ppm): δ7.35–6.83(m, 8H), 6.74(d, 1H, J=8.20), 6.34 (d, 1H, J=8.20 Hz), 4.85(t, 1H, J=8.9 Hz), 4.58(t, 1H, J=7.7 Hz), 4.38–4.34 (m, 1H), 4.18–3.95 (m, 6H ), 3.52(s, 2H), 2.51 (dd, 3H, J=7.3–2.4 Hz), 2.02–1.95(m, 3H), 0.91 (d, 3H, J=5.1 Hz), 0.89 (d, 3H, J=5.1 Hz).

ESI: MS: m/e=509(M+).

EXAMPLE 31

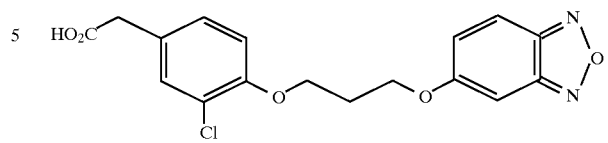

3-chloro-4-(3-(benzofurazanyl-5-oxy)-propyloxy) phenylacetic acid

STEP A: Preparation of Methyl 3-chloro-4-(3-bromopropyloxy) phenylacetate

A solution of 3-chloro-4-hydroxyphenylacetic acid methyl ester (25.545 grams) in 2-butanone (300 mL) was treated with 1,3-dibromopropane (48.79 mL) and potassium carbonate (50.859 grams). The mixture was refluxed for 4 hours. The reaction mixture was partitioned between iso-propyl acetate and pH 4 buffer. The organic was washed once with water, then dried over magnesium sulfate. The organic was filtered and evaporated to an oil which was chromatographed over silica gel with hexane/methylene chloride (2:1) to afford the title compound.

STEP B: Preparation of Methyl 3-chloro-4-(3-(benzofurazanyl-5-oxy)-propyloxy)phenylacetate Using the method in example 15, step C substituting methyl 3-chloro-4-(3-bromopropyloxy)phenylacetate and 5-hydroxybenzofurazan as the starting materials, the titled compound was obtained. This compound was taken forward without further purification.

STEP C: Preparation of 3-chloro-4-(3-(5-benzofurazanoloxy)-propyloxy)phenylacetic acid Using the method in example 2, substituting methyl 3-chloro-4-(3-(benzofurazanyl-5-oxy)-propyloxy) phenylacetate as the starting material, the titled compound was obtained.

NMR (CDCl$_3$) δ7.67 (d, 1H, J=8.78 Hz); 7.27 (s, 1H); 7.08 (m, 2H); 6.88 (d, 2H, J=8.42 Hz); 4.28 (t, 2H, J=6.15 Hz); 4.21 (t, 2H, J=5.86 Hz); 3.54 (s, 2H); 2.36 (m, 2H).

ESI: Mass spec: m/e=363 (M+1).

EXAMPLE 32

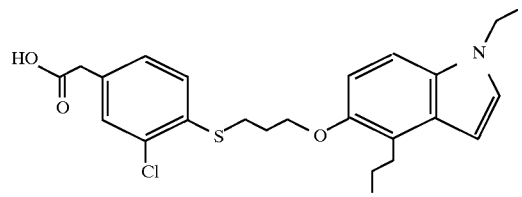

3-Chloro-4-(3-(4-propyl-N-ethyl-indolyl-5-oxy) propylthio)-phenylacetic acid

Step A: Preparation of 5-allyloxy-N-ethylindole

Using the method of Example 7, Step B, using ethyl bromide as the starting material, the title compound was obtained.

$^1$H NMR(300 MHz, CDCl$_3$): δ8.12 (s, 1H), 7.33 (s, 1H), 7.18 (dd, 1H, J=8.2, 1.4 Hz), 6.88(dd, 1H, J=8.3, 1.6 Hz), 6.46 (m, 1H), 6.11 (m, 1H), 5.49–5.27 (m,2H), 4.58 (m, 2H), 4.11 (quart, 2H, J=7.4 Hz), 1.46 (t, 3H, J=7.3 Hz).

Step B: Preparation of 4-allyl-5-hydroxy-N-ethylindole

Using the method of Example 7, Step C, using 5-allyloxy-N-ethylindole as the starting material, the title compound was obtained.

¹H NMR(300 MHz, CDCl₃): δ7.13 (d, 1H, J=8.8 Hz), 7.10 (s, 1H), 6.81(d, 1H, J=8.7 Hz), 6.42 (s, 1H), 6.15–6.05 (m, 1H), 5.30–5.10 (m,2H), 4.70 (broad s, 1H), 4.13 (quart, 2H, J=7.4 Hz), 3.67 (m,2H), 1.46 (t, 3H, J=7.3 Hz).

Step C: Preparation of 5-hydroxy-4-propyl-N-ethylindole

Using the method of Example 7, step D, using 4-allyl-5-hydroxy-N-ethylindole as the starting material, the title compound was obtained.

¹H NMR(300 MHz, CDCl₃): δ7.08 (m, 2H), 6.77 (d, 1H, J=8.7 Hz), 6.43(dd, 1H, J=3.1, 0.6 Hz), 4.45 (broad s, 1H), 4.13 (quart, 2H, J=7.3 Hz), 2.86 (t, 2H, J=7.7 Hz), 1.72 (hex, 2H, J=7.4 Hz), 1.46 (t, 3H, J=7.3 Hz), 1.03 (t, 3H, J=7.4 Hz).

Step D: Preparation of 5-(3-bromopropyl)oxy-4-propyl-N-ethylindole

Using the method of Example 7, step E, using 5-hydroxy-4-propyl-N-ethylindole as the starting material, the title compound was obtained.

¹H NMR(300 MHz, CDCl₃): δ7.18 (m, 2H), 6.90 (d, 1H, J=8.7 Hz), 6.43(m, 1H), 4.16 (m, 4H), 3.73 (t, 2H, J=7.4 Hz), 2.86 (t, 2H, J=7.3 Hz), 2.33 (quint, 2H, J=7.2 Hz), 1.72 (hex, 2H, J=7.4 Hz), 1.46 (t, 3H, J=7.3 Hz), 1.01 (t, 3H, J=7.4 Hz).

Step E: Preparation of methyl 3-chloro-4-(3-(4-propyl-N-ethyl-indolyl-5-oxy)propylthio)phenylacetate Using the method of Example 7, step F, using 5-(3-bromopropyl)oxy-4-propyl-N-ethylindole as the starting material, the title compound was obtained.

¹H NMR(300 MHz, CDCl₃): δ7.30 (m, 2H), 7.15 (m, 3H), 6.91 (d, 1H, J=8.8 Hz), 6.43(dd, 1H, J=3.1, 0.7 Hz), 4.15 (m, 4H), 3.70 (s, 3H), 3.56 (s, 2H), 3.20 (2H, J=7.2 Hz), 2.86 (t, 2H, J=7.6 Hz), 2.17 (quint, 2H, J=7.4 Hz), 1.72 (hex, 2H, J=7.4 Hz), 1.46 (t, 3H, J=7.3 Hz), 0.98 (t, 3H, J=7.4 Hz).

Step F: Preparation of 3-chloro-4-(3-(4-propyl-N-ethyl-indolyl-5-oxy)propylthio)phenylacetic acid Using the method of Example 7, step G, using methyl 3-chloro-4-(3-(4-propyl-N-ethyl-indolyl-5-oxy)propylthio)phenylacetate as the starting material, the title compound was obtained.

¹H NMR(300 MHz, CDCl₃): δ7.30 (m, 2H), 7.15 (m, 3H), 6.91 (d, 1H, J=8.8 Hz), 6.43(dd, 1H, J=3.1, 0.7 Hz), 4.15 (m, 4H), 3.56 (s, 2H), 3.20 (2H, J=7.2 Hz), 2.86 (t, 2H, J=7.6 Hz), 2.17 (quint, 2H, J=7.4 Hz), 1.72 (hex, 2H, J=7.4 Hz), 1.46 (t, 3H, J=7.3 Hz), 0.98 (t, 3H, J=7.4 Hz).

ESI: MS m/e=446 (M+1)

BIOLOGICAL ASSAYS

I. White Adipose Tissue in vitro Assay

The ability of compounds of the present invention to enhance the insulin activation of ¹⁴C-glucose incorporation into glycogen in white adipose tissue (WAT) was determined by the following assay.

This assay measures the efficacy of the instant compounds to enhance the insulin activation of ¹⁴C-glucose incorporation into glycogen in white adipose tissue (WAT) in a 5 hour completely in vitro system. All procedures are performed in medium 199 containing 1% bovine serum albumen, 5 mM HEPES, and antibiotic (100 units/ml penicillin, 100 µg/ml streptomycin sulfate, 0.25 µg/ml amphotericin B), hereafter called culture medium. Epididymol fat pads are minced with scissors into small fragments, approximately 1 mm in diameter. Minced WAT fragments (100 mg) are incubated in a total volume of 0.9 ml culture medium containing 1 mU/ml insulin and test compound in tissue culture incubator at 37° C. with 5% $CO_2$ with orbital shaking for 3 hours. ¹⁴C-labeled glucose is added and incubation continued for 2 hours. Tubes are centrifuged at low speed, infranatant is removed and 1M NaOH is added. Incubation of alkali-treated WAT for 10 minutes at 60° C. solubilizes tissue. Resulting tissue hydrolyzate is applied to Whatman filter paper strips which are then rinsed in 66% ethanol followed by 100% acetone which removes unincorporated ¹⁴C-glucose from bound ¹⁴C-glycogen. The dried paper is then incubated in solution of amyloglucosidase to cleave glycogen into glucose. Scintillation fluid is added and samples are counted for ¹⁴C activity. Test compounds that resulted in ¹⁴C activity substantially above incubations with insulin alone are considered active insulin-enhancing agents. Active compounds were titrated to determine the compound concentration which resulted in 50% of maximum enhancement of insulin activation and were termed $EC_{50}$ values. $EC_{50}$ values for the instant compounds were found to be 50 µM or less, preferably 5.0 to 0.0001 µM or less.

II. PPAR Receptor Binding and/or Transactivation Assays

Compounds of the instant invention which are useful for the above discussed treatments can be identified and/or characterized by employing the PPAR δ, and γ binding assays and/or PPAR δ, PPAR α and PPARγ transactivation assays. The assays are useful in predicting or quantitating in vivo effects having to do with the control or modulation of glucose, free fatty acid, triglyceride, insulin or cholesterol. To evaluate $IC_{50}$ or $EC_{50}$, values the compounds were titrated in the appropriate assay using different concentrations of the compound to be tested. To obtain the appropriate values (%Inhibition-$IC_{50}$, or % Activation-$EC_{50}$), the data resulting from the assays were then analyzed by determining the best fit of a 4 parameter function to the data using the Levenberg-Marquardt non-linear fitting algorithm in Kaleidagraph (Synergy Software, Reading, Pa.). The human nuclear receptor cDNA for PPARδ (hPPARδ) has been cloned from a human osteosarcoma cell cDNA library and is fully described in A. Schmidt et al., Molecular Endocrinology, 6:1634–1641 (1992), herein incorporated by reference in its entirety. See A. Elbrecht et al., Biochem. and Biophy. Res. Comm. 224:431–437 (1996) and T. Sher et al., Biochem. 32:5598–5604 (1993) for a description of the human nuclear receptor gene PPARγ and α.

The hPPARδ binding assay comprises the steps of:

(a) preparing multiple test samples by incubating separate aliquots of the receptor hPPARδ with a test compound in TEGM containing 5–10% COS-1 cell cytoplasmic lysate and 2.5 nM labeled ([³H₂]Compound D, 17 Ci/mmole) for a minimum of 12 hours, and preferably for about 16 hours, at 4° C., wherein the concentration of the test compound in each test sample is different, and preparing a control sample by incubating a further separate aliquot of the receptor hPPARδ under the same conditions but without the test compound; then (b) removing unbound ligand by adding dextran/gelatin-coated charcoal to each sample while maintaining the samples at 4° C. and allowing at least 10 minutes to pass, then (c) subjecting each of the test samples and the control sample from step (b) to centrifugation at 4° C. until the charcoal is pelleted; then (d) counting a portion of the supernatant fraction of each of the test samples and the control sample from step (c) in a liquid scintillation counter and analyzing the results to determine the $IC_{50}$ of the test compound.

In the hPPARδ binding assay, preferably at least four test samples of varying concentrations of a single test compound are prepared in order to determine the $IC_{50}$.

The hPPARδ transactivation assay comprises the steps of:

(a) seeding an hPPARδ/GR stable CHO-K1 cell line into alpha MEM containing 10% FCS, 10 mM HEPES, and 500 mg/ml G418 at 37° C. in an atmosphere of 10% $CO_2$ in air, (b) incubating the cells from step (a) for 16 to 48 hours, preferably about 20 hours, at 37° C. in an atmosphere of 10% $CO_2$ in air;

(c) washing the cells from step (b) with alpha MEM;

(d) preparing multiple test cell groups by incubating separate groups of the cells from step (c) with the test compound in alpha MEM containing 5% charcoal stripped FCS, 10 mM HEPES, and 500 mg/ml G418, for 24 to 48 hours, preferably about 24 hours, at 37° C. in an atmosphere of 10% $CO_2$ in air, wherein the concentration of the test compound in each test cell group is different, and preparing a control cell group by incubating a further separate group of the cells from step (c) under the same conditions but without the test compound; then (e) preparing cell lysates from each of the test cell groups and the control cell group of step (d) using an aqueous detergent lysis buffer, and (f) measuring the luciferase activity of the test cell groups and the control cell group of step (e) and analyzing the results to determine the $EC_{50}$ of the test compound.

In the hPPARδ transactivation assay, preferably at least four test cell groups of varying concentrations of a single test compound are prepared in order to determine the $EC_{50}$.

Particular terms and abbreviations used herein are defined as follows: gst is glutathione-S-transferase; EDTA is ethylenediamine-tetraacetic acid; HEPES is N-[2-hydroxyethyl]-piperazine-N'-[2-ethanesulfonic acid]; FCS is fetal calf serum; Lipofectamine is a 3:1 (w/w) liposome formulation of the polycationic lipid 2,3-dioleyloxy-N-[2 (spermine-carboxamido)ethyl]-N,N-dimethyl-1-propanaminium-trifluoroacetate and the neutral lipid dioleoyl phosphatidylethanolamine in water; G418 is geneticin; MEM is Minimum Essential Medium; Opti MEM 1 Reduced-Serum Medium is an aqueous composition containing HEPES buffer, 2400 mg/L sodium bicarbonate, hypoxanthine, thymidine, sodium pyruvate, L-glutamine, trace elements, growth factors, and phenol red reduced to 1.1 mg/L; Luciferase Assay Reagent (in re-constituted form) is an aqueous composition containing 20 mM tricine, 1.07 mM $(MgCO_3)_4Mg(OH)_2 \cdot 5H_2O$, 2.67 mM $MgSO_4$, 0.1 mM EDTA, 33.3 mM DTT, 270 $\mu$M coenzyme A, 470 $\mu$M luciferin, 530 $\mu$M ATP, having a final pH of 7.8.

AD-5075 has the following structure:

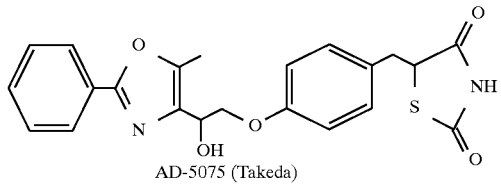

AD-5075 (Takeda)

Opti MEM 1 Reduced-Serum Medium, alpha MEM, G418, and Lipofectamine are commercially available from GibcoBRL Life Technologies, Gaithersburg, Md. Alpha MEM is an aqueous composition having the following components:

| Component: Inorganic Salts | mg/L |
|---|---|
| $CaCl_2$ (anhyd.) | 200.00 |
| $CaCl_2 \cdot 2H_2O$ | — |
| KCl | 400.00 |
| $MgSO_4$ (anhyd.) | 97.67 |
| $MgSO_4 \cdot 7H_2O$ | — |
| NaCl | 6800.00 |
| $NaHCO_3$ | 2200.00 |
| $NaH_2PO_4 \cdot H_2O$ | 140.00 |
| $NaH_2PO_4 \cdot 2H_2O$ | — |
| Other Components: | |
| D-Glucose | 1000.00 |
| Lipoic Acid | 0.20 |
| Phenol Red | 10.00 |
| Sodium Pyruvate | 110.00 |
| Amino Acids: | |
| L-Alanine | 25.00 |
| L-Arginine · HCl | 126.00 |
| L-Asparagine · $H_2O$ | 50.00 |
| L-Aspartic Acid | 30.00 |
| L-Cystine | — |
| L-Cystine · 2HCl | 31.00 |
| L-Cysteine HCl | — |
| L-Cysteine HCl · $H_2O$ | 100.00 |
| L-Glutamic Acid | 75.00 |
| L-Glutamine | 292.00 |
| L-Alanyl-L-Glutamine | — |
| Glycine | 50.00 |
| L-Histidine HCl · $H_2O$ | 42.00 |
| L-Isoleucine | 52.00 |
| L-Leucine | 52.00 |
| L-Lysine · HCl | 73.00 |
| L-Methionine | 15.00 |
| L-Phenylalanine | 32.00 |
| L-Proline | 40.00 |
| L-Serine | 25.00 |
| L-Threonine | 48.00 |
| L-Tryptophan | 10.00 |
| L-Tyrosine | — |
| L-Tyrosine (disodimn salt) | 52.00 |
| L-Valine | 46.00 |
| Vitamins: | |
| L-Ascorbic acid | 50.00 |
| Biotin | 0.10 |
| D-Ca Pantothenate | 1.00 |
| Choline Chloride | 1.00 |
| Folic acid | 1.00 |
| i-Inositol | 2.00 |
| Niacinamide | 1.00 |
| Pyridoxal HCl | 1.00 |
| Riboflavin | 0.10 |
| Thiamine HCl | 1.00 |
| Vitamin $B_{12}$ | 1.40 |
| Ribonucleosides | |
| Adenosine | 10.00 |
| Cytidine | 10.00 |
| Guanosine | 10.00 |
| Uridine | 10.00 |
| Deoxyribonucleosides | |
| 2' Deoxyadenosine | 10.00 |
| 2' Deoxycytidine HCl | 11.00 |
| 2' Deoxyguanosine | 10.00 |
| Thymidine | 10.00 |

The instant compounds, which are useful for treating the above discussed disease states, will preferably have $IC_{50}$ values at one, two or all of the PPAR (PPARγ, PPARδ or PPARα) receptor cites of equal to or less than 10 $\mu$M binding assay, and an $EC_{50}$ equal to or less than 10 $\mu$M in the transactivation assay. Preferably, an $IC_{50}$ of 100 nM in the binding assay, and an $EC_{50}$ equal to or less than 100 nM in the transactivation assay. More preferably, the instant compounds have an $IC_{50}$ equal to or less than 50 nM in the binding assay, and an $EC_{50}$ equal to or less than 50 nM in the transactivation assay. Most preferably, the instant compounds have an $IC_{50}$ equal to or less than 10 nM in the binding assay, and an $EC_{50}$ equal to or less than 10 nM in the transactivation assay.

PPAR Receptor Binding Assay

A. Preparation of Human PPARγ2 and δ

Human PPARγ2 and PPARδ, independently, were prepared as gst-fusion proteins in *E. coli*. The full length human cDNA for PPARγ2 and PPARδ were subcloned into the PGEX-2T and PGEX-KT, respectively, expression vector (Pharmacia). *E. coli* containing the plasmid were grown, induced, and then harvested by centrifugation. The resuspended pellet was broken in a French press and debris was removed by centrifugation at 12,000×g. Receptors were purified from the supernatant by affinity chromatography on glutathione sepharose. After application to the column, and 1 wash, receptor was eluted with glutathione. Glycerol was added to stabilize the receptor and aliquots were frozen at −80° C. for later use.

B. [$^3$H]AD-5075 and Example 11 Displacement Assay for PPARγ2 and PPARδ, respectively For each assay, an aliquot of receptor (1:1000–1:3000 dilution) was incubated in TEGM (10 mM Tris, pH 7.2, 1 mM EDTA, 10% glycerol, 7 μl/100 ml β-mercaptoethanol, 10 mM Na molybdate, 1 mM dithiothreitol, 5 μg/ml aprotinin, 2 μg/ml leupeptin, 2 μg/ml benzamide and 0.5 mM PMSF) containing 5–10% COS-1 cell cytoplasmic lysate and 10 nM labeled thiazolidinedione ([$^3$H$_2$]AD-5075, 21 Ci/mmole), ± test compound compound, [$^3$H$_2$]Example 11, 17 Ci/mmole), ± test compound, respectively. Assays were incubated for ~16 h at 4° C. in a final volume of 300 μl. Unbound ligand was removed by addition of 200 μl dextran/gelatin-coated charcoal, on ice, for ~10 minutes. After centrifugation at 3000 rpm for 10 min at 4° C., 200 μl of the supernatant fraction was counted in a liquid scintillation counter. In this assay the $K_D$ for AD-5075 and Example 11 is 1 nM, respectively.

PPAR Receptor Transactivation Assay

A. Activation of hPPARγ and hPPARδ Methods

1. Plasmids

The chimeric receptor expression constructs, pSG5-hPPARδ2/GR and pSG5-hPPARδ/GR, were prepared by inserting the DNA binding domain of the murine glucocorticoid receptor adjacent to the ligand binding domain of hPPARγ2 or hPPARδ. These vectors were kindly provided by Dr. Azriel Schmidt (MRL). The glucocorticoid receptor-responsive reporter vector, pMMTV/luc/neo, contains the murine mammary tumour virus (MMTV) promoter adjacent to the luciferase gene (luc) and the neomycin resistance gene (neo). It was constructed from pMMTV/luc which was provided by Dr. Azriel Schmidt (Merck Research Laboratories). Prior to transfection into CHO-K1 cells, pSG5-hPPARγ2/GR and pSG5-hPPARδ/GR were linearized with Xba I. pMMTV/luc/neo DNA was cut with Pvu I. Wild type receptor constructs, pSG5-hPPARγ2, pSG5-hPPARδ and pSG5-hPPARα were prepared by inserting the full-length hPPARγ2, hPPARδ and PPARα cDNAs adjacent to the SV40 promoter in pSG5. The PPAR-responsive reporter construct, pPPRE-luc, contained 3 copies of a generic PPRE placed adjacent to the thymidine kinase minimal promoter and the luciferase reporter gene. The transfection control vector, pCMV-lacZ, contains the galactosidase Z gene under the regulation of the cytomegalovirus promoter.

2. Production of stable cell lines

CHO-K1 cells were seeded overnight at 6×10$^5$ cells /60 mm dish in alpha Minimum Essential Medium (MEM) containing 10% fetal calf serum (FCS), 10 mM HEPES, 100 units/ml PenicillinG and 100 μg/ml Streptomycin sulfate at 37° C. in an atmosphere of 10% $CO_2$ in air. The cells were washed once with OptiMEM 1 Reduced-Serum Medium and then cotransfected with 4.5 μg of pSG5-hPPARγ2 /GR or pSG5-hPPARδ/GR expression vector and 0.5 μg of pMMTV/luc/neo in the presence of 100 μg Lipofectamine (GIBCO BRL) according to the instructions of the manufacturer. Transfection medium was removed 2 h later and replaced with growth medium. After being incubated for 3 days, cells were subcultured by diluting the cell suspension 1/1250 and 1/6250 and placing the cells in a 100 mm culture dish. Selection of the stable cell lines was initiated the next day by adding 500 μg/ml G418 to the medium. Cells were routinely fed with the selection media for 1 month at which time 120 colonies were picked and transferred to 24 well culture plates. Ten days later, confluent colonies were transferred to 6 well plates to maintain stocks and to 96 well plates to assay for luciferase activity. Positive clones were characterized and validated by titrating 4 known agonists on each clone. Two clones, g2B2P2D9 and d2A5P2G3, were selected for screening purposes.

B. hPPAR/GR transactivation screens in stably transfected CHO-K1 cells

The hPPARγ2/GR and hPPARδ/GR stable CHO-K1 cell lines were seeded at 1×10$^4$ cells/well in 96 well cell culture plates in alpha MEM containing 10% FCS, 10 mM HEPES, and 500 mg/ml G418 at 37° C. in an atmosphere of 10% $CO_2$ in air. After a 20 hour incubation, cells were washed once with alpha MEM and then incubated in an atmosphere of 10% $CO_2$ in air in alpha MEM containing 5% charcoal stripped FCS, 10 mM HEPES, and 500 mg/ml G418. The cells were incubated for 24 hours in the absence of test compound or in the presence of a range of concentrations of test compound. Cell lysates were prepared from washed cells using Reporter Lysis Buffer (Promega) according to the manufacturer's directions. Luciferase activity in cell extracts was determined using Luciferase Assay Reagent buffer (Promega) in a ML3000 luminometer (Dynatech Laboratories).

Transactivation Wild-Type Assay

A. Characterization of ligand activity on wild-type hPPARγ, hPPARδ and hPPARα.

COS-1 cells were seeded at 0.5×10$^5$ cells/dish into 24 well plates in Dulbecco's modified Eagle medium (high glucose) containing 10% charcoal stripped fetal calf serum, nonessential amino acids, 100 units/ml Penicillin G and 100 μg/ml Streptomycin sulfate at 37° C. in a humidified atmosphere of 10% $CO_2$. After 24 hours, transfections were performed with Lipofectamine (Gibco-BRL, Gaithersburg, Md.) according to the instructions of the manufacturer. In general, for transactivation experiments, transfection mixes contained 0.15 mg of hPPARγ2 hPPARα or hPPARδ expression vector, 0.15 mg of reporter vector pPPRE-luc and 0.001 mg of pCMV-lacZ as an internal control of transfection efficiency. Compounds demonstrating significant agonist activity in the above primary screen were further characterized by incubation with transfected cells for 48 h across a range of concentrations. Luciferase activity was determined as described above.

In a similar manner, hPPARγ1 cDNA can be used in place of hPPARγ2 cDNA in the methods described in Example 5 to make the wild type receptor construct, pSG5-hPPARγ1.

III. In Vivo Studies

Methods db/db Mice are obese, highly insulin resistant animals. The db locus has been shown to code for the leptin receptor. These animals are substantially hypertriglyceridemic and hyperglycemic.

Male db/db mice (10–11 week old C57Bl/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose) ± test compound at the indicated dose. Drug suspensions were prepared daily. Plasma glucose, Cholesterol and triglyceride concentrations were determined from blood obtained by tail bleeds at 3–5 day intervals during the study period. Glucose, cholesterol and triglyceride, determinations were performed on a Boehringer Mannheim Hitachi 911 automatic analyzer (Boehringer Mannheim, Indianapolis, Ind.) using heparinized plasma diluted 1:5, or 1:6 (v/v) with normal saline. Lean animals were age-matched heterozygous mice maintained in the same manner. The instant compounds were found to lower triglyceride and glucose levels at a dose of about 100 mg/kg, preferably a dose of about 10–50 mg/kg, when administered by oral gavage daily for a period of at least 5 days.

Lipoprotein analysis was performed on either serum, or EDTA treated plasma obtained by heart puncture from anesthetized animals at the end of the study. Apolipoprotein concentrations were determined by ELISA, and cholesterol particles were analyzed by FPLC, precipitation, or ultracentrifugation. Total liver RNA was prepared from tissue that had been frozen on liquid nitrogen at the time of euthanasia. Apolipoprotein mRNA was analyzed on Northern Blots using specific probes for mouse or rat proteins.

What is claimed is:

1. A compound having the formula I:

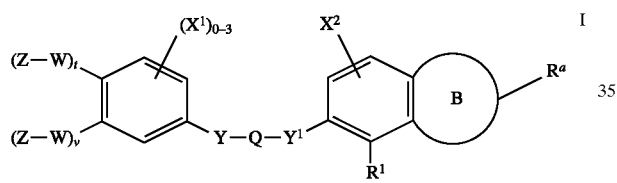

or a pharmaceutically acceptable salt thereof, wherein:

R is selected from the group consisting of H, $C_{1-6}$ alkyl, $C_{5-10}$ aryl, and $C_{5-10}$ heteroaryl, said alkyl, aryl and heteroaryl optionally substituted with 1 to 3 groups of $R^a$;

$R^1$ is selected from a group consisting of: H, $C_{1-15}$ alkyl, $C_{2-15}$ alkenyl, $C_{2-15}$ alkynyl and $C_{3-10}$ cycloalkyl, said alkyl, alkenyl, alkynyl, and cycloalkyl optionally substituted with 1 to 3 groups of $R^a$;

$R^3$ is selected from a group consisting of: H, $NHR^1$, NHacyl, $C_{1-15}$ alkyl, $C_{3-10}$ cycloalkyl, $C_{2-15}$ alkenyl, $C_{1-15}$ alkoxy, $CO_2$alkyl, OH, $C_{2-15}$ alkynyl, $C_{5-10}$ aryl, $C_{5-10}$ heteroaryl said alkyl, cycloalkyl, alkenyl, alkynyl, aryl and heteroaryl optionally substituted with 1 to 3 groups of $R^a$;

(Z—W—) is $Z-CR^6R^7-$, $Z-CH=CH-$, or

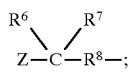

$R^8$ is selected from the group consisting of $CR^6R^7$, O, $NR^6$, and $S(O)_P$;

$R^6$ and $R^7$ are independently selected from the group consisting of H, $C_{1-6}$ alkyl;

B is selected from the group consisting of:
1) a 5 or 6 membered heterocycle containing 0 to 2 double bonds, and 1 heteroatom selected from the group consisting of O, S and N, heteroatom being substituted at any position on the five or six membered heterocycle, the heterocycle being optionally unsubstituted or substituted with 1 to 3 groups of $R^a$;
2) a 5 or 6 membered carbocycle containing 0 to 2 double bonds, the carbocycle optionally unsubstituted or substituted with 1 to 3 groups of $R^a$ at any position on the five or six membered carbocycle; and
3) a 5 or 6 membered heterocycle containing 0 to 2 double bonds, and 3 heteroatoms selected from the group consisting of O, N, and S, which are substituted at any position on the five or six membered heterocycle, the heterocycle being optionally unsubstituted or substituted with 1 to 3 groups of $R^a$;

$X^1$ and $X^2$ are independently selected from a group consisting of: H, OH, $C_{1-15}$ alkyl, $C_{2-15}$ alkenyl, $C_{2-15}$ alkynyl, halo, $OR^3$, $ORCF_3$, $C_{5-10}$ aryl, $C_{5-10}$ aralkyl, $C_{5-10}$ heteroaryl and $C_{1-10}$ acyl, said alkyl, alkenyl, alkynyl, aryl and heteroaryl optionally substituted with 1 to 3 groups of $R^a$;

$R^a$ represents a member selected from the group consisting of: halo, acyl, aryl, heteroaryl, $CF_3$, $OCF_3$, —O—, CN, $NO_2$, $R^3$, $OR^3$; $SR^3$, $=N(OR)$, $S(O)R^3$, $SO_2R^3$, $NR^3R^3$, $NR^3COR^3$, $NR^3CO_2R^3$, $NR^3CON(R^3)_2$, $NR^3SO_2R^3$, $COR^3$, $CO_2R^3$, $CON(R^3)_2$, $SO_2N(R^3)_2$, $OCON(R^3)_2$ said aryl and heteroaryl optionally substituted with 1 to 3 groups of halo or $C_{1-6}$ alkyl;

Y is selected from the group consisting of: $S(O)_p$, —$CH_2$—, —C(O)—, —C(O)NH—, —NR—, —O—, —$SO_2NH$, —$NHSO_2$;

$Y^1$ is selected from the group consisting of: O and C;

Z is selected from the group consisting of: $CO_2R^3$, $R^3CO_2R^3$, $CONHSO_2Me$, $CONH_2$ and 5-(1H-tetrazole);

t and v are independently 0 or 1 such that t+v=1

Q is a saturated or unsaturated straight chain hydrocarbon containing 2–4 carbon atoms and p is 0–2 with the proviso when Z is $CO_2R^3$ and B is a 5 membered heterocycle consisting of O, $R^3$ does not represent methyl.

2. A compound of claim 1 where $X^1$ & $X^2$ are independently H or halo.

3. A compound of claim 1 where Y is O.

4. A compound of claim 1 where Y is $S(O)_p$, wherein p is 0–2.

5. A compound of claim 1 where Y is —$CH_2$—.

6. A compound of claim 1 where Y is —CO—.

7. A compound of claim 1 where Y is —NH—.

8. A compound of claim 1 where Y is $NHSO_2$ or $SO_2NH$.

9. A compound of claim 1 where Y is C(O)NH.

10. A compound of claim 1 where W is —$CR^6R^7$— or

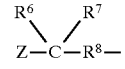

11. A compound of claim 1 where B is a 5 or 6 membered heterocycle containing 0 to 2 double bonds and 1 heteroatom selected from the group consisting O, S and N, the heteroatom is substituted at any position on the five or six membered heterocycle, the heterocycle being optionally unsubstituted or substituted with 1 to 3 groups of $R^a$.

12. A compound of claim 1 where B is a 5 or 6 membered carbocycle containing 0 to 2 double bonds, the carbocycle optionally unsubstituted or substituted with 1 to 3 groups of $R^a$ at any position on the five or six membered carbocycle.

13. A compound of claim 1 where B is a 5 or 6 membered heterocycle containing 0 to 2 double bonds, and 3 heteroatoms selected from the group consisting of O, S and N, which are substituted at any position on the five or six membered heterocycle, the heterocycle being optionally unsubstituted or substituted with 1 to 3 groups of $R^a$.

14. A compound of claim 1 wherein R is $C_{1-6}$ alkyl or $C_{5-10}$ aryl, said alkyl or aryl optionally substituted with 1 to 3 groups of $R^a$ $R^1$ is H or $C_{1-15}$ alkyl;

$X^1$ & $X^2$ are independently H, $C_{1-6}$ alkyl or halo;

Y is O, NH or S;

$Y^1$ is O;

(Z—W—) is Z—$CR^6R^7$— or

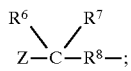

B is a 5 or 6 membered heterocycle containing 0 to 2 double bonds, and 1 heteroatom selected from the group consisting of O, S, and N, the heteroatom is substituted at any position on the five or six membered heterocycle, the heterocycle being optionally unsubstituted or substituted with 1 to 3 groups of $R^a$ and all other variables are described as above $R^a$ is a member selected from the group consisting of: halo, aryl, acyl, heteroaryl, $CF_3$, $OCF_3$, —O—, CN, $NO_2$, $R^3$, $OR^3$; $SR^3$, $S(O)R^3$, $SO_2R^3$, $NR^3COR^3$, $COR^3$, $CON(R^3)_2$, $SO_2N(R^3)_2$, said aryl and heteroaryl optionally substituted with 1 to 3 groups of halo or C1–6 alkyl; and Z is $CO_2R^3$, $CONHSO_2R$, $CONH_2$ or 5-(1H-tetrazole).

15. A compound of claim 1 selected from the group consisting of:
Methyl 3-chloro-4-(3-(4-ethyl-8-propyl-7 coumarinoxy) propylthio)phenyl-acetate;
3-Chloro-4-(3-(4-ethyl-8-propyl-7-coumarinoxy) propylthio) phenylacetic acid;
Methyl 3-chloro-4-(3-(3-ethyl-8-propyl-7-coumarinoxy) propylthio) phenyl-acetate;
3-Chloro-4-(3-(3-ethyl-8-propyl-7-coumarinoxy) propylthio) phenylacetic acid;
3-chloro-4-(3-(4-propyl-N-(4-chlorophenyl)-5-indoleoxy) propylthio)phenylacetic acid;
1-(3-chloro-4-(3-(3-phenyl-7-propylbenzofuran-6-oxy) propyl)thiophenyl-1-cyclopropane carboxylic acid;
3-chloro-4-(3-(3-phenyl-7-propylbenzofuran-6-yloxy) propylthio)-phenylacetic acid;
Methyl 3-chloro-4-(3-(3-phenyl-7-propylbenzofuran-6-yloxy)propylthio)-phenylacetate;
3-(4-(3-phenyl-7-propylbenzofuran-6-yl)oxy)butoxy) phenylacetic acid;
4-(3-(3-Phenyl-7-propylbenzofuran-6-yloxy)propylthio)-phenyl(2,2-dimethyl)acetic acid;
3-(3-(3-Phenyl-7-propylbenzothiophen-6-yloxy) propylamino)-phenyl(2,2-dimethyl)acetic acid;
4-(3-(3-Phenyl-7-propylbenzothiophen-6-yloxy) propylamino)-phenyl(2,2-dimethyl)acetic acid;
4-(3-(3-Phenyl-7-propylbenzofuran-6-yloxy)propyloxy)-phenylpropan-3-oic acid;
4-(4-(3-Phenyl-7-propylindol-6-yloxy)butylamino)-phenylpropan-3-oic acid;
3-(3-(3-Phenyl-7-propylbenzofuran-6-yloxy)propylthio)-phenoxyacetic acid;
4-(3-(3-Phenyl-7-propylbenzofuran-6-yloxy)propylthio)-phenoxyacetic acid;
4-(4-(1-Phenyl-4-propylindol-5-yloxy)butyloxy)-phenoxyacetic acid;
N-[4-(3-(3-Phenyl-7-propylbenzofuran-6-yloxy) propylamino)-phenyl]glycine;
N-[3-(4-(4-Phenyl-8-propylquinolin-7-yloxy)butyloxy)-phenyl]glycine;
N-[4-(4-(4-Phenyl-8-propylquinolin-7-yloxy)butyloxy)-phenyl]glycine;
4-(3-(3-Phenyl-7-propylbenzofuran-6-yloxy)propylamino)-phenylacetic acid;
4-(3-(4-Phenyl-8-propylquinazolin-7-yloxy)propylthio)-phenylacetic acid;
3-(3-(3-Phenyl-7-propylindan-6-yloxy)propylamino)-3-chlorophenylacetic acid;
4-(3-(3-Phenyl-7-propylindan-6-yloxy)propylamino)-3-chlorophenylacetic acid;
4-(3-(2-Phenyl-5-propylbenzofuran-6-yloxy)propylamino)-phenylacetic acid;
3-(3-(2-Phenyl-5-propylbenzofuran-6-yloxy)propylamino)-3-chlorophenylacetic acid;
4-(3-(2-Phenyl-5-propylindol-6-yloxy)propylamino)-3-chlorophenylacetic acid;
3-(3-(2-Phenyl-5-propylbenzothiophen-6-yloxy) propylamino)-3-chlorophenylacetic acid;
4-(3-(3-Phenyl-7-propylbenzofuran-6-yloxy)propylamino)-3-chlorophenylacetic acid;
4-(4-(3-Phenyl-7-prop-2-enylbenzofuran-6-yloxy)butyloxy)-3-chlorophenylacetic acid;
4-(3-(3-Phenyl-7-propylbenzofuran-6-yloxy)propylamino)-phenoxyacetic acid;
3-(3-(3-Phenyl-7-butylbenzofuran-6-yloxy)propylthio)-phenylpropan-3-oic acid;
4-(3-(3-Phenyl-7-butylbenzofuran-6-yloxy)propylthio)-phenylpropan-3-oic acid;
4-(3-(3-Phenyl-7-propylbenzofuran-6-yloxy)propyloxy)-2-phenyl-2,2-dimethylacetic acid;
4-(4-(3-Phenyl-7-(cyclopropylmethyl)benzofuran-6-yloxy) butylamino)-phenoxy-2,2-dimethylacetic acid;
3-(3-(3-Neopentyl-7-propylbenzofuran-6-yloxy)propylthio) -3-methylphenylacetic acid;
4-(3-(3-(2-Phenyl-2,2-dimethyl)-7-propylbenzofuran-6-yloxy)propyloxy)-3-butylphenylacetic acid;
4-(3-(3-Chloro-7-propylbenzofuran-6-yloxy)propylamino)-2-propylphenylacetic acid;
3-(3-(3-Chloro-7-propylbenzofuran-6-yloxy)propylamino)-2-propylphenylacetic acid;
4-(4-(3-Butoxy-7-propylbenzofuran-6-yloxy)butylthio)-2-fluorophenylacetic acid;
4-(3-(3-Phenyl-7-propylbenzofuran-6-yloxy)propylamino)-phenoxyacetic acid;
3-(3-(3-(3-Butylphenyl)-7-butylbenzofuran-6-yloxy) propylthio)-phenylpropan-3-oic acid;
4-(3-(3-(2-Tolyl)-7-butylbenzofuran-6-yloxy)propylthio)-phenylpropan-3-oic acid;
4-(3-(3-(4-Fluorophenyl)-7-propylbenzofuran-6-yloxy) propyloxy)-2-phenyl-2,2-dimethylacetic acid;
4-(3-(3-Phenyl-7-propylbenzofuran-6-yloxy)propyloxy)-phenoxy-2-spiro-cyclopropylacetic acid;
3-(3-(3-Phenyl-7-propylbenzofuran-6-yloxy)propyloxy)-phenoxy-2-spiro-cyclopropylacetic acid;
5-(4-(3-(3-Phenyl-7-propylbenzothiophen-6-yloxy) propylamino)phenyl-2-(2,2-dimethyl)-ethyl)-tetrazole;
5-(4-(3-(3-Phenyl-7-propylbenzofuran-6-yloxy)propyloxy) phenyl-3-propyl)-tetrazole;
5-(4-(4-(3-Phenyl-7-propylindol-6-yloxy)butylamino) phenyl-3-propyl)-tetrazole;
5-(3-(3-(3-Phenyl-7-propylbenzofuran-6-yloxy)propylthio) phenoxy-2-ethyl)-tetrazole; and 5-(4-(3-(3-Phenyl-7-propylbenzofuran-6-yloxy)propylthio) phenoxy-2-ethyl)-tetrazole.

16. A compound of claim 13 selected from the group consisting of:
Methyl 3-chloro-4-(3-(4-ethyl-8-propyl-7 coumarinoxy) propylthio)phenyl-acetate;
3-Chloro-4-(3-(4-ethyl-8-propyl-7-coumarinoxy) propylthio) phenylacetic acid;
Methyl 3-chloro-4-(3-(3-ethyl-8-propyl-7-coumarinoxy) propylthio) phenyl-acetate;
3-Chloro-4-(3-(3-ethyl-8-propyl-7-coumarinoxy) propylthio) phenylacetic acid;
3-chloro-4-(3-(4-propyl-N-(4-chlorophenyl)-5-indoleoxy) propylthio)phenylacetic acid;
1-(3-chloro-4-(3-(3-phenyl-7-propylbenzofuran-6-oxy) propyl)thiophenyl-1-cyclopropane carboxylic acid;
3-chloro-4-(3-(3-phenyl-7-propylbenzofuran-6-yloxy) propylthio)-phenylacetic acid;
Methyl 3-chloro-4-(3-(3-phenyl-7-propylbenzofuran-6-yloxy)propylthio)-phenylacetate;
4-(3-(3-Phenyl-7-propylbenzofuran-6-yloxy)propyloxy)-phenylacetic acid;
4-(3-(3-Phenyl-7-propylbenzothiophen-6-yloxy)propyloxy)-phenylacetic acid;
3-(4-(3-Phenyl-7-propylbenzofuran-6-yloxy)butyloxy)-phenylacetic acid;
3-(4-(3-Phenyl-7-propylindol-6-yloxy)butyloxy)-phenylacetic acid;
4-(3-(3-Phenyl-7-propylbenzofuran-6-yloxy)propyloxy)-phenoxyacetic acid;
4-(3-(3-Phenyl-7-propylbenzothiophen-6-yloxy)propyloxy)-phenoxyacetic acid;
4-(3-(3-Phenyl-7-propylbenzofuran-6-yloxy)propylthio)-3-propylphenylacetic acid;
4-(4-(3-Phenyl-7-propylindol-6-yloxy)butylthio)-3-chlorophenylacetic acid;
4-(4-(1-Phenyl-4-propylindol-5-yloxy)butylthio)-3-chlorophenylacetic acid;
4-(3-(3-Phenyl-7-propylbenzofuran-6-yloxy)propylsulfono)-3-propylphenylacetic acid;
4-(3-(3-Phenyl-7-propylbenzothiophen-6-yloxy) propylsulfono)-3-chlorophenylacetic acid;
4-(4-(3-Phenyl-7-propylbenzofuran-6-yloxy)butylthio)-3-propylbenzyl-tetrazole;
4-(4-(3-Phenyl-7-propylindol-6-yloxy)butylthio)-3-chlorobenzyl-tetrazole;
4-(4-(1-Phenyl-4-propylindol-5-yloxy)butylthio)-3-chlorobenzyl-tetrazole;
4-(3-(3-Phenyl-7-propylbenzofuran-6-yloxy)propylamino)-phenylacetic acid;
4-(3-(3-Phenyl-7-propylbenzothiophen-6-yloxy) propylamino)-phenylacetic acid;
3-(4-(4-(3-Phenyl-7-propylbenzofuran-6-yloxy)butyloxy)-phenylacetic acid;
3-(4-(4-(3-Phenyl-7-propylindol-6-yloxy)butyloxy)-phenylacetic acid;
3-Chloro-4-((1-propyl-2-dibenzoxyfuran)-propylthio)-phenylacetic acid;
3-chloro-4-(4-(4-trifluoromethyl-8-propyl-coumarinolyl-7-oxy)butyloxy)phenylacetic acid;
3-Propyl-4-(3-(4-tert-butylmethyl-8-propyl-coumarinolyl-7-oxy)-propylthio)phenylacetic acid; and
2-methyl-2-(3-chloro-4-(3-(3phenyl-7-propylbenzofuran-6-oxy)propyl)thio)phenyl propionic acid.

17. A method for the treatment or prevention of diabetes which comprises administering to a diabetic patient a pharmaceutically effective amount of a compound of formula I

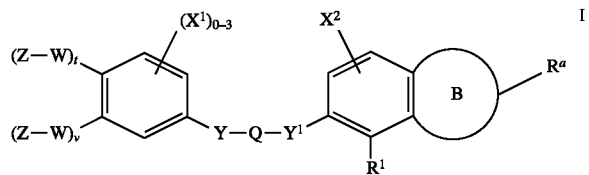

or a pharmaceutically acceptable salt thereof, wherein:
R is selected from the group consisting of H, $C_{1-6}$ alkyl, $C_{5-10}$ aryl, and $C_{5-10}$ heteroaryl, said alkyl, aryl and heteroaryl optionally substituted with 1 to 3 groups of $R^a$;
$R^1$ is selected from a group consisting of: H, $C_{1-15}$ alkyl, $C_{2-15}$ alkenyl, $C_{2-15}$ alkynyl and $C_{3-10}$ cycloalkyl, said alkyl, alkenyl, alkynyl, and cycloalkyl optionally substituted with 1 to 3 groups of $R^a$;
$R^3$ is selected from a group consisting of: H, $NHR^1$, NHacyl, $C_{1-15}$ alkyl, $C_{3-10}$ cycloalkyl, $C_{2-15}$ alkenyl, $C_{1-15}$ alkoxy, $CO_2$alkyl, OH, $C_{2-15}$ alkynyl, $C_{5-10}$ aryl, $C_{5-10}$ heteroaryl said alkyl, cycloalkyl, alkenyl, alkynyl, aryl and heteroaryl optionally substituted with 1 to 3 groups of $R^a$;
(Z—W—) is Z—$CR^6R^7$—, Z—CH=CH—, or

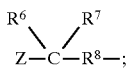

$R^8$ is selected from the group consisting of $CR^6R^7$, O, $NR^6$, and $S(O)_P$;
$R^6$ and $R^7$ are independently selected from the group consisting of H, $C_{1-6}$ alkyl;
B is selected from the group consisting of:
1) a 5 or 6 membered heterocycle containing 0 to 2 double bonds, and 1 heteroatom selected from the group consisting of O, S and N, heteroatom being substituted at any position on the five or six membered heterocycle, the heterocycle being optionally unsubstituted or substituted with 1 to 3 groups of $R^a$;
2) a 5 or 6 membered carbocycle containing 0 to 2 double bonds, the carbocycle optionally unsubstituted or substituted with 1 to 3 groups of $R^a$ at any position on the five or six membered carbocycle; and
3) a 5 or 6 membered heterocycle containing 0 to 2 double bonds, and 3 heteroatoms selected from the group consisting of O, N, and S, which are substituted at any position on the five or six membered heterocycle, the heterocycle being optionally unsubstituted or substituted with 1 to 3 groups of $R^a$;
$X^1$ and $X^2$ are independently selected from a group consisting of: H, OH, $C_{1-15}$ alkyl, $C_{2-15}$ alkenyl, $C_{2-15}$ alkynyl, halo, $OR^3$, $ORCF_3$, $C_{5-10}$ aryl, $C_{5-10}$ aralkyl, $C_{5-10}$ heteroaryl and $C_{1-10}$ acyl, said alkyl, alkenyl, alkynyl, aryl and heteroaryl optionally substituted with 1 to 3 groups of $R^a$;
$R^a$ represents a member selected from the group consisting of: halo, acyl, aryl, heteroaryl, $CF_3$, $OCF_3$, —O—, CN, $NO_2$, $R^3$, $OR^3$, $SR^3$, =N(OR), $S(O)R^3$, $SO_2R^3$, $NR^3R^3$, $NR^3COR^3$, $NR^3CO_2R^3$, $NR^3CON(R^3)_2$, $NR^3SO_2R^3$, $COR^3$, $CO_2R^3$, $CON(R^3)_2$, $SO_2N(R^3)_2$, $OCON(R^3)_2$ said aryl and heteroaryl optionally substituted with 1 to 3 groups of halo or C1–6 alkyl;
Y is selected from the group consisting of: $S(O)_p$, —$CH_2$—, —C(O)—, —C(O)NH—, —NR—, —O—, —$SO_2NH$—, —$NHSO_2$;

$Y^1$ is selected from the group consisting of: O and C;

Z is selected from the group consisting of: $CO_2R^3$, $R^3CO_2R^3$, $CONHSO_2Me$, $CONH_2$ and 5-(1H-tetrazole);

t and v are independently 0 or 1 such that t+v=1

Q is a saturated or unsaturated straight chain hydrocarbon containing 2–4 carbon atoms and p is 0–2.

18. A method for lowering triglyceride levels which comprises administering to a patient needing lower triglyceride levels a pharmaceutically effective amount of a compound of formula I

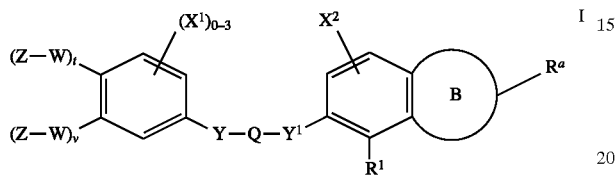

or a pharmaceutically acceptable salt thereof, wherein:

R is selected from the group consisting of H, $C_{1-6}$ alkyl, $C_{5-10}$ aryl, and $C_{5-10}$ heteroaryl, said alkyl, aryl and heteroaryl optionally substituted with 1 to 3 groups of $R^a$;

$R^1$ is selected from a group consisting of: H, $C_{1-15}$ alkyl, $C_{2-15}$ alkenyl, $C_{2-15}$ alkynyl and $C_{3-10}$ cycloalkyl, said alkyl, alkenyl, alkynyl, and cycloalkyl optionally substituted with 1 to 3 groups of $R^a$;

$R^3$ is selected from a group consisting of: H, $NHR^1$, NHacyl, $C_{1-15}$ alkyl, $C_{3-10}$ cycloalkyl, $C_{2-15}$ alkenyl, $C_{1-15}$ alkoxy, $CO_2$alkyl, OH, $C_{2-15}$ alkynyl, $C_{5-10}$ aryl, $C_{5-10}$ heteroaryl said alkyl, cycloalkyl, alkenyl, alkynyl, aryl and heteroaryl optionally substituted with 1 to 3 groups of $R^a$;

(Z—W—) is Z—$CR^6R^7$—, Z—CH=CH—, or

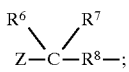

$R^8$ is selected from the group consisting of $CR^6R^7$, O, $NR^6$, and $S(O)_P$;

$R^6$ and $R^7$ are independently selected from the group consisting of H, $C_{1-6}$ alkyl;

B is selected from the group consisting of:
1) a 5 or 6 membered heterocycle containing 0 to 2 double bonds, and 1 heteroatom selected from the group consisting of O, S and N, heteroatom being substituted at any position on the five or six membered heterocycle, the heterocycle being optionally unsubstituted or substituted with 1 to 3 groups of $R^a$;
2) a 5 or 6 membered carbocycle containing 0 to 2 double bonds, the carbocycle optionally unsubstituted or substituted with 1 to 3 groups of $R^a$ at any position on the five or six membered carbocycle; and
3) a 5 or 6 membered heterocycle containing 0 to 2 double bonds, and 3 heteroatoms selected from the group consisting of O, N, and S, which are substituted at any position on the five or six membered heterocycle, the heterocycle being optionally unsubstituted or substituted with 1 to 3 groups of $R^a$;

$X^1$ and $X^2$ are independently selected from a group consisting of: H, OH, $C_{1-5}$ alkyl, $C_{2-15}$ alkenyl, $C_{2-15}$ alkynyl, halo, $OR^3$, $ORCF_3$, $C_{5-10}$ aryl, $C_{5-10}$ aralkyl, $C_{5-10}$ heteroaryl and $C_{1-10}$ acyl, said alkyl, alkenyl, alkynyl, aryl and heteroaryl optionally substituted with 1 to 3 groups of $R^a$;

$R^a$ represents a member selected from the group consisting of: halo, acyl, aryl, heteroaryl, $CF_3$, $OCF_3$, —O—, CN, $NO_2$, $R^3$, $OR^3$; $SR^3$, =N(OR), $S(O)R^3$, $SO_2R^3$, $NR^3R^3$, $NR^3COR^3$, $NR^3CO_2R^3$, $NR^3CON(R^3)_2$, $NR^3SO_2R^3$, $COR^3$, $CO_2R^3$, $CON(R^3)_2$, $SO_2N(R^3)_2$, $OCON(R^3)_2$ said aryl and heteroaryl optionally substituted with 1 to 3 groups of halo or C1–6 alkyl;

Y is selected from the group consisting of: $S(O)_p$, —$CH_2$—, —C(O)—, —C(O)NH—, —NR—, —O—, —$SO_2NH$, —$NHSO_2$;

$Y^1$ is selected from the group consisting of: O and C;

Z is selected from the group consisting of: $CO_2R^3$, $R^3CO_2R^3$, $CONHSO_2Me$, $CONH_2$ and 5-(1H-tetrazole);

t and v are independently 0 or 1 such that t+v=1

Q is a saturated or unsaturated straight chain hydrocarbon containing 2–4 carbon atoms and p is 0–2.

19. A method for treating obesity which comprises administering to a patient in need thereof a pharmaceutically effective amount of a compound of formula I

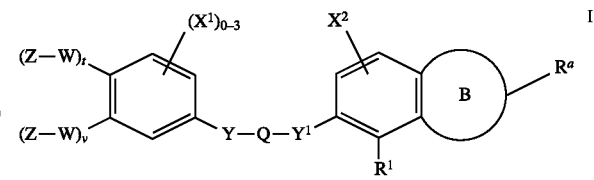

or a pharmaceutically acceptable salt thereof, wherein:

R is selected from the group consisting of H, $C_{1-6}$ alkyl, $C_{5-10}$ aryl, and $C_{5-10}$ heteroaryl, said alkyl, aryl and heteroaryl optionally substituted with 1 to 3 groups of $R^a$;

$R^1$ is selected from a group consisting of: H, $C_{1-15}$ alkyl, $C_{2-15}$ alkenyl, $C_{2-15}$ alkynyl and $C_{3-10}$ cycloalkyl, said alkyl, alkenyl, alkynyl, and cycloalkyl optionally substituted with 1 to 3 groups of $R^a$;

$R^3$ is selected from a group consisting of: H, $NHR^1$, NHacyl, $C_{1-15}$ alkyl, $C_{3-10}$ cycloalkyl, $C_{2-15}$ alkenyl, $C_{1-15}$ alkoxy, $CO_2$alkyl, OH, $C_{2-15}$ alkynyl, $C_{5-10}$ aryl, $C_{5-10}$ heteroaryl said alkyl, cycloalkyl, alkenyl, alkynyl, aryl and heteroaryl optionally substituted with 1 to 3 groups of $R^a$;

(Z—W—) is Z—$CR^6R^7$—, Z—CH=CH—, or

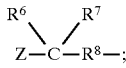

$R^8$ is selected from the group consisting of $CR^6R^7$, O, $NR^6$, and $S(O)_P$;

$R^6$ and $R^7$ are independently selected from the group consisting of H, $C_{1-6}$ alkyl;

B is selected from the group consisting of:
1) a 5 or 6 membered heterocycle containing 0 to 2 double bonds, and 1 heteroatom selected from the group consisting of O, S and N, heteroatom being substituted at any position on the five or six membered heterocycle, the heterocycle being optionally unsubstituted or substituted with 1 to 3 groups of $R^a$;
2) a 5 or 6 membered carbocycle containing 0 to 2 double bonds, the carbocycle optionally unsubstituted or substituted with 1 to 3 groups of $R^a$ at any position on the five or six membered carbocycle; and 3) a 5 or 6 membered heterocycle containing 0 to 2 double bonds, and 3 heteroatoms selected from the group consisting of O, N, and S, which are substituted at any position on the five or six membered heterocycle, the heterocycle being optionally unsubstituted or substituted with 1 to 3 groups of $R^a$;

$X^1$ and $X^2$ are independently selected from a group consisting of: H, OH, $C_{1-15}$ alkyl, $C_{2-15}$ alkenyl, $C_{2-15}$ alkynyl, halo, $OR^3$, $ORCF_3$, $C_{5-10}$ aryl, $C_{5-10}$ aralkyl, $C_{5-10}$ heteroaryl and $C_{1-10}$ acyl, said alkyl, alkenyl, alkynyl, aryl and heteroaryl optionally substituted with 1 to 3 groups of $R^a$;

$R^a$ represents a member selected from the group consisting of: halo, acyl, aryl, heteroaryl, $CF_3$, $OCF_3$, —O—, CN, $NO_2$, $R^3$, $OR^3$; $SR^3$, $=N(OR)$, $S(O)R^3$, $SO_2R^3$, $NR^3R^3$, $NR^3COR^3$, $NR^3CO_2R^3$, $NR^3CON(R^3)_2$, $NR^3SO_2R^3$, $COR^3$, $CO_2R^3$, $CON(R^3)_2$, $SO_2N(R^3)_2$, $OCON(R^3)_2$ said aryl and heteroaryl optionally substituted with 1 to 3 groups of halo or $C_{1-6}$ alkyl;

Y is selected from the group consisting of: $S(O)_p$, —$CH_2$—, —C(O)—, —C(O)NH—, —NR—, —O—, —$SO_2NH$, —$NHSO_2$;

$Y^1$ is selected from the group consisting of: O and C;

Z is selected from the group consisting of: $CO_2R^3$, $R^3CO_2R^3$, $CONHSO_2Me$, $CONH_2$ and 5-(1H-tetrazole);

t and v are independently 0 or 1 such that t+v=1

Q is a saturated or unsaturated straight chain hydrocarbon containing 2–4 carbon atoms and p is 0–2.

20. A method for halting, preventing or reducing the risk of developing atherosclerosis and related disease events in a patient in need of such treatment, comprising the administration of a pharmaceutically effective amount of a compound of formula I

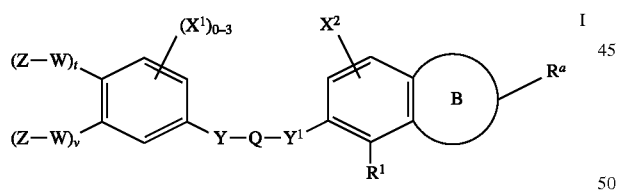

or a pharmaceutically acceptable salt thereof, wherein:

R is selected from the group consisting of H, $C_{1-6}$ alkyl, $C_{5-10}$ aryl, and $C_{5-10}$ heteroaryl, said alkyl, aryl and heteroaryl optionally substituted with 1 to 3 groups of $R^a$;

$R^1$ is selected from a group consisting of: H, $C_{1-15}$ alkyl, $C_{2-15}$ alkenyl, $C_{2-15}$ alkynyl and $C_{3-10}$ cycloalkyl, said alkyl, alkenyl, alkynyl, and cycloalkyl optionally substituted with 1 to 3 groups of $R^a$;

$R^3$ is selected from a group consisting of: H, $NHR^1$, NHacyl, $C_{1-15}$ alkyl, $C_{3-10}$ cycloalkyl, $C_{2-15}$ alkenyl, $C_{1-15}$ alkoxy, $CO_2$alkyl, OH, $C_{2-15}$ alkynyl, $C_{5-10}$ aryl, $C_{5-10}$ heteroaryl said alkyl, cycloalkyl, alkenyl, alkynyl, aryl and heteroaryl optionally substituted with 1 to 3 groups of $R^a$;

(Z—W—) is Z—$CR^6R^7$—, Z—CH=CH—, or

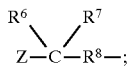

$R^8$ is selected from the group consisting of $CR^6R^7$, O, $NR^6$, and $S(O)_P$;

$R^6$ and $R^7$ are independently selected from the group consisting of H, $C_{1-6}$ alkyl;

B is selected from the group consisting of:
1) a 5 or 6 membered heterocycle containing 0 to 2 double bonds, and 1 heteroatom selected from the group consisting of O, S and N, heteroatom being substituted at any position on the five or six membered heterocycle, the heterocycle being optionally unsubstituted or substituted with 1 to 3 groups of $R^a$;
2) a 5 or 6 membered carbocycle containing 0 to 2 double bonds, the carbocycle optionally unsubstituted or substituted with 1 to 3 groups of $R^a$ at any position on the five or six membered carbocycle; and
3) a 5 or 6 membered heterocycle containing 0 to 2 double bonds, and 3 heteroatoms selected from the group consisting of O, N, and S, which are substituted at any position on the five or six membered heterocycle, the heterocycle being optionally unsubstituted or substituted with 1 to 3 groups of $R^a$;

$X^1$ and $X^2$ are independently selected from a group consisting of: H, OH, $C_{1-15}$ alkyl, $C_{2-15}$ alkenyl, $C_{2-15}$ alkynyl, halo, $OR^3$, $ORCF_3$, $C_{5-10}$ aryl, $C_{5-10}$ aralkyl, $C_{5-10}$ heteroaryl and $C_{1-10}$ acyl, said alkyl, alkenyl, alkynyl, aryl and heteroaryl optionally substituted with 1 to 3 groups of $R^a$;

$R^a$ represents a member selected from the group consisting of: halo, acyl, aryl, heteroaryl, $CF_3$, $OCF_3$, —O—, CN, $NO_2$, $R^3$, $OR^3$; $SR^3$, $=N(OR)$, $S(O)R^3$, $SO_2R^3$, $NR^3R^3$, $NR^3COR^3$, $NR^3CO_2R^3$, $NR^3CON(R^3)_2$, $NR^3SO_2R^3$, $COR^3$, $CO_2R^3$, $CON(R^3)_2$, $SO_2N(R^3)_2$, $OCON(R^3)_2$ said aryl and heteroaryl optionally substituted with 1 to 3 groups of halo or C1–6 alkyl;

Y is selected from the group consisting of: $S(O)_p$, —$CH_2$—, —C(O)—, —C(O)NH—, —NR—, —O—, —$SO_2NH$, —$NHSO_2$;

$Y^1$ is selected from the group consisting of: O and C;

Z is selected from the group consisting of: $CO_2R^3$, $R^3CO_2R^3$, $CONHSO_2Me$, $CONH_2$ and 5-(1H-tetrazole);

t and v are independently 0 or 1 such that t+v=1;

Q is a saturated or unsaturated straight chain hydrocarbon containing 2–4 carbon atoms and p is 0–2.

21. A method according to claim 20 wherein the compound has an $IC_{50}$ equal to or less than 10 $\mu$M in the hPPARδ binding assay and an $EC_{50}$ equal to or less than 10 $\mu$M in the hPPARδ transactivation assay.

22. The method of claim 21 wherein the compound has an $IC_{50}$ equal to or less than 100 nM in the hPPARδ binding assay and an $EC_{50}$ equal to or less than 100 nM in the hPPARδ transactivation assay.

23. The method of claim 22 wherein the compound has an $IC_{50}$ equal to or less than 50 nM in the hPPARδ binding assay and an $EC_{50}$ equal to or less than 50 nM in the hPPARδ transactivation assay.

24. The method of claim 23 wherein the compound has an $IC_{50}$ equal to or less than 10 nM in the hPPARδ binding assay and an $EC_{50}$ equal to or less than 10 nM in the hPPARδ transactivation assay.

25. A method for raising high densisty lipoprotein plasma levels in a patient in need of such treatment, comprising the administration of a pharmaceutically effective amount of a compound of formula I.

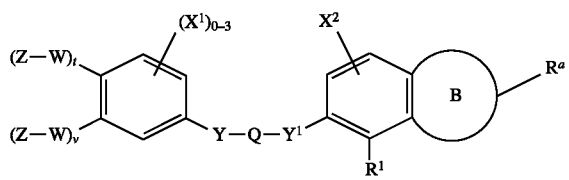

or a pharmaceutically acceptable salt thereof, wherein:
R is selected from the group consisting of H, $C_{1-6}$ alkyl, $C_{5-10}$ aryl, and $C_{5-10}$ heteroaryl, said alkyl, aryl and heteroaryl optionally substituted with 1 to 3 groups of $R^a$;
$R^1$ is selected from a group consisting of: H, $C_{1-15}$ alkyl, $C_{2-15}$ alkenyl, $C_{2-15}$ alkynyl and $C_{3-10}$ cycloalkyl, said alkyl, alkenyl, alkynyl, and cycloalkyl optionally substituted with 1 to 3 groups of $R^a$;
$R^3$ is selected from a group consisting of: H, $NHR^1$, NHacyl, $C_{1-15}$ alkyl, $C_{3-10}$ cycloalkyl, $C_{2-15}$ alkenyl, $C_{1-15}$ alkoxy, $CO_2$alkyl, OH, $C_{2-15}$ alkynyl, $C_{5-10}$ aryl, $C_{5-10}$ heteroaryl said alkyl, cycloalkyl, alkenyl, alkynyl, aryl and heteroaryl optionally substituted with 1 to 3 groups of $R^a$;
(Z—W—) is Z—$CR^6R^7$—, Z—CH=CH—, or

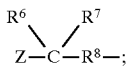

$R^8$ is selected from the group consisting of $CR^6R^7$, O, $NR^6$, and $S(O)_P$;
$R^6$ and $R^7$ are independently selected from the group consisting of H, $C_{1-6}$ alkyl;
B is selected from the group consisting of:
1) a 5 or 6 membered heterocycle containing 0 to 2 double bonds, and 1 heteroatom selected from the group consisting of O, S and N, heteroatom being substituted at any position on the five or six membered heterocycle, the heterocycle being optionally unsubstituted or substituted with 1 to 3 groups of $R^a$;
2) a 5 or 6 membered carbocycle containing 0 to 2 double bonds, the carbocycle optionally unsubstituted or substituted with 1 to 3 groups of $R^a$ at any position on the five or six membered carbocycle; and
3) a 5 or 6 membered heterocycle containing 0 to 2 double bonds, and 3 heteroatoms selected from the group consisting of O, N, and S, which are substituted at any position on the five or six membered heterocycle, the heterocycle being optionally unsubstituted or substituted with 1 to 3 groups of $R^a$;
$X^1$ and $X^2$ are independently selected from a group consisting of: H, OH, $C_{1-15}$ alkyl, $C_{2-15}$ alkenyl, $C_{2-15}$ alkynyl, halo, $OR^3$, $ORCF_3$, $C_{5-10}$ aryl, $C_{5-10}$ aralkyl, $C_{5-10}$ heteroaryl and $C_{1-10}$ acyl, said alkyl, alkenyl, alkynyl, aryl and heteroaryl optionally substituted with 1 to 3 groups of $R^a$;
$R^a$ represents a member selected from the group consisting of: halo, acyl, aryl, heteroaryl, $CF_3$, $OCF_3$, —O—, CN, $NO_2$, $R^3$, $OR^3$; $SR^3$, =N(OR), $S(O)R^3$, $SO_2R^3$, $NR^3R^3$, $NR^3COR^3$, $NR^3CO_2R^3$, $NR^3CON(R^3)_2$, $NR^3SO_2R^3$, $COR^3$, $CO_2R^3$, $CON(R^3)_2$, $SO_2N(R^3)_2$, $OCON(R^3)_2$ said aryl and heteroaryl optionally substituted with 1 to 3 groups of halo or C1–6 alkyl;

Y is selected from the group consisting of: $S(O)_p$, —$CH_2$—, —C(O)—, —C(O)NH—, —NR—, —O—, —$SO_2NH$, —$NHSO_2$;
$Y^1$ is selected from the group consisting of: O and C;
Z is selected from the group consisting of: $CO_2R^3$, $R^3CO_2R^3$, $CONHSO_2Me$, $CONH_2$ and 5-(1H-tetrazole);
t and v are independently 0 or 1 such that t+v=1
Q is a saturated or unsaturated straight chain hydrocarbon containing 2–4 carbon atoms and
p is 0–2.

26. A method according to claim 25 wherein the compound has an $IC_{50}$ equal to or less than 10 μM in the hPPARδ binding assay and an $EC_{50}$ equal to or less than 10 μM in the hPPARδ transactivation assay.

27. The method of claim 26 wherein the compound has an $IC_{50}$ equal to or less than 100 nM in the hPPARδ binding assay and an $EC_{50}$ equal to or less than 100 nM in the hPPARδ transactivation assay.

28. The method of claim 27 wherein the compound has an $IC_{50}$ equal to or less than 50 nM in the hPPARδ binding assay and an $EC_{50}$ equal to or less than 50 nM in the hPPARδ transactivation assay.

29. The method of claim 28 wherein the compound has an $IC_{50}$ equal to or less than 10 nM in the hPPARδ binding assay and an $EC_{50}$ equal to or less than 10 nM in the hPPARδ transactivation assay.

30. A method for the treatment or prevention of diabetes which comprises administering to a diabetic patient an effective amount of a compound of claim 17 in combination with a sulfonylurea, fibrate, HMG-CoA reductase inhibitor, beta-sitosterol inhibitor, cholesterol acyltransferase inhibitor, biguanides, cholestyramine, angiotensin II antagonist, melinamide, nicotinic acid, fibrinogen receptor antagonists, aspirin, α-glucosidase inhibitors, insulin secretogogue or insulin.

31. A method for halting, preventing or reducing the risk of developing atherosclerosis and related disease events which comprises administering to a patient in need thereof an effective amount of a compound of claim 20 in combination with a sulfonylurea, fibrate, HMG-CoA reductase inhibitor, beta-sitosterol inhibitor, cholesterol acyltransferase inhibitor, biguanides, cholestyramine, angiotensin II antagonist, melinamide, nicotinic acid, fibrinogen receptor antagonists, aspirin, α-glucosidase inhibitors, insulin secretogogue or insulin.

32. A method according to claim 31 wherein the compound has an $IC_{50}$ equal to or less than 10 μM in the hPPARδ binding assay and an $EC_{50}$ equal to or less than 10 μM in the hPPARδ transactivation assay.

33. The method of claim 32 wherein the compound has an $IC_{50}$ equal to or less than 100 nM in the hPPARδ binding assay and an $EC_{50}$ equal to or less than 100 nM in the hPPARδ transactivation assay.

34. The method of claim 33 wherein the compound has an $IC_{50}$ equal to or less than 50 nM in the hPPARδ binding assay and an $EC_{50}$ equal to or less than 50 nM in the hPPARδ transactivation assay.

35. The method of claim 34 wherein the compound has an $IC_{50}$ equal to or less than 10 nM in the hPPARδ binding assay and an $EC_{50}$ equal to or less than 10 nM in the hPPARδ transactivation assay.

36. A method for the treatment or prevention of obesity which comprises administering to an obese patient an effective amount of a compound of claim 19 in combination with a fenfluramine, dexfenfluramine, phentiramine or $β_3$ adrenergic receptor agonist.

37. A compound in accordance with claim 1 wherein B represents a five membered heterocycle containing one double bond, and 1 heteroatom which is O, the heteroatom being at any position on the five membered ring, and being optionally unsubstituted or substituted with 1–3 groups selected from $R^a$.

38. A compound represented by the formula:

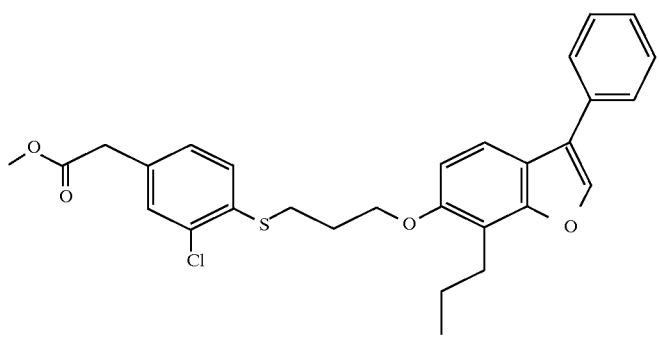

or a pharmaceutically acceptable salt thereof.

39. A pharmaceutical composition comprised of a compound in accordance with claim 1 in combination with a pharmaceutically acceptable carrier.